(12) United States Patent
Arnold et al.

(10) Patent No.: US 7,803,806 B2
(45) Date of Patent: Sep. 28, 2010

(54) PYRIMIDINYL-THIOPHENE KINASE MODULATORS

(75) Inventors: William D. Arnold, San Diego, CA (US); Chixu Chen, San Diego, CA (US); Stefan N. Gradl, San Diego, CA (US); Stephanie A. Hopkins, Poway, CA (US); Ruo W. Steensma, La Jolla, CA (US); Masaki Tomimoto, Osaka (JP); Mark E. Wilson, Ramona, CA (US)

(73) Assignee: SGX Pharmaceuticals, Inc., San Diego, CA (US)

( * ) Notice: Subject to any disclaimer, the term of this patent is extended or adjusted under 35 U.S.C. 154(b) by 928 days.

(21) Appl. No.: 11/556,033

(22) Filed: Nov. 2, 2006

(65) Prior Publication Data

US 2007/0117800 A1 May 24, 2007

Related U.S. Application Data

(60) Provisional application No. 60/733,585, filed on Nov. 3, 2005.

(51) Int. Cl.
| | |
|---|---|
| C07D 239/42 | (2006.01) |
| A61K 31/506 | (2006.01) |
| A61P 19/02 | (2006.01) |
| A61P 35/00 | (2006.01) |

(52) U.S. Cl. ................................ 514/275; 544/331
(58) Field of Classification Search ................ 544/331; 514/275
See application file for complete search history.

(56) References Cited

U.S. PATENT DOCUMENTS

| | | | |
|---|---|---|---|
| 5,162,328 A | 11/1992 | Paul et al. | |
| 5,643,734 A | 7/1997 | Henderson | |
| 6,589,950 B1 | 7/2003 | Collingwood et al. | |
| 6,642,227 B2 * | 11/2003 | Cao et al. ................ | 514/227.8 |
| 2003/0220330 A1 | 11/2003 | Yoshitaka et al. | |

FOREIGN PATENT DOCUMENTS

| | | |
|---|---|---|
| EP | 0233461 A2 | 8/1987 |
| EP | 0453731 A2 | 10/1991 |
| WO | WO97/19065 A1 | 5/1997 |
| WO | WO02/083667 A2 | 10/2002 |
| WO | WO-03-087816 A1 | 10/2003 |
| WO | WO-2005-095386 A1 | 10/2005 |
| WO | WO2005/095386 A1 | 10/2005 |
| WO | WO2006/044457 A1 | 4/2006 |
| WO | WO-2007-018941 A2 | 2/2007 |
| WO | WO-2007-018941 A3 | 2/2007 |

OTHER PUBLICATIONS

Cecil Textbook of Medicine, edited by Bennet, J.C., and Plum F., 20th edition, vol. 1, 1004-1010, 1996.*
Cohen et al., Current Opinion in Chemical Biology, 3,459-465, 1999.*
Dermer et al., Bio/Technology, 1994, 12:320.*
Freshney et al., Culture of Animal Cells, A Manual of Basic Technique, Alan R. Liss, Inc., 1983, New York, p. 4.*
Golub et al., Science, 286, 531-537, 1999.*
Powell et al., British Journal of Dermatology, 141: 802-810, 1999.*
Mass, R. D., Int. J. Radiation Oncology Bio. Phys. vol. 58(3): 932-940, 2004.*
Fabbro et al. Pharmacology & therapeutics 93, 79-98, 2002.*
Bursavich, Matthew G., et al. "Expedient Parallel Synthesis of 2-Amino-4-heteroarylpyrimidines", *Organic Letters* (2005) 7(19):4113-4116.
Zimmermann, Jürg, et al. "Phenylamino-Pyrimidine (PAP)—Derivatives: A New Class of Potent and Highly Selective PDGF-Receptor Autophosphorylation Inhibitors", *Bioorganic & Medicinal Chemistry Letters* (1996) 6(11):1221-1226.
Zimmermann, Jürg, et al. "Phenylamino-Pyrimidine (PAP) Derivatives: A New Class of Potent and Selective Inhibitors of Protein Kinase C (PKC)", *Arch. Pharm. Pharm. Med. Chem.* (1996) 329(7):371-376.
Paul, Rolf, et al. "Preparation of Substituted N-Phenyl-4-aryl-2-pyrimidinamines as Mediator Release Inhibitors", *J. Med. Chem.* (1993) 36(19):2716-2725.
Harrington, "VX-680, a potent and selective small-molecule inhibitor of the Auror kinases, suppresses tumor growth in vivo," Nature Medicine Advance Online Publication: 1-6 (2004).
Feldman et al. "Novel Small Molecule Inhibitors of 3-Phosphoinositide-Dependent Kinase -1 (PDK1)," JBC Papers in Press: 1-24, Published Mar. 16, 2005 Manuscript M501367200.
Berge et al., "Pharmaceutical Salts," J. Pharma. Sci. 66:1-19 (1977).
Yin et al., "Pd-Catalyzed N-Arylation of Heteroarylamines," Org. Ltrs. 4(20):3481-3484 (2002).
Thompson et al. "DbClustal: rapid and reliable global multiple alignments of protein sequences detected by database searches," Nucl. Acids Res. 28:2919-2926 (2000).
Gouet et al., "ESPript: analysis of multiple sequence alignments in PostScript," Bioinformatics 15:305-308 (1999).
Altschul et al., "Gapped BLAST and PSI-BLAST: a new generation of protein database search programs," Nucl. Acids Res. 24:3389-3402 (1997).
Blaney, J.M. and Dixon, J.S., "A good ligand is hard to find: Automated docking methods," Perspectives in Drug Discovery and Design 1:301-319 (1993).
Brooks et al., "CHARMM: A program for macromolecular energy, minimization, and dynamics calculations," J. Comp. Chem. 4:187-217 (1983).
Weiner et al., "A new force field for molecular mechanical simulation of nucleic acids and proteins," J. Am. Chem. Soc. 106:765-784 (1984).
Kuntz et al., "A Geometric Approach to Macromolecule-Ligand Interactions," J. Mol. Biol. 161:269-288 (1982).

(Continued)

Primary Examiner—Venkataraman Balasubramanian
(74) Attorney, Agent, or Firm—James J. Sales

(57) ABSTRACT

The present invention provides novel pyrimidinyl-thiophene kinase modulators and methods of using the novel pyrimidinyl-thiophene kinase modulators to treat diseases mediated by kinase activity.

3 Claims, No Drawings

OTHER PUBLICATIONS

Jones et al., "Molecular Recognition of Receptor Sites using a Genetic Algorithm with a Description of Desolvation," J. Mol. Biol. 245:43-53 (1995).

Rarey, M. et al., "A Fast Flexible Docking Method using an Incremental Construction Algorithm," J. Mol. Biol. 261:470-489 (1996).

Travis, J., "Proteins and Organic Solvents Make an Eye-Opening Mix," Science 262:1374 (1993).

Meng et al., "Automated Docking with Grid-Based Energy Evaluation," J. Comp. Chem. 13:505-524 (1992).

Charifson, P.S. et al., "Consensus Scoring: A Method for Obtaining Improved Hit Rates from Docking Databases of Three-Dimensional Structures into Proteins," J. Med. Chem. 41:5100-5109 (1999).

Balakin, K.V. et al, "Rational Design Approaches to Chemical Libraries for Hit Identification," Curr. Drug Del. Technol. 3:49-65 (2006).

Congreve, M. et al., "Keynote Review: Structural biology and drug discovery," DDT 10(13):895-907 (2005).

Langer, T. and Krovat, E.M., "Chemical feature-based pharmacophones and virtual library screening for discovery of new leads," Curr. Op. Drug Discovery Develop.6(3):370-376 (2003).

Moretti, L. et al., "Tyrosine Kinase Drug Discovery: What Can Be Learned From Solved Crystal Structures?", Issue Italian-Swiss Medicinal Chemistry Meeting, ARKIVOC 2006 (viii), pp. 38-49.

Noble, Martin E.M. et al., "Protein Kinase Inhibitors: Insights Into Drug Design From Structure," Science, vol. 303, Mar. 19, 2004, pp. 1800-1805.

* cited by examiner

PYRIMIDINYL-THIOPHENE KINASE MODULATORS

CROSS-REFERENCE TO RELATED APPLICATIONS

This application claims the benefit of U.S. Provisional Patent Application Ser. No. 60/733,585 entitled "Pyrimidinyl-Thiophene Kinase Modulators", filed Nov. 3, 2006. Priority of the filing date is hereby claimed, and the disclosure of the application is hereby incorporated by reference.

BACKGROUND OF THE INVENTION

Mammalian protein kinases are important regulators of cellular functions. Because dysfunctions in protein kinase activity have been associated with several diseases and disorders, protein kinases are targets for drug development.

The tyrosine kinase receptor, FMS-like tyrosine kinase 3 (FLT3), is implicated in cancers, including leukemia, such as acute myeloid leukemia (AML), acute lymphoblastic leukemia (ALL), and myelodysplasia. About one-quarter to one-third of AML patients have FLT3 mutations that lead to constitutive activation of the kinase and downstream signaling pathways. Although in normal humans, FLT3 is expressed mainly by normal myeloid and lymphoid progenitor cells, FLT3 is expressed in the leukemic cells of 70-80% of patients with AML and ALL. Inhibitors that target FLT3 have been reported to be toxic to leukemic cells expressing mutated and/or constitutively-active FLT3. Thus, there is a need to develop potent FLT3 inhibitors that may be used to treat diseases and disorders such as leukemia.

The Abelson non-receptor tyrosine kinase (c-Abl) is involved in signal transduction, via phosphorylation of its substrate proteins. In the cell, c-Abl shuttles between the cytoplasm and nucleus, and its activity is normally tightly regulated through a number of diverse mechanisms. Abl has been implicated in the control of growth-factor and integrin signaling, cell cycle, cell differentiation and neurogenesis, apoptosis, cell adhesion, cytoskeletal structure, and response to DNA damage and oxidative stress.

The c-Abl protein contains approximately 1150 amino-acid residues, organized into a N-terminal cap region, an SH3 and an SH2 domain, a tyrosine kinase domain, a nuclear localization sequence, a DNA-binding domain, and an actin-binding domain.

Chronic myelogenous leukemia (CML) is associated with the Philadelphia chromosomal translocation, between chromosomes 9 and 22. This translocation generates an aberrant fusion between the bcr gene and the gene encoding c-Abl. The resultant Bcr-Abl fusion protein has constitutively active tyrosine-kinase activity. The elevated kinase activity is reported to be the primary causative factor of CML, and is responsible for cellular transformation, loss of growth-factor dependence, and cell proliferation.

The 2-phenylaminopyrimidine compound imatinib (also referred to as STI-571, CGP 57148, or Gleevec) has been identified as a specific and potent inhibitor of Bcr-Abl, as well as two other tyrosine kinases, c-kit and platelet-derived growth factor receptor. Imatinib blocks the tyrosine-kinase activity of these proteins. Imatinib has been reported to be an effective therapeutic agent for the treatment of all stages of CML. However, the majority of patients with advanced-stage or blast crisis CML suffer a relapse despite continued imatinib therapy, due to the development of resistance to the drug. Frequently, the molecular basis for this resistance is the emergence of imatinib-resistant variants of the kinase domain of Bcr-Abl. The most commonly observed underlying amino-acid substitutions include Glu255Lys, Thr315Ile, Tyr293Phe, and Met351Thr.

MET was first identified as a transforming DNA rearrangement (TPR-MET) in a human osteosarcoma cell line that had been treated with N-methyl-N'-nitro-nitrosoguanidine (Cooper et al. 1984). The MET receptor tyrosine kinase (also known as hepatocyte growth factor receptor, HGFR, MET or c-Met) and its ligand hepatocyte growth factor ("HGF") have numerous biological activities including the stimulation of proliferation, survival, differentiation and morphogenesis, branching tubulogenesis, cell motility and invasive growth. Pathologically, MET has been implicated in the growth, invasion and metastasis of many different forms of cancer including kidney cancer, lung cancer, ovarian cancer, liver cancer and breast cancer. Somatic, activating mutations in MET have been found in human carcinoma metastases and in sporadic cancers such as papillary renal cell carcinoma. The evidence is growing that MET is one of the long-sought oncogenes controlling progression to metastasis and therefore a very interesting target. In addition to cancer there is evidence that MET inhibition may have value in the treatment of various indications including: Listeria invasion, Osteolysis associated with multiple myeloma, Malaria infection, diabetic retinopathies, psoriasis, and arthritis.

The tyrosine kinase RON is the receptor for the macrophage stimulating protein and belongs to the MET family of receptor tyrosine kinases. Like MET, RON is implicated in growth, invasion and metastasis of several different forms of cancer including gastric cancer and bladder cancer.

The Aurora family of serine/threonine kinases is essential for mitotic progression. Expression and activity of the Aurora kinases are tightly regulated during the cell cycle. A variety of proteins having roles in cell division have been identified as Aurora kinase substrates. Based on the known function of the Aurora kinases, inhibition of their activity is believed to disrupt the cell cycle and block proliferation and therefore tumor cell viability. Harrington et al., *Nature Medicine*, advanced publication online (2004).

3-Phosphoinositide-dependent kinase 1 (PDK1) is a Ser/Thr protein kinase that can phosphorylate and activate a number of kinases in the AGC kinase super family, including Akt/PKB, protein kinase C (PKC), PKC-related kinases (PRK1 and PRK2), p70 ribobsomal S6-kinase (S6K1), and serum and glucocorticoid-regulated kinase (SGK). The first identified PDK1 substrate is the proto-oncogene Akt. Numerous studies have found a high level of activated Akt in a large percentage (30-60%) of common tumor types, including melanoma and breast, lung, gastric, prostate, hematological and ovarian cancers. The PDK1/Akt signaling pathway thus represents an attractive target for the development of small molecule inhibitors that may be useful in the treatment of cancer. Feldman et al., *JBC* Papers in Press. Published on Mar. 16, 2005 as Manuscript M501367200.

Because kinases have been implicated in numerous diseases and conditions, such as cancer, there is a need to develop new and potent protein kinase modulators that can be used for treatment. The present invention fulfills these and other needs in the art. Although certain protein kinases are specifically named herein, the present invention is not limited to modulators of these kinases, and, includes, within its scope, modulators of related protein kinases, and modulators of homologous proteins.

BRIEF SUMMARY OF THE INVENTION

It has been discovered that, surprisingly, pyrimidinyl-thiophene compounds of the present invention may be used to modulate kinase activity and to treat diseases mediated by kinase activity. These novel pyrimidinyl-thiophene kinase modulators are described in detail below. In addition, inhibitory activities of selected compounds are disclosed herein.

In one aspect, the present invention provides a pyrimidinyl-thiophene kinase modulator (also referred to herein as a "compound of the present invention") having the formula:

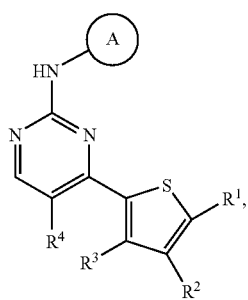

(I)

In the compound of Formula (I), A is a substituted or unsubstituted heteroaryl, or substituted or unsubstituted aryl.

$R^1$ is hydrogen, fluorine, bromine, —$OR^5$, —$(CH_2)_n NR^6R^7$, —$(CH_2)_n C(X^1)R^8$, —$S(O)_w R^9$, —CN, —$NO_2$, —$CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein n is an integer from 0 to 5, and when $R^1$ is a heteroalkyl, the heteroalkyl is not attached via an amide linkage.

$R^2$ is hydrogen, halogen, —$OR^5$, —$NR^6R^7$, —$C(X^1)R^8$, —$S(O)_w R^9$, —CN, —$NO_2$, —$CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is hydrogen, halogen, —$OR^5$, —$NR^6R^7$, —$C(X^1)R^8$, —$S(O)_w R^9$, —CN, —$NO_2$, —$CF_3$, substituted or unsubstituted alkyl, or substituted or unsubstituted heteroalkyl. In some embodiments, where $R^3$ is an alkyl substituted with a cyclic group (e.g. cycloalkyl, heterocycloalkyl, aryl, and/or heteroaryl) the cyclic group is not attached to the remainder of the molecule though a methylene linkage. $R^3$ is an alkyl substituted with a cyclic group (e.g. cycloalkyl, heterocycloalkyl, aryl, and/or heteroaryl) the cyclic group is not attached to the remainder of the molecule though a ethylene linkage.

$R^4$ is hydrogen, halogen, —$OR^5$, —$NR^6R^7$, —$C(X^1)R^8$, —$S(O)_w R^9$, —CN, —$NO_2$, —$CF_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$X^1$ is independently =$N(R^{40})$, =S, or =O, wherein $R^{40}$ is hydrogen, substituted or unsubstituted alkyl, substituted or unsubstituted heteroalkyl, substituted or unsubstituted aryl, or substituted or unsubstituted heteroaryl.

The symbol w independently represents an integer from 0 to 2.

$R^5$ is independently hydrogen, —$CF_3$, —$C(O)R^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ and $R^7$ are independently hydrogen, —$C(O)R^{10}$, —$S(O)_2 R^{11}$, —$C(NH)R^{10}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted arylalkyl, or substituted or unsubstituted heteroaryl.

$R^{10}$ is hydrogen, —$NR^{12}R^{13}$, —$OR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, where $R^6$ is $C(NH)R^{10}$ then $R^{10}$ not $OR^{16}$.

$R^{11}$ is hydrogen, —$NR^{12}R^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{12}$ and $R^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^8$ is independently hydrogen, —$NR^{14}R^{15}$, —$OR^{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{14}$, $R^{15}$, and $R^{16}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Where w is 2, $R^9$ may optionally be —$NR^{17}R^{18}$.

$R^{17}$ and $R^{18}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ and $R^7$, $R^6$ and $R^{10}$, $R^{12}$ and $R^{13}$, $R^{14}$ and $R^{15}$, and $R^{17}$ and $R^{18}$ may independently be optionally joined with the nitrogen to which they are attached to form substituted or unsubstituted heterocycloalkyl, or substituted or unsubstituted heteroaryl.

When $R^1$ is —$C(Z)R^8$, Z is O, $R^8$ is —$NR^{14}R^{15}$ and A is phenyl, then A is a substituted phenyl wherein the substituted phenyl is not substituted with halogen or alkoxy. In some embodiments, when $R^1$ is —$C(Z)R^8$, Z is O, $R^8$ is —$NR^{14}R^{15}$, A is not substituted phenyl. In some embodiments, when $R^1$ is —$C(Z)R^8$, Z is O, $R^8$ is —$NR^{14}R^{15}$, A is not phenyl. In some embodiments, when $R^1$ is —$C(Z)R^8$, Z is O, $R^8$ is —$NR^{14}R^{15}$, A is not substituted aryl. In some embodiments, when $R^1$ is —$C(Z)R^8$, Z is O, $R^8$ is —$NR^{14}R^{15}$, A is not aryl. In some embodiments, $R^1$ is not —$C(Z)R^8$ where Z is O, and $R^8$ is —$NR^{14}R^{15}$.

In another aspect, the present invention provides methods of modulating protein kinase activity using the pyrimidinyl-thiophene kinase modulators of the present invention. The method includes contacting said kinase with a pyrimidinyl-thiophene kinase modulator of the present invention.

In another aspect, the present invention provides methods of treating a disease mediated by kinase activity (kinase-mediated disease or disorder) in a subject (e.g. mammals, such as humans) in need of such treatment. The method includes administering to the subject an effective amount of a pyrimidinyl-thiophene kinase modulator of the present invention.

In another aspect, the present invention provides a pharmaceutical composition including a pyrimidinyl-thiophene kinase modulator in admixture with a pharmaceutically acceptable excipient.

DETAILED DESCRIPTION OF THE INVENTION

Definitions

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —CH$_2$CH$_2$CH$_2$CH$_2$—, —CH$_2$CH=CHCH$_2$—, —CH$_2$C≡CCH$_2$—, —CH$_2$CH$_2$CH(CH$_2$CH$_2$CH$_3$)CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P, S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4- oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" referrers to a carbon or heteroatom.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR"C(O)NR'R", —OC(O)NR'R", —NR"C(O)R', —NR—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen radical. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The symbol  denotes the point of attachment of a moiety to the remainder of the molecule.

Pyrimidinyl-Thiophene Kinase Modulators

In one aspect, the present invention provides a pyrimidinyl-thiophene kinase modulator (also referred to herein as a "compound of the present invention") having the formula:

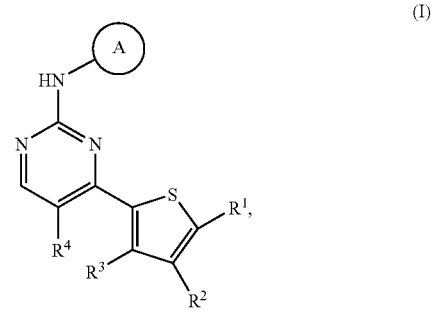

(I)

A, $R^1$, $R^2$, $R^3$, and $R^4$ are as defined above.

In some embodiments, A is an $R^{19}$-substituted or unsubstituted heteroaryl, or $R^{19}$-substituted or unsubstituted aryl.

In some embodiments, $R^1$ is hydrogen, bromine, fluorine, —$OR^5$, —$NR^6R^7$, —$C(X^1)R^8$, —$S(O)_wR^9$, —CN, —$NO_2$, —$CF_3$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In some embodiments, $R^2$ is hydrogen, halogen, —$OR^5$, —$NR^6R^7$, —$C(X^1)R^8$, —$S(O)_wR^9$, —CN, —$NO_2$, —$CF_3$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In some embodiments, $R^3$ is hydrogen, halogen, —$OR^5$, —$NR^6R^7$, —$C(X^1)R^8$, —$S(O)_wR^9$, —CN, —$NO_2$, —$CF_3$, $R^{19}$-substituted or unsubstituted alkyl, or $R^{19}$-substituted or unsubstituted heteroalkyl.

In some embodiments, $R^4$ is hydrogen, halogen, —$OR^5$, —$NR^6R^7$, —$C(X^1)R^8$, —$S(O)_wR^9$, —CN, —$NO_2$, —$CF_3$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In some embodiments, $X^1$ is independently =$N(R^{40})$, =S, or =O, wherein $R^{40}$ is hydrogen, $R^{19}$-substituted or unsubstituted alkyl, $R^{19}$-substituted or unsubstituted heteroalkyl, $R^{19}$-substituted or unsubstituted aryl, or $R^{19}$-substituted or unsubstituted heteroaryl.

In some embodiments, $R^5$ is independently hydrogen, —$CF_3$, —$C(O)R^{10}$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In some embodiments, $R^6$ and $R^7$ are independently hydrogen, —$C(O)R^{10}$, —$S(O)_2R^{11}$, —$C(NH)R^{10}$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In some embodiments, $R^{10}$ is hydrogen, $-NR^{12}R^{13}$, $-OR^{16}$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In some embodiments, $R^{11}$ is hydrogen, $-NR^{12}R^{13}$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In some embodiments, $R^{12}$ and $R^{13}$ are independently hydrogen, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In some embodiments, $R^{8}$ is independently hydrogen, $-NR^{14}R^{15}$, $-OR^{16}$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In some embodiments, $R^{14}$, $R^{15}$, and $R^{16}$ are independently hydrogen, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In some embodiments, $R^{9}$ is independently hydrogen, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In some embodiments, $R^{17}$ and $R^{18}$ are independently hydrogen, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

In some embodiments, $R^{6}$ and $R^{7}$, $R^{6}$ and $R^{10}$, $R^{12}$ and $R^{13}$, $R^{14}$ and $R^{15}$, and $R^{17}$ and $R^{18}$ are, independently, optionally joined with the nitrogen to which they are attached to form $R^{19}$-substituted or unsubstituted heterocycloalkyl, or $R^{19}$-substituted or unsubstituted heteroaryl.

$R^{19}$ is independently halogen, -L$^{1}$-C(X$^{2}$)R$^{22}$, -L$^{1}$-OR$^{23}$, -L$^{1}$-NR$^{24}$R$^{25}$, -L$^{1}$-S(O)$_m$R$^{26}$, $-CN$, $-NO_2$, $-CF_3$, (1) unsubstituted $C_3$-$C_7$ cycloalkyl; (2) unsubstituted 3 to 7 membered heterocycloalkyl; (3) unsubstituted heteroaryl; (4) unsubstituted aryl; (5) substituted $C_3$-$C_7$ cycloalkyl; (6) substituted 3 to 7 membered heterocycloalkyl; (7) substituted aryl; (8) substituted heteroaryl; (9) unsubstituted $C_1$-$C_{20}$ alkyl; (10) unsubstituted 2 to 20 membered heteroalkyl; (11) substituted $C_1$-$C_{20}$ alkyl; or (12) substituted 2 to 20 membered heteroalkyl.

(5), (6), (11), and (12) are independently substituted with an oxo, $-OH$, $-CF_3$, $-COOH$, cyano, halogen, $R^{20}$-substituted or unsubstituted $C_1$-$C_{10}$ alkyl, $R^{20}$-substituted or unsubstituted 2 to 10 membered heteroalkyl, $R^{20}$-substituted or unsubstituted $C_3$-$C_7$ cycloalkyl, $R^{20}$-substituted or unsubstituted 3 to 7 membered heterocycloalkyl, $R^{21}$-substituted or unsubstituted aryl, $R^{21}$-substituted or unsubstituted heteroaryl, -L$^{1}$-C(X$^{2}$)R$^{22}$, -L$^{1}$-OR$^{23}$, -L$^{1}$-NR$^{24}$R$^{25}$, or -L$^{1}$-S(O)$_m$R$^{26}$.

(7) and (8) are independently substituted with an $-OH$, $-CF_3$, $-COOH$, cyano, halogen, $R^{20}$-substituted or unsubstituted $C_1$-$C_{10}$ alkyl, $R^{20}$-substituted or unsubstituted 2 to 10 membered heteroalkyl, $R^{20}$-substituted or unsubstituted $C_3$-$C_7$ cycloalkyl, $R^{20}$-substituted or unsubstituted 3 to 7 membered heterocycloalkyl, $R^{21}$-substituted or unsubstituted aryl, $R^{21}$-substituted or unsubstituted heteroaryl, -L$^{1}$-C(X$^{2}$)R$^{22}$, -L$^{1}$-OR$^{23}$, -L$^{1}$-NR$^{24}$R$^{25}$, or -L$^{1}$-S(O)$_m$R$^{26}$.

$X^{2}$ is independently $=S$, $=O$, or $=NR^{27}$, wherein $R^{27}$ is H, $-OR^{28}$, $R^{20}$-substituted or unsubstituted $C_1$-$C_{10}$ alkyl, $R^{20}$-substituted or unsubstituted 2 to 10 membered heteroalkyl, $R^{20}$-substituted or unsubstituted $C_3$-$C_7$ cycloalkyl, $R^{20}$-substituted or unsubstituted 3 to 7 membered heterocycloalkyl, $R^{21}$-substituted or unsubstituted aryl, or $R^{21}$-substituted or unsubstituted heteroaryl. $R^{28}$ is independently hydrogen or $R^{20}$-substituted or unsubstituted $C_1$-$C_{10}$ alkyl.

The symbol m is independently an integer from 0 to 2.

$R^{22}$ is independently hydrogen, $R^{20}$-substituted or unsubstituted $C_1$-$C_{10}$ alkyl, $R^{20}$-substituted or unsubstituted 2 to 10 membered heteroalkyl, $R^{20}$-substituted or unsubstituted $C_3$-$C_7$ cycloalkyl, $R^{20}$-substituted or unsubstituted 3 to 7 membered heterocycloalkyl, $R^{21}$-substituted or unsubstituted aryl, $R^{21}$-substituted or unsubstituted heteroaryl, $-OR^{29}$, or $-NR^{30}R^{31}$.

$R^{29}$, $R^{30}$, and $R^{31}$ are independently hydrogen, $R^{20}$-substituted or unsubstituted $C_1$-$C_{10}$ alkyl, $R^{20}$-substituted or unsubstituted 2 to 10 membered heteroalkyl, $R^{20}$-substituted or unsubstituted $C_3$-$C_7$ cycloalkyl, $R^{20}$-substituted or unsubstituted 3 to 7 membered heterocycloalkyl, $R^{21}$-substituted or unsubstituted aryl, or $R^{21}$-substituted or unsubstituted heteroaryl. $R^{30}$ and $R^{31}$ are optionally joined with the nitrogen to which they are attached to form an $R^{20}$-substituted or unsubstituted 3 to 7 membered heterocycloalkyl, or $R^{21}$-substituted or unsubstituted heteroaryl.

$R^{23}$, $R^{24}$ and $R^{25}$ are independently hydrogen, $-CF_3$, $R^{20}$-substituted or unsubstituted $C_1$-$C_{10}$ alkyl, $R^{20}$-substituted or unsubstituted 2 to 10 membered heteroalkyl, $R^{20}$-substituted or unsubstituted $C_3$-$C_7$ cycloalkyl, $R^{20}$-substituted or unsubstituted 3 to 7 membered heterocycloalkyl, $R^{21}$-substituted or unsubstituted aryl, $R^{21}$-substituted or unsubstituted heteroaryl, $-C(X^{3})R^{32}$, or $-S(O)_qR^{32}$ wherein $R^{24}$ and $R^{25}$ are optionally joined with the nitrogen to which they are attached to form an $R^{20}$-substituted or unsubstituted 3 to 7 membered heterocycloalkyl, or $R^{21}$-substituted or unsubstituted heteroaryl.

$X^{3}$ is independently $=S$, $=O$, or $=NR^{33}$. $R^{33}$ is independently $R^{20}$-substituted or unsubstituted $C_1$-$C_{10}$ alkyl, $R^{20}$-substituted or unsubstituted 2 to 10 membered heteroalkyl, $R^{20}$-substituted or unsubstituted $C_3$-$C_7$ cycloalkyl, $R^{20}$-substituted or unsubstituted 3 to 7 membered heterocycloalkyl, $R^{21}$-substituted or unsubstituted aryl, or $R^{21}$-substituted or unsubstituted heteroaryl.

The symbol q is independently an integer from 0 to 2.

$R^{32}$ is independently hydrogen, $R^{20}$-substituted or unsubstituted $C_1$-$C_{10}$ alkyl, $R^{20}$-substituted or unsubstituted 2 to 10 membered heteroalkyl, $R^{20}$-substituted or unsubstituted $C_3$-$C_7$ cycloalkyl, $R^{20}$-substituted or unsubstituted 3 to 7 membered heterocycloalkyl, $R^{21}$-substituted or unsubstituted aryl, $R^{21}$-substituted or unsubstituted heteroaryl, or $-NR^{34}R^{35}$.

$R^{34}$ and $R^{35}$ are independently hydrogen, $R^{20}$-substituted or unsubstituted $C_1$-$C_{10}$ alkyl, $R^{20}$-substituted or unsubstituted 2 to 10 membered heteroalkyl, $R^{20}$-substituted or unsubstituted $C_3$-$C_7$ cycloalkyl, $R^{20}$-substituted or unsubstituted 3 to 7 membered heterocycloalkyl, $R^{21}$-substituted or unsubstituted aryl, or $R^{21}$-substituted or unsubstituted heteroaryl. $R^{34}$ and $R^{35}$ are optionally joined with the nitrogen to which they are attached to form an $R^{20}$-substituted or unsubstituted 3 to 7 membered heterocycloalkyl, or $R^{21}$-substituted or unsubstituted heteroaryl.

$R^{26}$ is independently hydrogen, $R^{20}$-substituted or unsubstituted $C_1$-$C_{10}$ alkyl, $R^{20}$-substituted or unsubstituted 2 to 10 membered heteroalkyl, $R^{20}$-substituted or unsubstituted $C_3$-$C_7$ cycloalkyl, $R^{20}$-substituted or unsubstituted 3 to 7 membered heterocycloalkyl, $R^{21}$-substituted or unsubstituted aryl, $R^{21}$-substituted or unsubstituted heteroaryl, or —$NR^{36}R^{37}$.

$R^{36}$ and $R^{37}$ are independently hydrogen, $R^{20}$-substituted or unsubstituted $C_1$-$C_{10}$ alkyl, $R^{20}$-substituted or unsubstituted 2 to 10 membered heteroalkyl, $R^{20}$-substituted or unsubstituted $C_3$-$C_7$ cycloalkyl, $R^{20}$-substituted or unsubstituted 3 to 7 membered 21-substituted or unsubstituted heteroaryl. $R^{36}$ and $R^{37}$ are optionally joined with the nitrogen to which they are attached to form an $R^{20}$-substituted or unsubstituted 3 to 7 membered heterocycloalkyl, or $R^{21}$-substituted or unsubstituted heteroaryl;

$L^1$ is independently a bond, unsubstituted $C_1$-$C_{10}$ alkylene, or unsubstituted heteroalkylene;

$R^{20}$ is independently oxo, —OH, —COOH, —$CF_3$, —$OCF_3$, —CN, amino, halogen, $R^{38}$-substituted or unsubstituted 2 to 10 membered alkyl, $R^{38}$-substituted or unsubstituted 2 to 10 membered heteroalkyl, $R^{38}$-substituted or unsubstituted $C_3$-$C_7$ cycloalkyl, $R^{38}$-substituted or unsubstituted 3 to 7 membered heterocycloalkyl, $R^{39}$-substituted or unsubstituted aryl, or $R^{39}$-substituted or unsubstituted heteroaryl.

$R^{21}$ is independently —OH, —COOH, amino, halogen, —$CF_3$, —$OCF_3$, —CN, $R^{38}$-substituted or unsubstituted 2 to 10 membered alkyl, $R^{38}$-substituted or unsubstituted 2 to 10 membered heteroalkyl, $R^{38}$-substituted or unsubstituted $C_3$-$C_7$ cycloalkyl, $R^{38}$-substituted or unsubstituted 3 to 7 membered heterocycloalkyl, $R^{39}$-substituted or unsubstituted aryl, or $R^{39}$-substituted or unsubstituted heteroaryl.

$R^{38}$ is independently oxo, —OH, —COOH, amino, halogen, —$CF_3$, —$OCF_3$, —CN, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl.

$R^{39}$ is independently —OH, —COOH, amino, halogen, —$CF_3$, —$OCF_3$, —CN, unsubstituted $C_1$-$C_{10}$ alkyl, unsubstituted 2 to 10 membered heteroalkyl, unsubstituted $C_3$-$C_7$ cycloalkyl, unsubstituted 3 to 7 membered heterocycloalkyl, unsubstituted aryl, unsubstituted heteroaryl.

In some embodiments, A is substituted or unsubstituted phenyl, substituted or unsubstituted pyridinyl, substituted or unsubstituted pyrimidinyl, substituted or unsubstituted oxazolyl, substituted or unsubstituted pyrrolyl, substituted or unsubstituted furanyl, substituted or unsubstituted imidazolyl, substituted or unsubstituted thioazolyl, substituted or unsubstituted isoxazolyl, substituted or unsubstituted pyrazolyl, substituted or unsubstituted inodolyl, substituted or unsubstituted benzothiazolyl, or substituted or unsubstituted isothiazolyl.

In some embodiments, A is substituted or unsubstituted phenyl. In some embodiments, the $R^{19}$ substituent of A is independently halogen, substituted or unsubstituted $C_1$-$C_{20}$ alkyl, -$L^1$-$C(X^2)R^{22}$, -$L^1$-$OR^{23}$, -$L^1$-$NR^{24}R^{24}$, or -$L^1$-$S(O)_m$ $R^{26}$, —CN, or —$NO_2$. In some embodiments, the $L^1$ linkage to A is a bond. In some embodiments, the $R^{23}$ group bound to A is independently hydrogen or unsubstituted ($C_1$-$C_5$) alkyl. In some embodiments, the $X^2$ of A is =O. In some embodiments, the $R^{22}$ of linked to A is independently $R^{20}$-substituted or unsubstituted $C_1$-$C_{10}$ alkyl, $R^{20}$-substituted or unsubstituted 2 to 10 membered heteroalkyl, $R^{20}$-substituted or unsubstituted 3 to 7 membered heterocycloalkyl, —$OR^{29}$, or —$NR^{30}R^{31}$. The symbol m when included as a -$L^1$-$S(O)_m R^{26}$ substituent of A may be 2. The $R^{26}$ linked to A may be $R^{20}$-substituted or unsubstituted $C_1$-$C_{10}$ alkyl, $R^{20}$-substituted or unsubstituted 2 to 10 membered heteroalkyl. The $R^{26}$ linked to A may also be unsubstituted ($C_1$-$C_5$) alkyl.

In some embodiments, the $R^{19}$ of A is independently an $R^{20}$-substituted or unsubstituted $C_1$-$C_{20}$ alkyl, or $R^{20}$-substituted or unsubstituted $C_1$-$C_{20}$ heteroalkyl. The $R^{20}$ of A may also independently be -$L^1$-$OR^{23}$, -$L^1$-$NR^{24}R^{25}$, or unsubstituted heterocycloalkyl. The $R^{20}$ linked to A may also independently be $R^{38}$-substituted or unsubstituted piperidinyl or $R^{38}$-substituted or unsubstituted morpholino. In some embodiments, the $L^1$ of A is a bond. In some embodiments, the $R^{23}$ of A is independently hydrogen, unsubstituted $C_1$-$C_5$ alkyl, or unsubstituted 2 to 5 membered heteroalkyl. In some embodiments, the $R^{24}$ bound to A is hydrogen The $R^{25}$ attached to A may independently be $R^{20}$-substituted or unsubstituted $C_1$-$C_5$ alkyl, or $R^{20}$-substituted or unsubstituted 2 to 5 membered heteroalkyl.

In some embodiments, $R^2$ and $R^4$ are independently hydrogen, halogen, —$OR^5$, —$NR^6R^7$, —$C(X^1)R^8$, —$S(O)_wR^9$, —CN, —$NO_2$, —$CF_3$, unsubstituted ($C_1$-$C_{10}$) alkyl, unsubstituted 2 to 10 membered heteroalkyl, unsubstituted ($C_3$-$C_7$) cycloalkyl, unsubstituted 3 to 7 membered heterocycloalkyl, unsubstituted aryl, or substituted or unsubstituted heteroaryl. $R^3$ may be hydrogen, halogen, —$OR^5$, —$NR^6R^7$, —$C(X^1)R^8$, —$S(O)_wR^9$, —CN, —$NO_2$, —$CF_3$, unsubstituted ($C_1$-$C_{10}$) alkyl, or unsubstituted 2 to 10 membered heteroalkyl.

In some embodiments, the $R^5$, $R^6$, $R^7$, $R^8$, and $R^9$ groups attached to $R^2$, $R^4$, and $R^3$ are independently unsubstituted ($C_1$-$C_{10}$) alkyl, unsubstituted 2 to 10 membered heteroalkyl, unsubstituted ($C_3$-$C_7$) cycloalkyl, unsubstituted 3 to 7 membered heterocycloalkyl, unsubstituted aryl, or substituted or unsubstituted heteroaryl. In some embodiments, the $R^5$, $R^6$, $R^7$, $R^8$, and $R^9$ of the $R^2$, $R^4$, and $R^3$ groups are independently unsubstituted ($C_1$-$C_{10}$) alkyl or unsubstituted 2 to 10 membered heteroalkyl.

In some embodiments, $R^3$, $R^2$, and/or $R^4$ are hydrogen. In some embodiments, $R^2$, $R^4$, and $R^3$ are hydrogen.

In some embodiments, $R^1$ is —$OR^5$, —$NR^6R^7$, —$C(X^1)R^8$, —$S(O)_wR^9$, $R^{19}$-substituted or unsubstituted ($C_1$-$C_{10}$) alkyl, $R^{19}$-substituted or unsubstituted 2 to 10 membered heteroalkyl, $R^{19}$-substituted or unsubstituted ($C_3$-$C_7$) cycloalkyl, $R^{19}$-substituted or unsubstituted 3 to 7 membered heterocycloalkyl, $R^{19}$-substituted or unsubstituted aryl, or $R^{19}$-substituted or unsubstituted heteroaryl.

In some embodiments, $R^1$ is —$C(X^1)R^8$. In some embodiments, the $X^1$ of $R^1$ is =O, and the $R^8$ of $R^1$ is —$NR^{14}R^{15}$. In some embodiments, the $R^{14}$ and $R^{15}$ attached to $R^1$ through the nitrogen are independently hydrogen, or $R^{19}$-substituted or unsubstituted alkyl. In some embodiments, the $R^{19}$ of $R^1$ is independently —OH, —CN, substituted or unsubstituted 2 to 10 membered alkyl, or substituted or unsubstituted aryl. In some embodiments, $R^1$ is $R^{19}$-substituted or unsubstituted aryl, or $R^{19}$-substituted or unsubstituted heteroaryl. In some embodiments, $R^1$ is $R^{19}$-substituted or unsubstituted phenyl, $R^{19}$-substituted or unsubstituted pyridinyl, $R^{19}$-substituted or unsubstituted pyrimidinyl, or $R^{19}$-substituted or unsubstituted benzothiophenyl.

In some embodiments, the $R^{19}$ of $R^1$ is independently halogen, -$L^1$-$C(X^2)R^{22}$, -$L^1$-$OR^{21}$, -$L^1$-$NR^{24}R^{25}$, substituted or unsubstituted $C_1$-$C_{20}$ alkyl, or substituted or unsubstituted aryl. In some embodiments, the $R^{19}$ of $R^1$ is -$L^1$-$C(X^2)R^{22}$. The $L^1$ of $R^1$ may be a bond. The $X^2$ of $R^1$ may be O. The $R^{22}$ of the $R^1$ may be —$NR^{30}R^{31}$. $R^{30}$ and $R^{31}$ bound to $R^1$ via the nitrogen may independently be hydrogen, $R^{20}$-substituted or unsubstituted alkyl, R²⁰-substituted or unsubstituted heterocycloalkyl, or R²¹-substituted or unsubstituted aryl.

In some embodiments, the R¹⁹ of R¹ is independently -L¹-OR²³. The L¹ of R¹ may be a bond or unsubstituted C₁-C₁₀ alkylene. The R²³ of R¹ may be R²⁰-substituted or unsubstituted alkyl, or R²¹-substituted or unsubstituted aryl.

In some embodiments, R¹⁹ of R¹ is -L¹-NR²⁴R²⁵. L¹ of R¹ may be a bond. The R²⁴ and R²⁵ of R¹ may independently be hydrogen, or R²⁰-substituted or unsubstituted alkyl.

In some embodiments, R¹ is —NR⁶R⁷. The R⁶ of R¹ may be hydrogen or unsubstituted C₁-C₅ alkyl. The R⁷ of R¹ may be —C(O)R¹⁰. R⁶ and R¹⁰ may be joined with the nitrogen to which they are attached to form an R¹⁹-substituted or unsubstituted heterocycloalkyl, or an R¹⁹-substituted or unsubstituted heteroaryl. In some embodiments, R¹⁰ of R¹ is —OR¹⁶, R¹⁹-substituted or unsubstituted alkyl, or R¹⁹-substituted or unsubstituted aryl.

In some embodiments, R¹ is —S(O)_wR⁹. The w of R¹ may be 2. The R⁹ of R¹ may be —NR¹⁷R¹⁸. In some embodiments, R¹⁷ and R¹⁸ of R¹ are independently R¹⁹-substituted or unsubstituted alkyl, R¹⁹ substituted or unsubstituted heteroalkyl. Or R¹⁷ and R¹⁸ are joined with the nitrogen to which they are attached to form R¹⁹-substituted or unsubstituted heterocycloalkyl. In some embodiments, the R¹⁷ and R¹⁸ of R¹ are joined with the nitrogen to which they are attached to form R¹⁹-substituted or unsubstituted piperidinyl, or R¹⁹-substituted or unsubstituted piperazinyl.

In some embodiments, each substituted group described above in the compound of Formula (I) is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, and/or substituted heteroalkylene, described above in the compounds of Formula (I) is substituted with at least one substituent group. In other embodiments, at least one or all of these groups are substituted with at least one size-limited substituent group. Alternatively, at least one or all of these groups are substituted with at least one lower substituent group.

In other embodiments of the compounds of Formula (I), each substituted or unsubstituted alkyl is a substituted or unsubstituted C₁-C₂₀ alkyl, each substituted or unsubstituted heteroalkyl is a substituted or unsubstituted 2 to 20 membered heteroalkyl, each substituted or unsubstituted cycloalkyl is a substituted or unsubstituted C₄-C₈ cycloalkyl, each substituted or unsubstituted heterocycloalkyl is a substituted or unsubstituted 4 to 8 membered heterocycloalkyl, each substituted or unsubstituted alkylene is a substituted or unsubstituted C₁-C₂₀ alkylene, and/or each substituted or unsubstituted heteroalkylene is a substituted or unsubstituted 2 to 20 membered heteroalkylene.

Alternatively, each substituted or unsubstituted alkyl is a substituted or unsubstituted C₁-C₈ alkyl, each substituted or unsubstituted heteroalkyl is a substituted or unsubstituted 2 to 8 membered heteroalkyl, each substituted or unsubstituted cycloalkyl is a substituted or unsubstituted C₅-C₇ cycloalkyl, each substituted or unsubstituted heterocycloalkyl is a substituted or unsubstituted 5 to 7 membered heterocycloalkyl, each substituted or unsubstituted alkylene is a substituted or unsubstituted C₁-C₈ alkylene, and/or each substituted or unsubstituted heteroalkylene is a substituted or unsubstituted 2 to 8 membered heteroalkylene.

In another embodiment, the compounds of the present invention include the compounds of any one or all of Tables 1-9, or any one or all of the methods 1-9.

Exemplary Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate how, in principle, to gain access to the compounds claimed under this invention and to give details on certain of the diverse methods available for use in assembling the compounds of the invention. However, the discussion is not intended to define or limit the scope of reactions or reaction sequences that are useful in preparing the compounds of the present invention. The compounds of this invention may be made by the procedures and techniques disclosed in the Examples section below, as well as by known organic synthesis techniques. In Schemes 1-10, R¹, R², R³, R⁴ and A are defined as above.

The synthesis of the sulfonamide analogs of the current invention is outlined in Scheme 1 (R¹=SO₂NR^aR^b). Many of such compounds are synthesized conveniently from commercially available 5-(2-methylsulfanyl-pyrimidin-4-yl)-thiophene-2-sulfonyl chloride.

Scheme 1

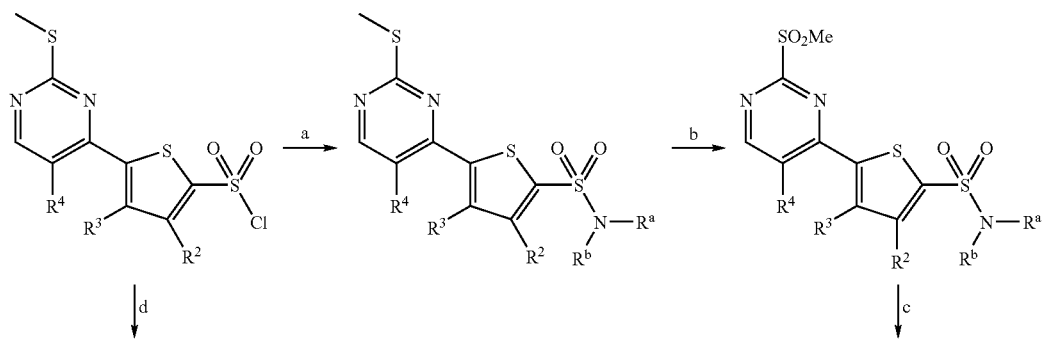

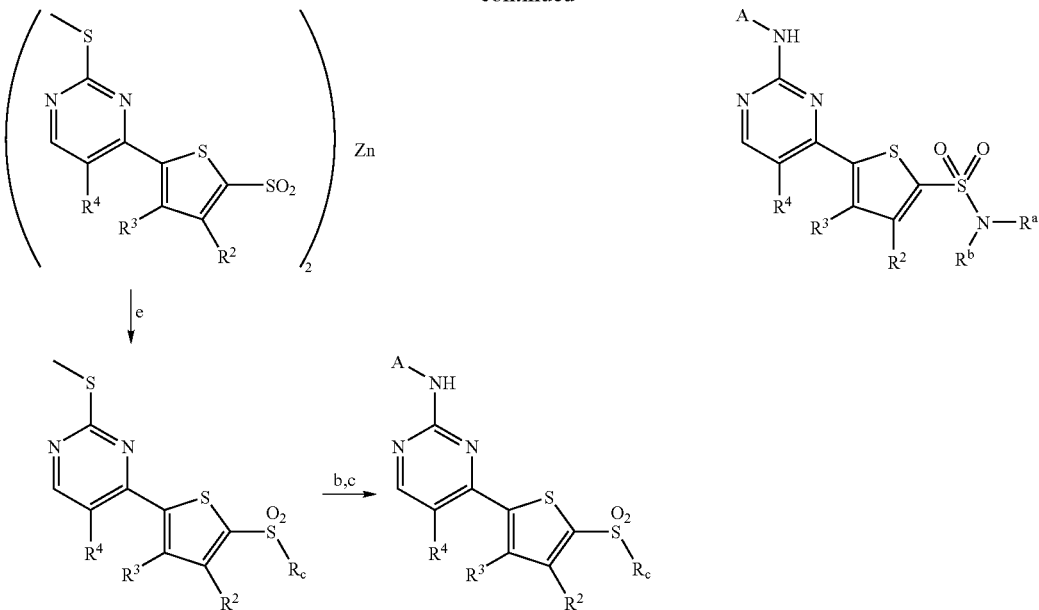

The sulfonyl chloride is transformed to the sulfonamide by reacting with an amine under basic conditions, for example, but not limited to, pyridine (step a). The resulting methyl sulfide is oxidized to the corresponding sulfone by a variety of oxidants such as, but not limited to, m-CPBA, oxone, $H_2O_2$ or TBHP (step b). Substitution of the sulfone by an aryl amine is effected by using a neat aromatic amine or with an acidic catalyst (ie. TFA, HOAc, P-TSA) in an appropriate solvent (n-BuOH, DMSO, DMF, $CH_3CN$, etc.), typically at an elevated temperature. Alternatively, the transformation could be achieved under either basic conditions (eg. NaH) in an appropriate solvent (eg. DMF) or metallic catalysis (ie. Pd or Cu) as exemplified by Yin et al., *Organic Letters* 2002, 4(20), 3481. In addition, hydrolysis of the sulfone followed by chlorination with $POCl_3$, $PCl_5$, or other halogenating agents could also generate the 2-halopyrimidine analog, which could be conveniently substituted by aromatic amines under either basic conditions (eg. NaH, DIPA, etc.) or facilitated by organometallic catalysts (eg. $Pd(PPh_3)_4$, $Pd_2(dba)_3$) (step c in scheme 1).

The sulfonyl chloride could also be converted to an organozinc derivative (step d) under standard conditions (Sugen-WO02096361A2), which was then treated with alkyl halides to generated sulfonyl intermediate (step e). The subsequent transformation to the final products could be achieved by applying the conditions for steps b and c as described above.

The synthesis of the bromo analogs ($R^1$=Br) is outlined in Schemes 2 and 3.

Scheme 2

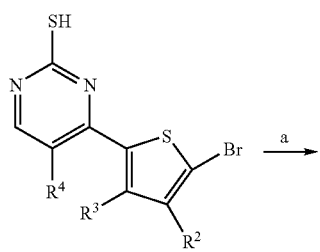

One method uses commercially available 4-(5-bromothiophen-2-yl)-pyrimidine thiol as a key starting material (Scheme 2). Methylation of the thiol is effected by methylating agents, such as, but not limited to MeI, under basic conditions (ie. $K_2CO_3$, NaH) in a suitable solvent (ie. EtOH/$H_2O$, DCM, THF, etc.) (step a). Oxidation (step b) and substitution of the sulfone (step c) are accomplished under similar conditions as described in scheme 1, steps b and c.

Scheme 3

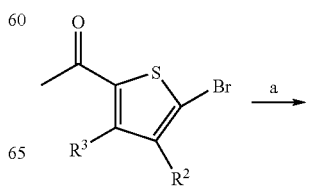

-continued

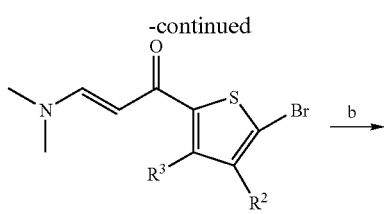

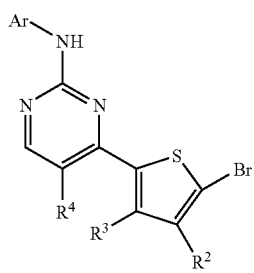

Another method is to treat 2-acetyl-5-bromothiophene with dimethylformamide dimethylacetal (DMF-DMA) or Bredereck's reagent neat or in solvent (DMF, DMA) to afford the acrylamide (step a in Scheme 3). The cyclization of acrylamide with an arylguanidine, easily prepared from cyanamide and arylamine in ethanolic $HNO_3$, is carried out with a base such as NaOH, KOH, etc. in a solvent such as ethanol, 2-methoxyethanol, etc. at an elevated temperature (step b).

4-(5-Bromo-2-thienyl)-2-pyrimidinyl-N-arylamines obtained via Scheme 2 or 3 are easily converted to 5-arylthienyl analogs ($R^1$=aryl) or 5-N-arylthiophen-amino analog ($R^1$=N-aryl) (Scheme 4).

Scheme 4

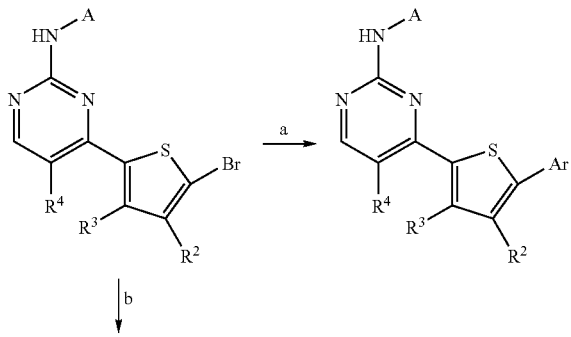

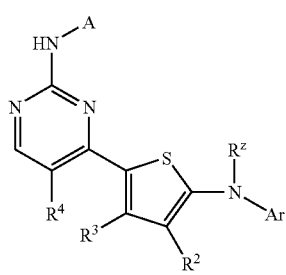

The synthesis of the 5-arylthienyl analogs is achieved by the C—C formation between 5-bromothiophene and a boronic acid, boronic ester or organotin reagent. The reaction usually is conducted under basic conditions (ie. $Na_2CO_3$, KOAc, NaOH etc.) and facilitated by a palladium catalyst such as, but not limited to tetrakis(triphenylphosphino)palladium(0), dichlorbis(triphenylphosphino)palladium(II) or dichloro[1,1'-bis(diphenylphosphino)ferrocene]palladium (II), in the absence or presence of a ligand additive (ie. amines, CsF) in aqueous solvent mixtures such as, but not limited to, DMF, DMA, NMP, $CH_3CN$, dioxane, toluene, etc. at elevated temperatures (90° C.-200° C.) either using conventional heating or microwave irradiation (step a). The 5-N-arylthiophen-amino analogs are prepared under palladium catalyzed conditions developed by Buchwald and others as described in *Organic Letters* (2005), 7(18), 3965-3968. One of such conditions uses $Pd_2(dba)_3$ as the catalyst, NaOtBu as the base and 2-dicyclohexylphosphino-2',6'-dimethoxy-1,1'-biphenyl as the ligand.

Both 5-arylthienyl analogs ($R^1$=aryl) or 5-N-arylthiophen-amino analog ($R^1$=N-aryl) may also be obtained by reversing the order of the arylation steps (Scheme 5). In this method, the bromo on the thiophene is first replaced by an aryl or N-aryl group and then the methylsulfone on the pyrimidine is N-arylated.

Scheme 5

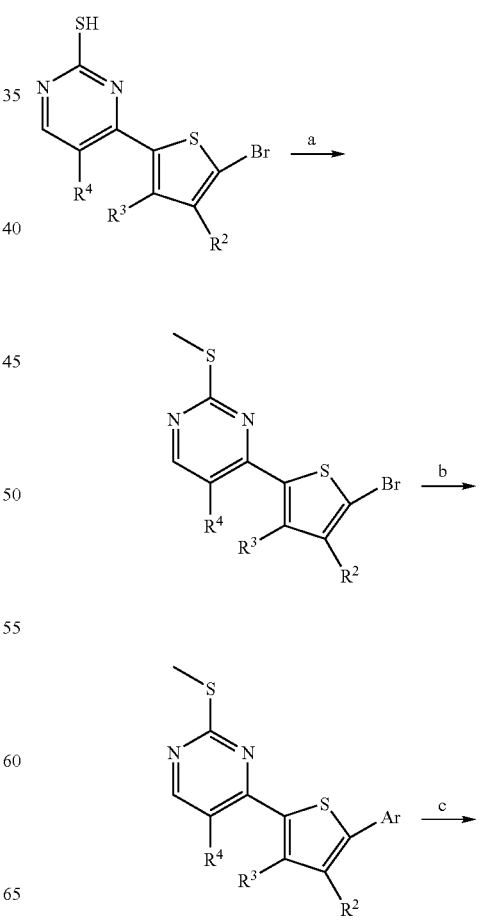

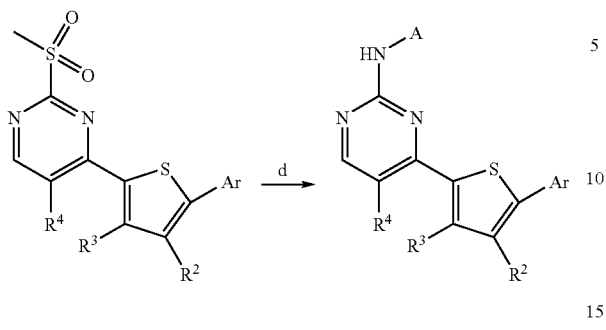

Certain olefins are obtained from 4-(5-bromo-2-thienyl)-2-pyrimidinyl-N-arylamines (from Scheme 2 or 3) under standard Heck reaction conditions (Scheme 6).

Scheme 6

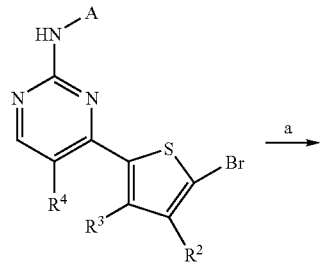

The Wittig reaction also provides an entry into alkene and ethylene linked analogs (Scheme 7). For example, 5-(2-methylsulfanyl-pyrimidin-4-yl)thiophene-2-carbaldehyde is prepared from two the commercially available reagents, 2-methylthiopyrimidine-4-chloride and 5-formyl-2-thiopheneboronic acid, via standard Suzuki coupling conditions as described in Scheme 5, step d, forms (step a in scheme 7). N-Arylation is then performed (step b, see Scheme 1, steps b and c) and the resulting aldehyde is subjected to Wittig reaction conditions to generate the alkenyl derivatives (step c). The same aldehyde is also useful in the synthesis of thienyl-2-aminomethyl analogs via well-established reductive-amination conditions (step c'). When 2,4-dichloro-pyrimidine is used as the starting material, the transformation sequence for steps b and c' could be switched.

Scheme 7

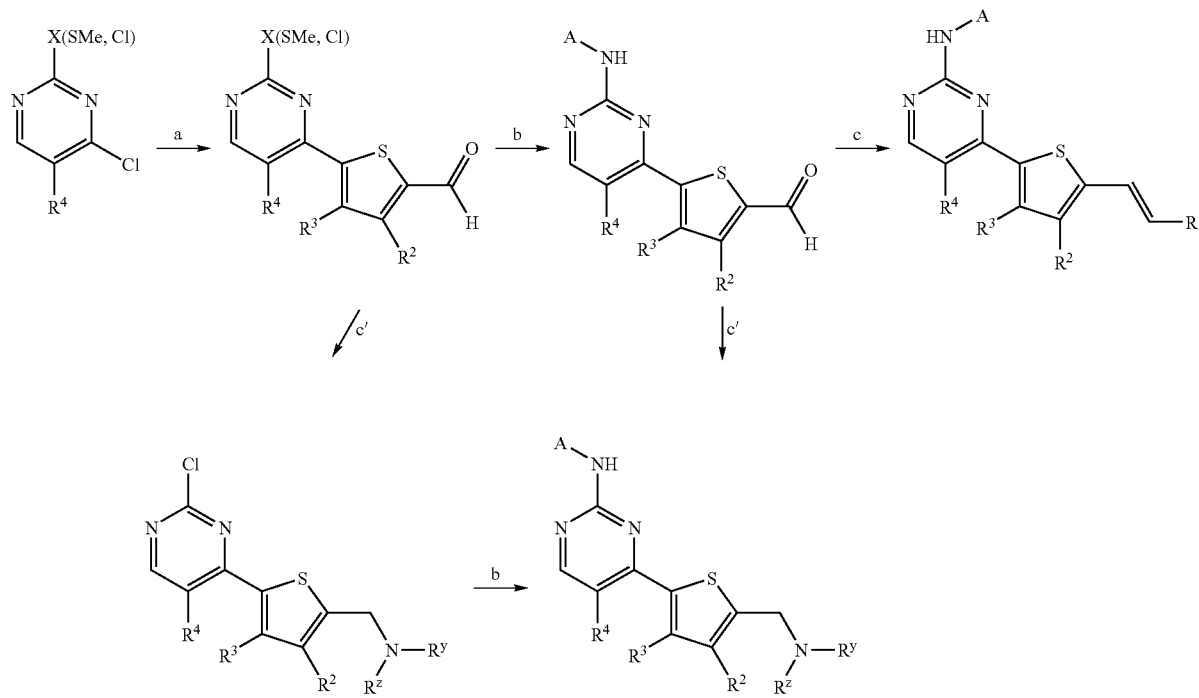

The amido ($R^1$=CONR$^a$R$^b$) analogs in this invention are readily available from either 2-acetylthiophene-2-carboxylic acid or (2-substituted-pyrimidin-4-yl)-thiophene-2-carboxylic acid ester (Scheme 8). Steps a and b are described in Scheme 3, steps a and b. Step d could easily be achieved under either acidic or basic conditions as described in the illustration for Scheme 1 (X could be SO$_2$Me or Cl). Hydrolysis of the carboxylic ester (step e) is carried out under standard conditions (ie. KOH, LiOH or K$_2$CO$_3$). The transformation of step c is achieved under well-established amide coupling conditions with suitable coupling reagents such as, but not limited to, PyBOP, HBTU or HATU. When such amide is Weinreb amide, various ketones could be prepared by using organometallic agents, such as but not limited to, Grignard reagents (step f).

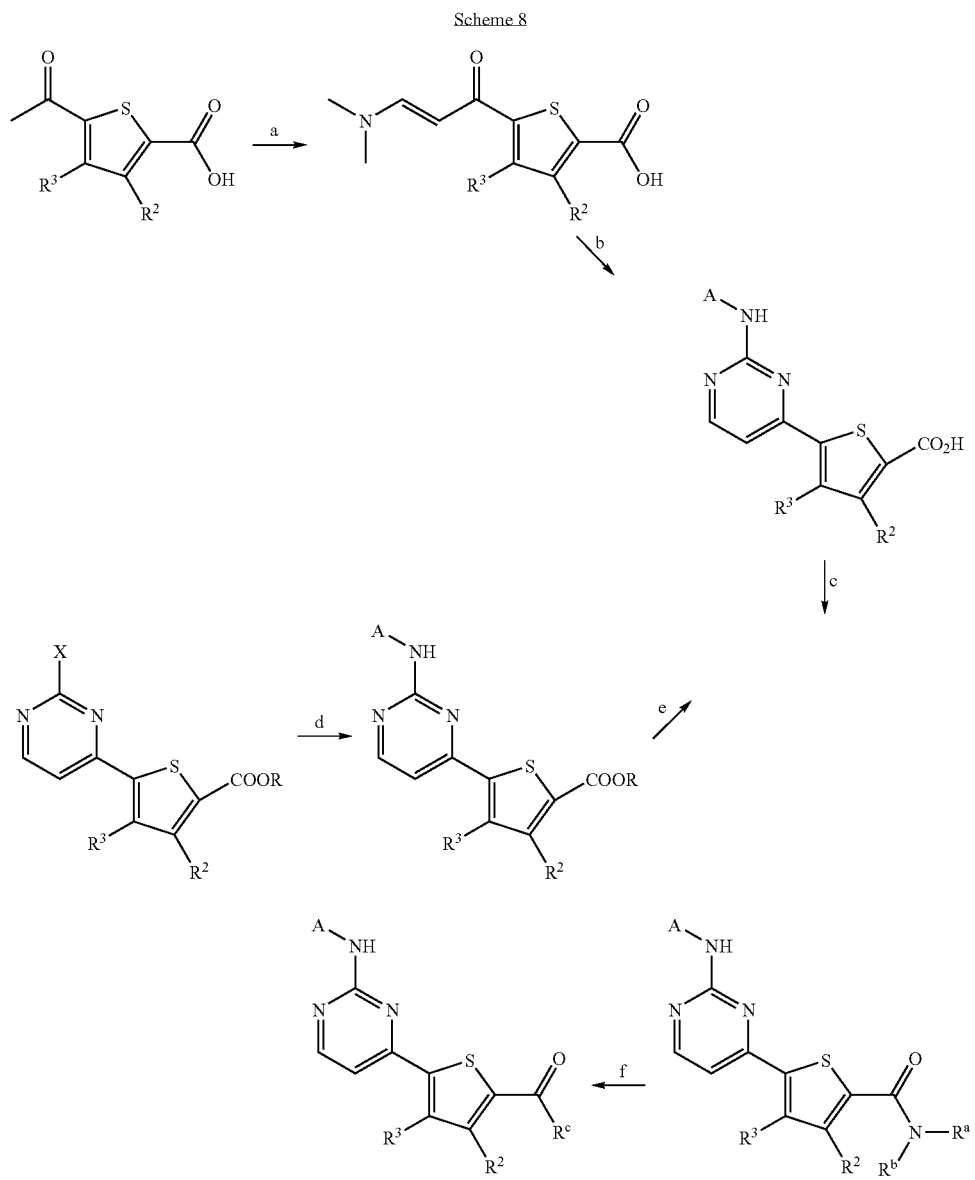

Scheme 8

The synthesis of N-linked amido analogs ($R^1$=N(R$^a$)COR$^b$), ureas ($R^1$=N(R$^a$)CONR$^b$R$^c$) or carbamates ($R^1$=NR$^a$CO$_2$R$^b$) is illustrated in scheme 9.

Scheme 9

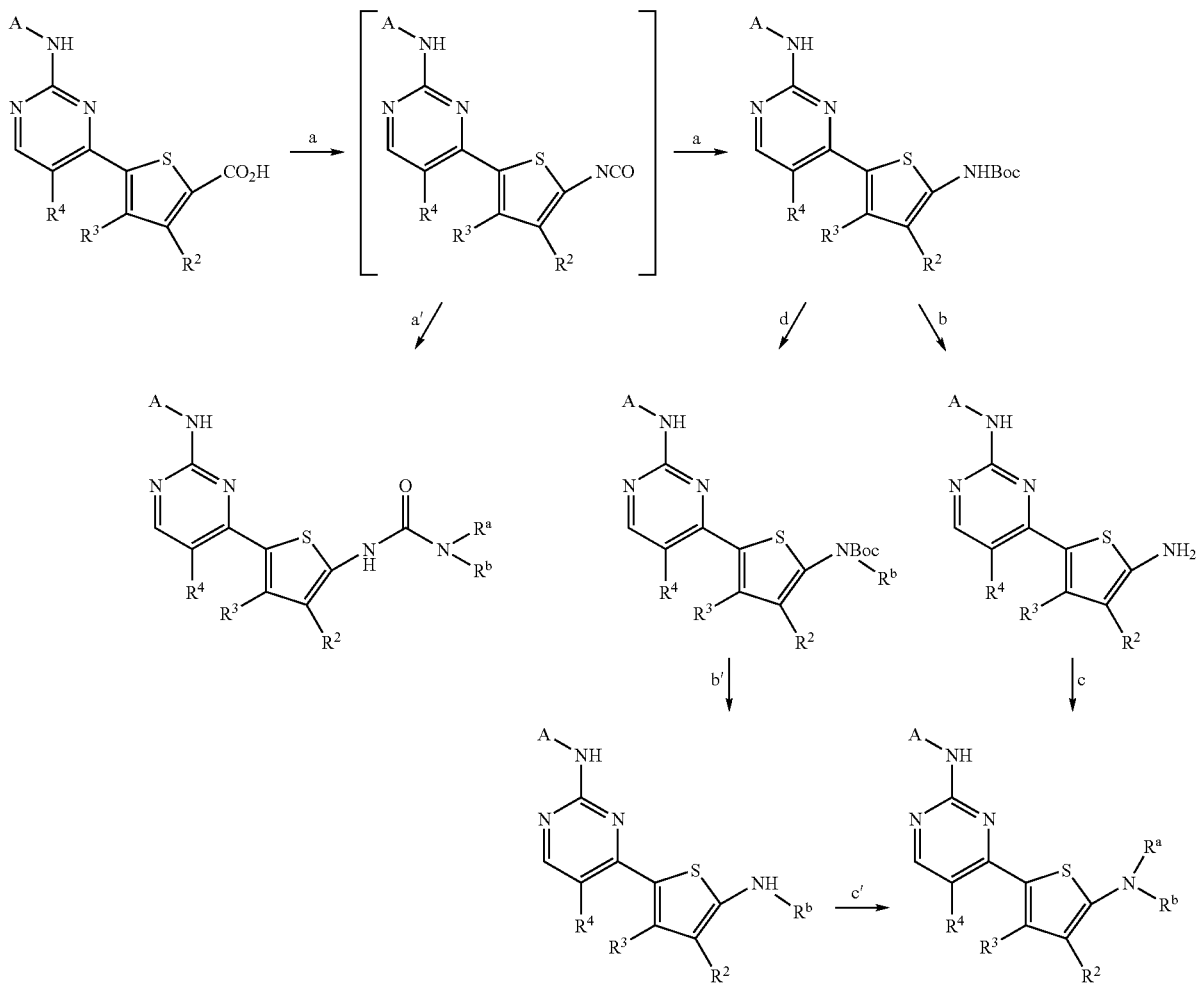

An acid from Scheme 8 (product from step b) is treated with diphenylphosphorylazide and triethylamine in t-BuOH at elevated temperature to afford the rearranged tert-butoxy carbonylaminothienyl intermediate (step a in Scheme 9). Other methods to affect such Curtius rearrangement are also applicable for this transformation. For example, one of such method is to generate an azido intermediate via acid chloride ($SOCl_2$, etc.) and $NaN_3$ in solvents such as, but not limited to, acetonitrile, benzene or THF. The isocyanate intermediate may be treated in situ or isolated and treated with alcohols to afford carbamates ($R^1=NR^cC(O)OR^a$, $R^c=H$) or with amines to afford ureas ($R^1=NR^cC(O)NR^aR^b$, $R^c=H$) (step a'). The resulting ureas or carbamates could be alkylated by, for example, but not limited to alkyl halide (ie. MeI, EtBr) under basic conditions (ie. NaH, $K_2CO_3$) to afford N-alkyl ureas and carbamates ($R^c=$alkyl).

The tert-butoxy carbonylaminothienyl intermediate from step a may either be alkylated first (step d) and then subjected to Boc removal conditions or be subjected to Boc removal conditions directly (ie. TFA/DCM or HCl/dioxane) to generate the aminothienyl analog (step b or b'), which may be alkylated by, for example but not limited to, alkyl halides, or via reductive amination conditions (step c or c'). The product from step b or b' is easily acylated ($R^a=$COR) by acyl halides in the presence of a base (ie., DIEA, $Et_3N$, pyridine) in an appropriate solvent such as, but not limited to, DCM, THF, pyridine (step c or c'). The above amide bond formation may also be achieved by reacting the amine with carboxylic acids in the presence of certain agents such as, but not limited to, HATU, PyBOP, EDCI in an appropriate solvent such as, but not limited to, DCM, DMF, DMA, NMP, AcN or THF. In addition, Schotten-Bauman conditions provide another alternative to the same transformation. Furthermore, dimethylaminopyridine (DMAP) or other "activating" additives may also be used to facilitate step c or c'.

The amines from above are also transformed into sulfonamides ($R^1=NR^bSO_2R^a$; $R^b=H$, alkyl or heteroalkyl) using an activated alkyl or aryl or heteroaryl sulfonyl reagent such as, but not limited to, sulfonyl chloride or sulfonyl imidazolide, in a solvent such as, but not limited to, pyridine, DCM or THF (step c or c'). Alternatively, tertiary sulfonamides ($R^1=NR^bSO_2R^a$; $R^b=$alkyl or heteroalkyl) may also be prepared by subjecting secondary sulfonamides ($R^1=NR^bSO_2R^a$; $R^b=H$) to alkylation conditions, for example, but not limited to alkyl halide (ie. MeI, EtBr) under basic conditions (ie. NaH, $K_2CO_3$) or alkylalcohol under Mitsunobu conditions.

The amines are also transformed into carbamates after being treated with a chloroformate in an appropriated solvent (ie. THF, DCM, AcN) with a base (ie. pyridine, triethylamine).

Diversity at the 2-position of the pyrimidine (A) is accomplished by incorporating functionalizing groups on the phenyl or other aromatic rings at this position. These groups include but not limited to carboxylic acid, aldehyde, hydroxyl, and hydroxymethyl (Scheme 10).

Scheme 10

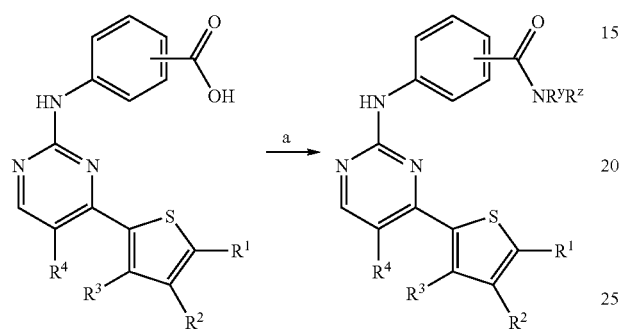

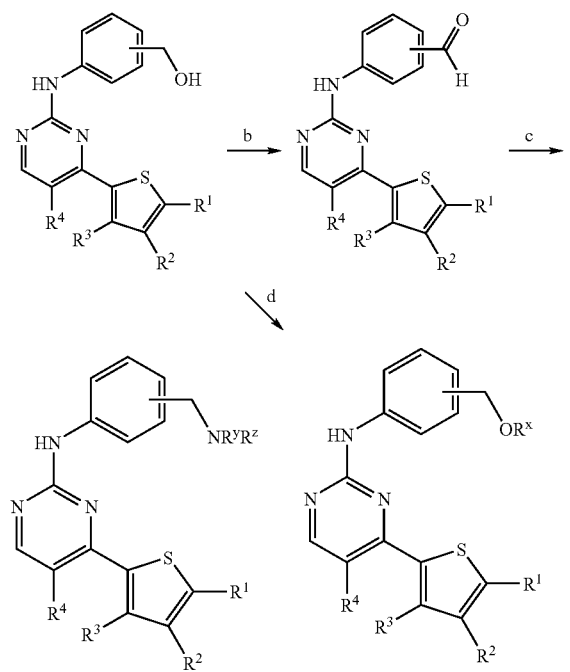

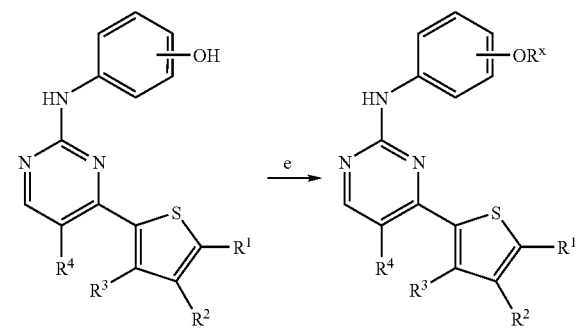

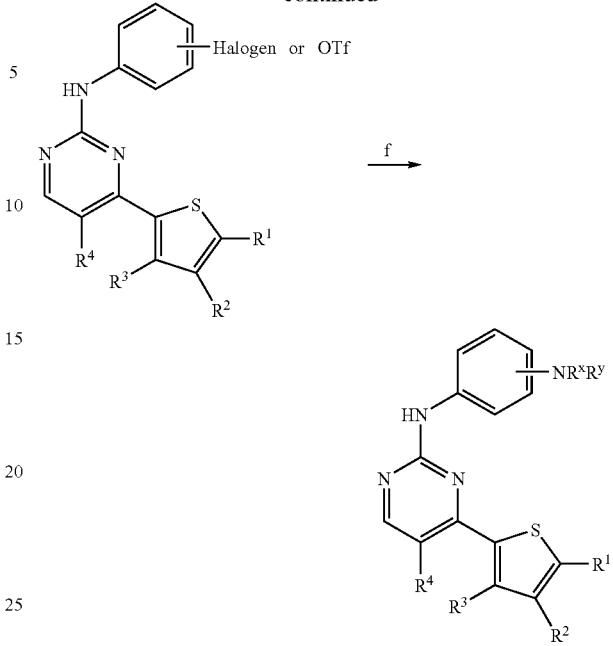

A carboxylic acid group provides a convenient handle for the preparation of various amides under well established amide bond formation conditions (step a). A hydroxymethyl group is directly alkylated to append a heteroalkyl substituent to the aniline (step d) or is oxidized (eg. $MnO_2$) to the aldehyde (step b). The aldehyde then undergoes reductive-amination to afford aminomethyl substituents on the aniline (step c). A hydroxyl group is alkylated by alkyl halides to generate ethers under basic conditions, for example but not limited to, $K_2CO_3$, $CsCO_3$, DBU or PS-DBU in an aprotic solvent. The same transformation may also be achieved under Mitsunobu conditions (step e). The conversion of a halogen or triflate to an amino group is achieved under Buchwald or Ullmann amination conditions (step f). It is apparent to one of the skilled in the art that the aniline elaboration may be performed to deliver either an intermediate or a final product. Efficient synthesis, synthetic possibility and convenience ultimately determine the stage of the elaboration.

Many of the methodologies described above are also applicable to other thiophene regioisomers, such as but not limited to, (4-substituted-thiophen-2-yl)-pyrimidine analogs.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

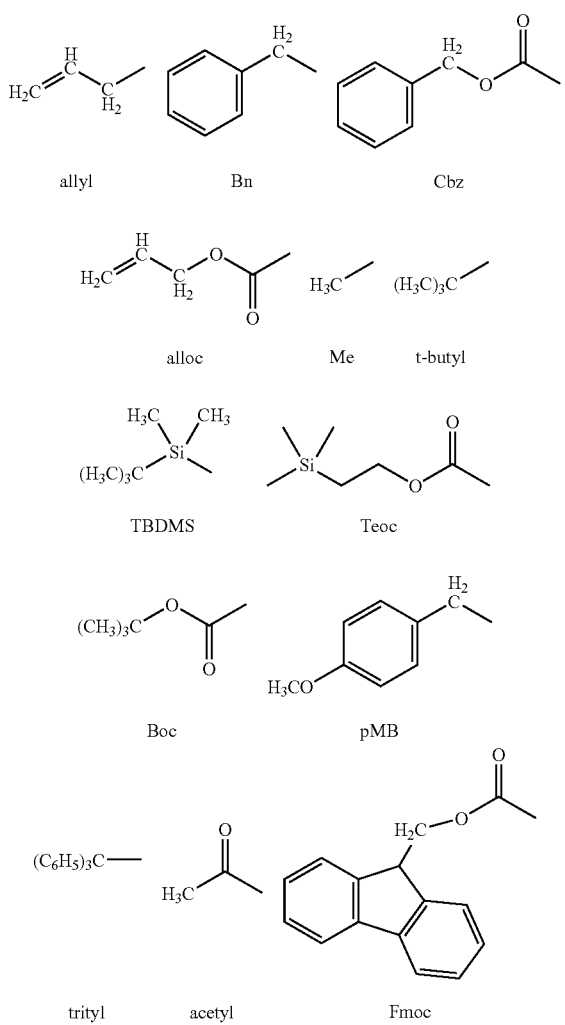

Methods of Inhibiting Kinases

In another aspect, the present invention provides methods of modulating protein kinase activity using the pyrimidinyl-thiophene kinase modulators of the present invention. The term "modulating kinase activity," as used herein, means that the activity of the protein kinase is increased or decreased when contacted with a pyrimidinyl-thiophene kinase modulator of the present invention relative to the activity in the absence of the pyrimidinyl-thiophene kinase modulator. Therefore, the present invention provides a method of modulating protein kinase activity by contacting the protein kinase with a pyrimidinyl-thiophene kinase modulator of the present invention (e.g. the compounds of any one of Formula (I).

In some embodiments, the pyrimidinyl-thiophene kinase modulator inhibits kinase activity. The term "inhibit," as used herein in reference to kinase activity, means that the kinase activity is decreased when contacted with a pyrimidinyl-thiophene kinase modulator relative to the activity in the absence of the pyrimidinyl-thiophene kinase modulator. Therefore, the present invention further provides a method of inhibiting protein kinase activity by contacting the protein kinase with a pyrimidinyl-thiophene kinase modulator of the present invention.

In certain embodiments, the protein kinase is a protein tyrosine kinase. A protein tyrosine kinase, as used herein, refers to an enzyme that catalyzes the phosphorylation of tyrosine residues in proteins with a phosphate donors (e.g. a nucleotide phosphate donor such as ATP). Protein tyrosine kinases include, for example, Abelson tyrosine kinases ("Abl") (e.g. c-Abl and v-Abl), Ron receptor tyrosine kinases ("RON"), Met receptor tyrosine kinases ("MET"), Fms-like tyrosine kinases ("FLT") (e.g. FLT3), src-family tyrosine kinases (e.g. lyn, CSK), and p21-activated kinase-4 ("PAK"), FLT3, aurora kinases, B-lymphoid tyrosine kinases ("Blk"), cyclin-dependent kinases ("CDK") (e.g. CDK1 and CDK5), src-family related protein tyrosine kinases (e.g. Fyn kinase), glycogen synthase kinases ("GSK") (e.g. GSK3α and GSK3β), lymphocyte protein tyrosine kinases ("Lck"), ribosomal S6 kinases (e.g. Rsk1, Rsk2, and Rsk3), sperm tyrosine kinases (e.g. Yes), and subtypes and homologs thereof exhibiting tyrosine kinase activity. In certain embodiments, the protein tyrosine kinase is Abl, RON, MET, PAK, or FLT3. In other embodiments, the protein tyrosine kinase is a FLT3 or Abl family member. In some embodiments, the protein kinase macrophage colony stimulating factor receptor kinase (CSF1R), hematopoietic cell kinase (HCK), Janus kinase 2 (JAK2), kinase insert domain-containing receptor kinase (KDR), tyrosine kinase receptor C (TRKC), Focal Adhesion Kinase (FAK), RET kinase (RET) and ROS1 kinase (ROS1) to the list.

In another embodiment, the kinase is a mutant kinase, such as a mutant Bcr-Abl kinase, FLT3 kinase or aurora kinases.

In some embodiments, the kinase is selected from Aurora kinase, Met receptor tyrosine kinase, CSF1R, HCK, JAK2, KDR, TRKC, FAK, RET and ROS1.

In some embodiments, the kinase is homologous to a known kinase (also referred to herein as a "homologous kinase"). Compounds and compositions useful for inhibiting the biological activity of homologous kinases may be initially screened, for example, in binding assays. Homologous enzymes comprise an amino acid sequence of the same length that is at least 50%, at least 60%, at least 70%, at least 80%, or at least 90% identical to the amino acid sequence of full length known kinase, or 70%, 80%, or 90% homology to the known kinase active domains. Homology may be determined using, for example, a PSI BLAST search, such as, but not limited to that described in Altschul, et al., *Nuc. Acids Rec.*

25:3389-3402 (1997). In certain embodiments, at least 50%, or at least 70% of the sequence is aligned in this analysis. Other tools for performing the alignment include, for example, DbClustal and ESPript, which may be used to generate the PostScript version of the alignment. See Thompson et al., *Nucleic Acids Research*, 28:2919-26, 2000; Gouet, et al., *Bioinformatics*, 15:305-08 (1999). Homologs may, for example, have a BLAST E-value of $1\times10^{-6}$ over at least 100 amino acids (Altschul et al., *Nucleic Acids Res.*, 25:3389-402 (1997) with FLT3, Abl, or another known kinase, or any functional domain of FLT3, Abl, or another known kinase.

Homology may also be determined by comparing the active site binding pocket of the enzyme with the active site binding pockets of a known kinase. For example, in homologous enzymes, at least 50%, 60%, 70%, 80%, or 90% of the amino acids of the molecule or homolog have amino acid structural coordinates of a domain comparable in size to the kinase domain that have a root mean square deviation of the alpha carbon atoms of up to about 1.5 Å, about 1.25 Å, about 1 Å, about 0.75 Å, about 0.5 Å, and or about 0.25 Å.

The compounds and compositions of the present invention are useful for inhibiting kinase activity and also for inhibiting other enzymes that bind ATP. They are thus useful for the treatment of diseases and disorders that may be alleviated by inhibiting such ATP-binding enzyme activity. Methods of determining such ATP binding enzymes include those known to those of skill in the art, those discussed herein relating to selecting homologous enzymes, and by the use of the database PROSITE, where enzymes containing signatures, sequence patterns, motifs, or profiles of protein families or domains may be identified.

The compounds of the present invention, and their derivatives, may also be used as kinase-binding agents. As binding agents, such compounds and derivatives may be bound to a stable resin as a tethered substrate for affinity chromatography applications. The compounds of this invention, and their derivatives, may also be modified (e.g., radiolabelled or affinity labeled, etc.) in order to utilize them in the investigation of enzyme or polypeptide characterization, structure, and/or function.

In an exemplary embodiment, the pyrimidinyl-thiophene kinase modulator of the present invention is a kinase inhibitor. In some embodiments, the kinase inhibitor has an $IC_{50}$ of inhibition constant ($K_i$) of less than 1 micromolar. In another embodiment, the kinase inhibitor has an $IC_{50}$ or inhibition constant ($K_i$) of less than 500 micromolar. In another embodiment, the kinase inhibitor has an $IC_{50}$ or $K_i$ of less than 10 micromolar. In another embodiment, the kinase inhibitor has an $IC_{50}$ or $K_i$ of less than 1 micromolar. In another embodiment, the kinase inhibitor has an $IC_{50}$ or $K_i$ of less than 500 nanomolar. In another embodiment, the kinase inhibitor has an $IC_{50}$ or $K_i$ of less than 10 nanomolar. In another embodiment, the kinase inhibitor has an $IC_{50}$ or $K_i$ of less than 1 nanomolar.

Methods of Treatment

In another aspect, the present invention provides methods of treating a disease mediated by kinase activity (kinase-mediated disease or disorder) in a subject (e.g. mammals, such as humans) in need of such treatment. By "kinase-mediated" or "kinase-associated" diseases is meant diseases in which the disease or symptom can be alleviated by inhibiting kinase activity (e.g. where the kinase is involved in signaling, mediation, modulation, or regulation of the disease process). By "diseases" is meant diseases, or disease symptoms. The method includes administering to the subject an effective amount of a pyrimidinyl-thiophene kinase modulator of the present invention (e.g. the compounds of any one of Formula (I)).

Examples of kinase associated diseases include cancer (e.g. leukemia, tumors, and metastases), allergy, asthma, obesity, inflammation (e.g. inflammatory diseases such as inflammatory airways disease), hematological disorders, obstructive airways disease, asthma, autoimmune diseases, metabolic diseases, infection (e.g. bacterial, viral, yeast, fungal), CNS diseases, brain tumors, degenerative neural diseases, cardiovascular diseases, and diseases associated with angiogenesis, neovascularization, and vasculogenesis. In an exemplary embodiment, the compounds are useful for treating cancer, including leukemia, and other diseases or disorders involving abnormal cell proliferation, such as myeloproliferative disorders. In some embodiments, the compound of Formula (I) is administered to the subject.

More specific examples of cancers treated with the compounds of the present invention include breast cancer, lung cancer, melanoma, colorectal cancer, bladder cancer, ovarian cancer, prostate cancer, renal cancer, squamous cell cancer, glioblastoma, pancreatic cancer, Kaposi's sarcoma, multiple myeloma, and leukemia (e.g. myeloid, chronic myeloid, acute lymphoblastic, chronic lymphoblastic, Hodgkins, and other leukemias and hematological cancers). In some embodiments, the cancer is colon, breast, pancreas, ovarian or gastric cancer.

Other specific examples of diseases or disorders for which treatment by the compounds or compositions of the invention are useful for treatment or prevention include, but are not limited to transplant rejection (for example, kidney, liver, heart, lung, islet cells, pancreas, bone marrow, cornea, small bowel, skin allografts or xenografts and other transplants), graft vs. host disease, osteoarthritis, rheumatoid arthritis, multiple sclerosis, diabetes, diabetic retinopathy, inflammatory bowel disease (for example, Crohn's disease, ulcerative colitis, and other bowel diseases), renal disease, cachexia, septic shock, lupus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, ocular disease, retinopathies (for example, macular degeneration, diabetic retinopathy, and other retinopathies), corneal disease, glaucoma, infections (for example bacterial, viral, or fungal), heart disease, including, but not limited to, restenosis.

Assays

The compounds of the present invention may be easily assayed to determine their ability to modulate protein kinases, bind protein kinases, and/or prevent cell growth or proliferation. Some examples of useful assays are presented below.

Kinase Inhibition and Binding Assays

Inhibition of various kinases is measured by methods known to those of ordinary skill in the art, such as the various methods presented herein, and those discussed in the Upstate KinaseProfiler Assay Protocols June 2003 publication.

For example, where in vitro assays are performed, the kinase is typically diluted to the appropriate concentration to form a kinase solution. A kinase substrate and phosphate donor, such as ATP, is added to the kinase solution. The kinase is allowed to transfer a phosphate to the kinase substrate to form a phosphorylated substrate. The formation of a phosphorylated substrate may be detected directly by any appropriate means, such as radioactivity (e.g. [$\gamma$-$^{32}$P-ATP]), or the use of detectable secondary antibodies (e.g. ELISA). Alternatively, the formation of a phosphorylated substrate may be detected using any appropriate technique, such as the detection of ATP concentration (e.g. Kinase-Glo® assay system (Promega)). Kinase inhibitors are identified by detecting the formation of a phosphorylated substrate in the presence and absence of a test compound (see Examples section below).

The ability of the compound to inhibit a kinase in a cell may also be assayed using methods well known in the art. For example, cells containing a kinase may be contacted with an activating agent (such as a growth factor) that activates the kinase. The amount of intracellular phosphorylated substrate formed in the absence and the presence of the test compound may be determined by lysing the cells and detecting the presence phosphorylated substrate by any appropriate method (e.g. ELISA). Where the amount of phosphorylated substrate produced in the presence of the test compound is decreased relative to the amount produced in the absence of the test compound, kinase inhibition is indicated. More detailed cellular kinase assays are discussed in the Examples section below.

To measure the binding of a compound to a kinase, any method known to those of ordinary skill in the art may be used. For example, a test kit manufactured by Discoverx (Fremont, Calif.), ED-Staurosporine NSIP™ Enzyme Binding Assay Kit (see U.S. Pat. No. 5,643,734) may be used. Kinase activity may also be assayed as in U.S. Pat. No. 6,589,950, issued Jul. 8, 2003.

Suitable kinase inhibitors may be selected from the compounds of the invention through protein crystallographic screening, as disclosed in, for example Antonysamy, et al., PCT Publication No. WO03087816A1, which is incorporate herein by reference in its entirety for all purposes.

The compounds of the present invention may be computationally screened to assay and visualize their ability to bind to and/or inhibit various kinases. The structure may be computationally screened with a plurality of compounds of the present invention to determine their ability to bind to a kinase at various sites. Such compounds can be used as targets or leads in medicinal chemistry efforts to identify, for example, inhibitors of potential therapeutic importance (Travis, *Science*, 262:1374, 1993). The three dimensional structures of such compounds may be superimposed on a three dimensional representation of kinases or an active site or binding pocket thereof to assess whether the compound fits spatially into the representation and hence the protein. In this screening, the quality of fit of such entities or compounds to the binding pocket may be judged either by shape complementarity or by estimated interaction energy (Meng, et al., *J. Comp. Chem.* 13:505-24, 1992).

The screening of compounds of the present invention that bind to and/or modulate kinases (e.g. inhibit or activate kinases) according to this invention generally involves consideration of two factors. First, the compound must be capable of physically and structurally associating, either covalently or non-covalently with kinases. For example, covalent interactions may be important for designing irreversible or suicide inhibitors of a protein. Non-covalent molecular interactions important in the association of kinases with the compound include hydrogen bonding, ionic interactions, van der Waals, and hydrophobic interactions. Second, the compound must be able to assume a conformation and orientation in relation to the binding pocket, that allows it to associate with kinases. Although certain portions of the compound will not directly participate in this association with kinases, those portions may still influence the overall conformation of the molecule and may have a significant impact on potency. Conformational requirements include the overall three-dimensional structure and orientation of the chemical group or compound in relation to all or a portion of the binding pocket, or the spacing between functional groups of a compound comprising several chemical groups that directly interact with kinases.

Docking programs described herein, such as, for example, DOCK, or GOLD, are used to identify compounds that bind to the active site and/or binding pocket. Compounds may be screened against more than one binding pocket of the protein structure, or more than one set of coordinates for the same protein, taking into account different molecular dynamic conformations of the protein. Consensus scoring may then be used to identify the compounds that are the best fit for the protein (Charifson, P. S. et al., *J. Med. Chem.* 42: 5100-9 (1999)). Data obtained from more than one protein molecule structure may also be scored according to the methods described in Klingler et al., U.S. Utility application, filed May 3, 2002, entitled "Computer Systems and Methods for Virtual Screening of Compounds." Compounds having the best fit are then obtained from the producer of the chemical library, or synthesized, and used in binding assays and bioassays.

Computer modeling techniques may be used to assess the potential modulating or binding effect of a chemical compound on kinases. If computer modeling indicates a strong interaction, the molecule may then be synthesized and tested for its ability to bind to kinases and affect (by inhibiting or activating) its activity.

Modulating or other binding compounds of kinases may be computationally evaluated by means of a series of steps in which chemical groups or fragments are screened and selected for their ability to associate with the individual binding pockets or other areas of kinases. This process may begin by visual inspection of, for example, the active site on the computer screen based on the kinases coordinates. Selected fragments or chemical groups may then be positioned in a variety of orientations, or docked, within an individual binding pocket of kinases (Blaney, J. M. and Dixon, J. S., *Perspectives in Drug Discovery and Design,* 1:301, 1993). Manual docking may be accomplished using software such as Insight II (Accelrys, San Diego, Calif.) MOE (Chemical Computing Group, Inc., Montreal, Quebec, Canada); and SYBYL (Tripos, Inc., St. Louis, Mo., 1992), followed by energy minimization and/or molecular dynamics with standard molecular mechanics force fields, such as CHARMM (Brooks, et al., *J. Comp. Chem.* 4:187-217, 1983), AMBER (Weiner, et al., *J. Am. Chem. Soc.* 106: 765-84, 1984) and $C^2MMFF$ (Merck Molecular Force Field; Accelrys, San Diego, Calif.). More automated docking may be accomplished by using programs such as DOCK (Kuntz et al., *J. Mol. Biol.,* 161:269-88, 1982; DOCK is available from University of California, San Francisco, Calif.); AUTODOCK (Goodsell & Olsen, Proteins: Structure, Function, and Genetics 8:195-202, 1990; AUTODOCK is available from Scripps Research Institute, La Jolla, Calif.); GOLD (Cambridge Crystallographic Data Centre (CCDC); Jones et al., *J. Mol. Biol.* 245:43-53, 1995); and FLEXX (Tripos, St. Louis, Mo.; Rarey, M., et al., *J. Mol. Biol.* 261:470-89, 1996). Other appropriate programs are described in, for example, Halperin, et al.

During selection of compounds by the above methods, the efficiency with which that compound may bind to kinases may be tested and optimized by computational evaluation. For example, a compound that has been designed or selected to function as a kinases inhibitor may occupy a volume not overlapping the volume occupied by the active site residues when the native substrate is bound, however, those of ordinary skill in the art will recognize that there is some flexibility, allowing for rearrangement of the main chains and the side chains. In addition, one of ordinary skill may design compounds that could exploit protein rearrangement upon binding, such as, for example, resulting in an induced fit. An effective kinase inhibitor may demonstrate a relatively small difference in energy between its bound and free states (i.e., it must have a small deformation energy of binding and/or low conformational strain upon binding). Thus, the most efficient kinase inhibitors should, for example, be designed with a deformation energy of binding of not greater than 10 kcal/mol, not greater than 7 kcal/mol, not greater than 5 kcal/mol, or not greater than 2 kcal/mol. Kinase inhibitors may interact with the protein in more than one conformation that is similar in overall binding energy. In those cases, the deformation energy of binding is taken to be the difference between the energy of the free compound and the average energy of the conformations observed when the inhibitor binds to the enzyme.

Specific computer software is available in the art to evaluate compound deformation energy and electrostatic interaction. Examples of programs designed for such uses include: Gaussian 94, revision C (Frisch, Gaussian, Inc., Pittsburgh, Pa. ©1995); AMBER, version 7. (Kollman, University of California at San Francisco, ©2002); QUANTA/CHARMM (Accelrys, Inc., San Diego, Calif., ©1995); Insight II/Discover (Accelrys, Inc., San Diego, Calif., ©1995); DelPhi (Accelrys, Inc., San Diego, Calif., ©1995); and AMSOL (University of Minnesota) (Quantum Chemistry Program Exchange, Indiana University). These programs may be implemented, for instance, using a computer workstation, as are well known in the art, for example, a LINUX, SGI or Sun workstation. Other hardware systems and software packages will be known to those skilled in the art.

Those of ordinary skill in the art may express kinase protein using methods known in the art, and the methods disclosed herein. The native and mutated kinase polypeptides described herein may be chemically synthesized in whole or part using techniques that are well known in the art (see, e.g., Creighton, Proteins: Structures and Molecular Principles, W.H. Freeman & Co., NY, 1983).

Gene expression systems may be used for the synthesis of native and mutated polypeptides. Expression vectors containing the native or mutated polypeptide coding sequence and appropriate transcriptional/translational control signals, that are known to those skilled in the art may be constructed. These methods include in vitro recombinant DNA techniques, synthetic techniques and in vivo recombination/genetic recombination. See, for example, the techniques described in Sambrook et al., Molecular Cloning: A Laboratory Manual, Cold Spring Harbor Laboratory, NY, 2001, and Ausubel et al., Current Protocols in Molecular Biology, Greene Publishing Associates and Wiley Interscience, NY, 1989.

Host-expression vector systems may be used to express kinase. These include, but are not limited to, microorganisms such as bacteria transformed with recombinant bacteriophage DNA, plasmid DNA or cosmid DNA expression vectors containing the coding sequence; yeast transformed with recombinant yeast expression vectors containing the coding sequence; insect cell systems infected with recombinant virus expression vectors (e.g., baculovirus) containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence; or animal cell systems. The protein may also be expressed in human gene therapy systems, including, for example, expressing the protein to augment the amount of the protein in an individual, or to express an engineered therapeutic protein. The expression elements of these systems vary in their strength and specificities.

Specifically designed vectors allow the shuttling of DNA between hosts such as bacteria-yeast or bacteria-animal cells. An appropriately constructed expression vector may contain: an origin of replication for autonomous replication in host cells, one or more selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency.

The expression vector may also comprise various elements that affect transcription and translation, including, for example, constitutive and inducible promoters. These elements are often host and/or vector dependent. For example, when cloning in bacterial systems, inducible promoters such as the T7 promoter, pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, mammalian promoters (e.g., metallothionein promoter) or mammalian viral promoters, (e.g., adenovirus late promoter; vaccinia virus 7.5K promoter; SV40 promoter; bovine papilloma virus promoter; and Epstein-Barr virus promoter) may be used.

Various methods may be used to introduce the vector into host cells, for example, transformation, transfection, infection, protoplast fusion, and electroporation. The expression vector-containing cells are clonally propagated and individually analyzed to determine whether they produce the appropriate polypeptides. Various selection methods, including, for example, antibiotic resistance, may be used to identify host cells that have been transformed. Identification of polypeptide expressing host cell clones may be done by several means, including but not limited to immunological reactivity with anti-kinase antibodies, and the presence of host cell-associated activity.

Expression of cDNA may also be performed using in vitro produced synthetic mRNA. Synthetic mRNA can be efficiently translated in various cell-free systems, including but not limited to wheat germ extracts and reticulocyte extracts, as well as efficiently translated in cell-based systems, including, but not limited, to microinjection into frog oocytes.

To determine the cDNA sequence(s) that yields optimal levels of activity and/or protein, modified cDNA molecules are constructed. A non-limiting example of a modified cDNA is where the codon usage in the cDNA has been optimized for the host cell in which the cDNA will be expressed. Host cells are transformed with the cDNA molecules and the levels of kinase RNA and/or protein are measured.

Levels of kinase protein in host cells are quantitated by a variety of methods such as immunoaffinity and/or ligand affinity techniques, kinase-specific affinity beads or specific antibodies are used to isolate $^{35}$S-methionine labeled or unlabeled protein. Labeled or unlabeled protein is analyzed by SDS-PAGE. Unlabeled protein is detected by Western blotting, ELISA or RIA employing specific antibodies.

Following expression of kinase in a recombinant host cell, polypeptides may be recovered to provide the protein in active form. Several purification procedures are available and suitable for use. Recombinant kinase may be purified from cell lysates or from conditioned culture media, by various combinations of, or individual application of, fractionation, or chromatography steps that are known in the art.

In addition, recombinant kinase can be separated from other cellular proteins by use of an immuno-affinity column made with monoclonal or polyclonal antibodies specific for full length nascent protein or polypeptide fragments thereof. Other affinity based purification techniques known in the art may also be used.

Alternatively, the polypeptides may be recovered from a host cell in an unfolded, inactive form, e.g., from inclusion bodies of bacteria. Proteins recovered in this form may be solubilized using a denaturant, e.g., guanidinium hydrochloride, and then refolded into an active form using methods known to those skilled in the art, such as dialysis.

Cell Growth Assays

A variety of cell growth assays are known in the art and are useful in identifying pyrimidinyl-thiophene compounds (i.e. "test compounds") capable of inhibiting (e.g. reducing) cell growth and/or proliferation.

For example, a variety of cells are known to require specific kinases for growth and/or proliferation. The ability of such a cell to grow in the presence of a test compound may be assessed and compared to the growth in the absence of the test compound thereby identifying the anti-proliferative properties of the test compound. One common method of this type is to measure the degree of incorporation of label, such as tritiated thymidine, into the DNA of dividing cells. Alternatively, inhibition of cell proliferation may be assayed by determining the total metabolic activity of cells with a surrogate marker that correlates with cell number. Cells may be treated with a metabolic indicator in the presence and absence of the test compound. Viable cells metabolize the metabolic indicator thereby forming a detectable metabolic product. Where detectable metabolic product levels are decreased in the presence of the test compound relative to the absence of the test compound, inhibition of cell growth and/or proliferation is indicated. Exemplary metabolic indicators include, for example tetrazolium salts and AlamorBlue® (see Examples section below).

Pharmaceutical Compositions and Administration

In another aspect, the present invention provides a pharmaceutical composition including a pyrimidinyl-thiophene kinase modulator in admixture with a pharmaceutically acceptable excipient. One of skill in the art will recognize that the pharmaceutical compositions include the pharmaceutically acceptable salts of the pyrimidinyl-thiophene kinase modulators described above.

In therapeutic and/or diagnostic applications, the compounds of the invention can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A most preferable dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the invention may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a subject (e.g. patient) to be treated.

For nasal or inhalation delivery, the agents of the invention may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

The present invention is not to be limited in scope by the exemplified embodiments, which are intended as illustrations of single aspects of the invention. Indeed, various modifications of the invention in addition to those described herein will become apparent to those having skill in the art from the foregoing description. Such modifications are intended to fall within the scope of the invention. Moreover, any one or more features of any embodiment of the invention may be combined with any one or more other features of any other embodiment of the invention, without departing from the scope of the invention. For example, the pyrimidinyl-thiophene kinase modulators described in the Pyrimidinyl-thiophene Kinase Modulators section are equally applicable to the methods of treatment and methods of inhibiting kinases described herein. References cited throughout this application are examples of the level of skill in the art and are hereby incorporated by reference herein in their entirety for all purposes, whether previously specifically incorporated or not.

EXAMPLES

Example 1

Compound Preparation

Method 1:

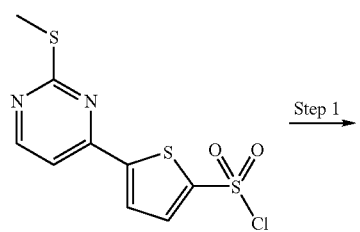

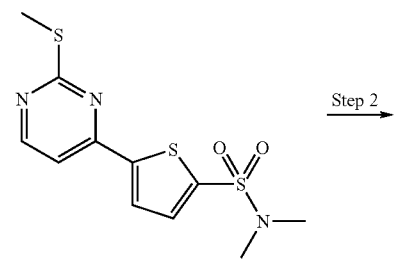

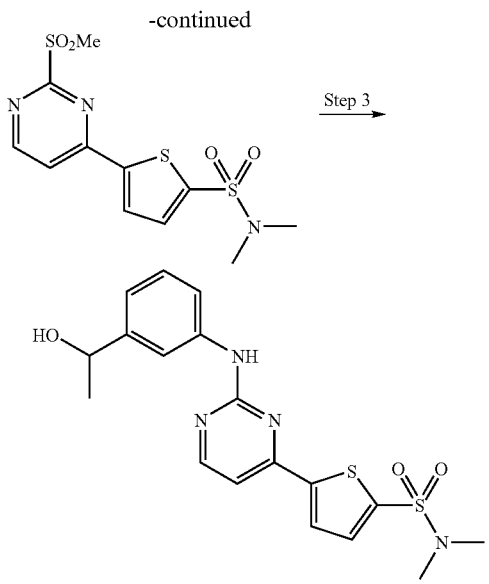

-continued

Step 1: Synthesis of 5-(2-methylsulfanyl-pyrimidin-4-yl)-thiophene-2-sulfonic acid dimethylamide A solution of 5-(2-methylsulfanyl-pyrimidin-4-yl)-thiophene-2-sulfonyl chloride (200 mg, 0.652 mmol) in 6 mL DCM was treated with pyridine (0.078 mL, 0.97 mmol) and 2 M dimethylamine/THF (0.485 mL, 0.97 mmol). The solution was stirred overnight. Additional 2 M dimethylamine/THF (0.400 mL, 0.8 mmol) was added and the reaction was stirred overnight. The mixture contained <5% starting material by LCMS. The mixture was washed 2× 1 N HCl, 1× brine and dried over $Na_2SO_4$. 5-(2-Methylsulfanyl-pyrimidin-4-yl)-thiophene-2-sulfonic acid dimethylamide (154 mg, 74.9%) was obtained as an off-white solid, >95% pure by LCMS. This material was taken to the next step. MS: m/z 316 (M+H$^+$).

Step 2: Synthesis of 5-(2-methanesulfonyl-pyrimidin-4-yl)-thiophene-2-sulfonic acid dimethylamide A solution of 5-(2-methylsulfanyl-pyrimidin-4-yl)-thiophene-2-sulfonic acid dimethylamide (154 mg, 0.488 mmol) dissolved in 2 mL $CH_2Cl_2$ was cooled in an ice water bath. A solution of m-CPBA (269 mg, 1.74 mmol) in 2.0 mL $CH_2Cl_2$ was added via addition funnel over ~2 min. After 30 minutes, the white slurry was removed from the ice bath. After 45 minutes at room temperature the mixture was washed with saturated aqueous $NaHCO_3$ (2×), brine (1×) and was dried over $Na_2SO_4$. The organic layer was concentrated in vacuo and the oil was triturated with $Et_2O$ to afford 5-(2-Methanesulfonyl-pyrimidin-4-yl)-thiophene-2-sulfonic acid dimethylamide (125.8 mg, 74.2%). The material was >95% pure by LCMS and was taken to the next step. MS: m/z 348 (M+H$^+$).

Step 3: Synthesis of 5-{2-[3-(1-hydroxyethyl)-phenylamino]-pyrimidin-4-yl}-thiophene-2-sulfonic acid dimethylamide 5-(2-Methanesulfonyl-pyrimidin-4-yl)-thiophene-2-sulfonic acid dimethylamide (19.8 mg, 0.057 mmol), 1-(3-aminophenyl)ethanol (11.7 mg, 0.085 mmol) and trifluoroacetic acid (6.5 uL, 0.085 mmol) were combined in DMSO (0.5 M) and the mixture was heated in a capped vial at 100° C. for 16 hours. The dark solution was diluted with DMSO and purified by preparative LC. 5-{2-[3-(1-Hydroxyethyl)-phenylamino]-pyrimidin-4-yl}-thiophene-2-sulfonic acid dimethylamide (14.4 mg, 62.6%) was obtained as a brown solid after lyophilization. $^1$H NMR (500 MHz, DMSO-d6) δ1.35 (d, J=6 Hz, 3H), 2.70 (s, 6H), 4.70 (m, 1H), 5.12 (d, J=4 Hz, 1H), 6.97 (br d, J=7 Hz, 1H), 7.24 (t, J=7.5 Hz, 1H), 7.46 (d, J=5.5 Hz, 1H), 7.49 (br d, J=6.5 Hz, 1H), 7.71 (d, J=4 Hz, 1H), 7.91 (br s, 1H), 8.12 (d, J=4 Hz, 1H), 8.58 (d, J=5.0 Hz, 1H), 9.75 (s, 1H). MS: m/z 405 (M+H$^+$).

TABLE 1

| Other compounds prepared by method 1: | |
|---|---|
| Structure | M + H |
|  | 458 |

TABLE 1-continued

Other compounds prepared by method 1:

| Structure | M + H |
|---|---|
| [structure] | 458 |
| [structure] | 474 |
| [structure] | 473 |

TABLE 1-continued

Other compounds prepared by method 1:

| Structure | M + H |
|---|---|
| (structure) | 473 |
| (structure) | 443 |
| (structure) | 489 |
| (structure) | 429 |

TABLE 1-continued

Other compounds prepared by method 1:

| Structure | M + H |
|---|---|
| 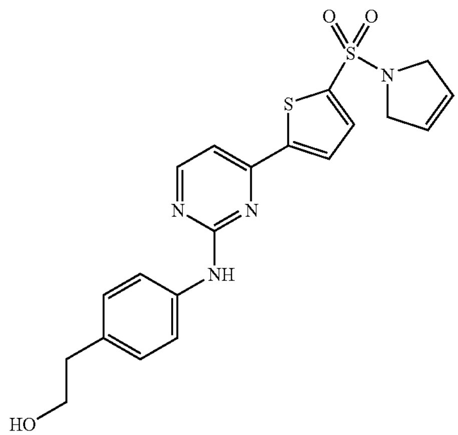 | 429 |
| 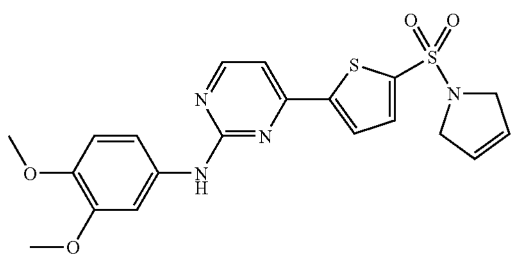 | 445 |
| 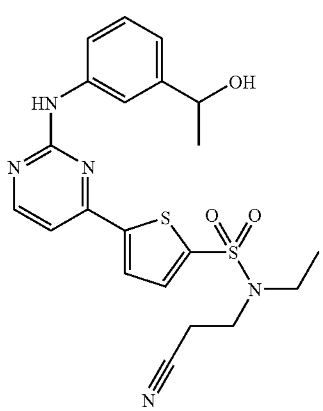 | 458 |
| 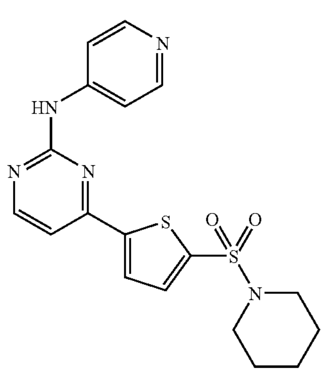 | 402 |

TABLE 1-continued

Other compounds prepared by method 1:

| Structure | M + H |
|---|---|
| 4-fluorophenyl-HN-pyrimidine-thiophene-sulfonyl-piperidine | 419 |
| 2-methylphenyl-HN-pyrimidine-thiophene-sulfonyl-piperidine | 415 |
| phenyl-HN-pyrimidine-thiophene-sulfonyl-piperidine | 401 |
| 4-bromophenyl-HN-pyrimidine-thiophene-sulfonyl-piperidine | 479 |

TABLE 1-continued

| Other compounds prepared by method 1: | |
|---|---|
| Structure | M + H |

| | 417 |
| | 437 |
| | 426 |
| | 433 |

TABLE 1-continued

| Other compounds prepared by method 1: | |
|---|---|
| Structure | M + H |
| (structure) | 437 |
| (structure) | 417 |
| (structure) | 431 |

TABLE 1-continued

Other compounds prepared by method 1:

| Structure | M + H |
|---|---|
| (structure: 3-(difluoromethoxy)phenyl-NH-pyrimidine-thiophene-sulfonyl-piperidine) | 467 |
| (structure: 2-methoxy-5-fluorophenyl-NH-pyrimidine-thiophene-sulfonyl-piperidine) | 449 |
| (structure: 1,3-dimethyl-1H-pyrazol-5-yl-NH-pyrimidine-thiophene-sulfonyl-piperidine) | 419 |

TABLE 1-continued

Other compounds prepared by method 1:

| Structure | M + H |
|---|---|
| 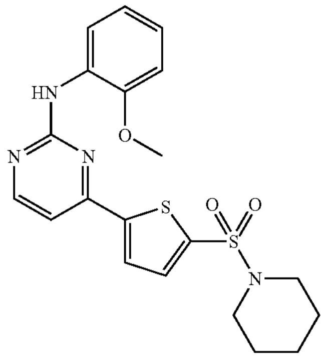 | 431 |
| 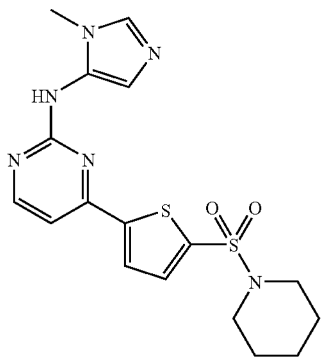 | 405 |
| 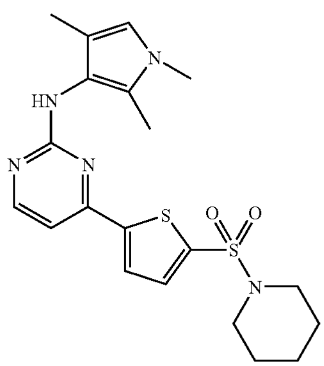 | 433 |
| 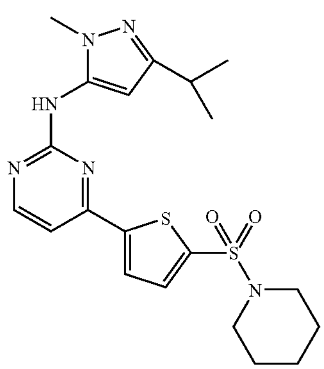 | 447 |

TABLE 1-continued

| Other compounds prepared by method 1: | |
|---|---|
| Structure | M + H |
| *(structure)* | 440 |
| *(structure)* | 445 |
| *(structure)* | 445 |

TABLE 1-continued

Other compounds prepared by method 1:

| Structure | M + H |
|---|---|
| 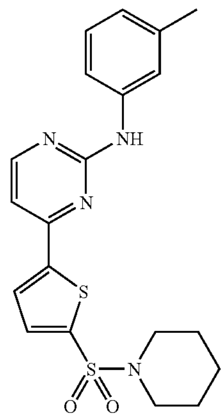 | 415 |
| 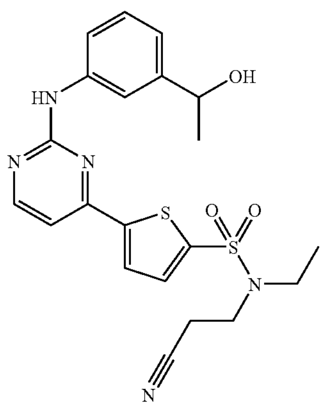 | 458 |
| 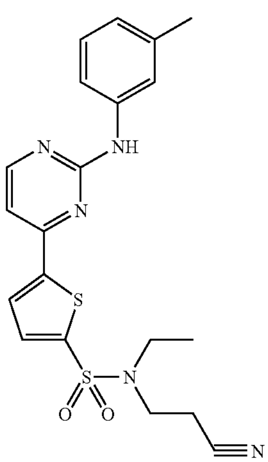 | 428 |

TABLE 1-continued

Other compounds prepared by method 1:

| Structure | M + H |
|---|---|
| (structure) | 458 |
| (structure) | 473 |
| (structure) | 405 |

TABLE 1-continued

| Other compounds prepared by method 1: | |
|---|---|
| Structure | M + H |
| (structure with 3,4-dihydroxyphenylamino-pyrimidine-thiophene-sulfonyl-piperidine) | 469 |
| (structure with 3-hydroxy-4-methylphenylamino-pyrimidine-thiophene-sulfonyl-piperidine) | 431 |
| (structure with 4-bromo-3-methylphenylamino-pyrimidine-thiophene-sulfonyl-piperidine) | 493 |
| (structure with 3-methoxyphenylamino-pyrimidine-thiophene-sulfonyl-piperidine) | 431 |

TABLE 1-continued

| Other compounds prepared by method 1: | |
|---|---|
| Structure | M + H |
| | 443 |
| | 441 |
| | 441 |
| | 460 |

71
TABLE 1-continued
Other compounds prepared by method 1:
| Structure | M + H |
|---|---|
| 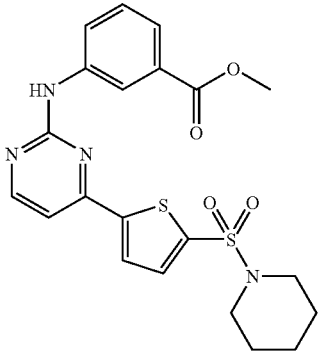 | 459 |
| 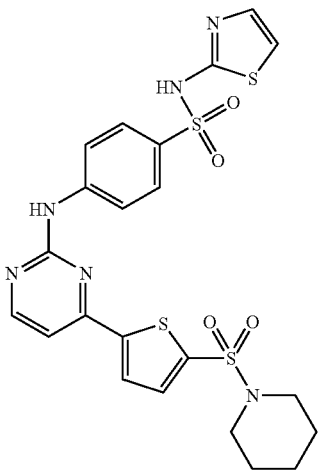 | 563 |
| 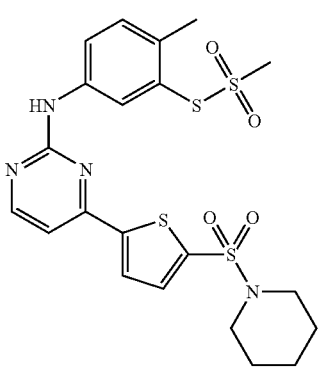 | 508 |

TABLE 1-continued

Other compounds prepared by method 1:

| Structure | M + H |
|---|---|
| 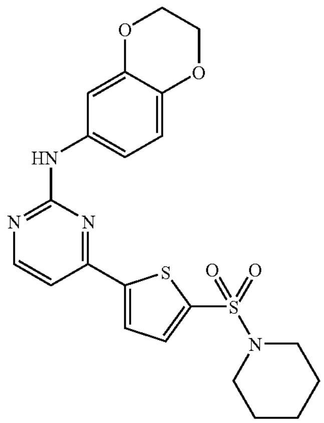 | 459 |
| 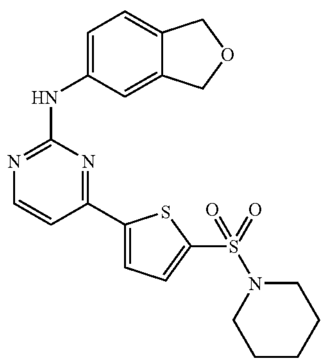 | 443 |
| 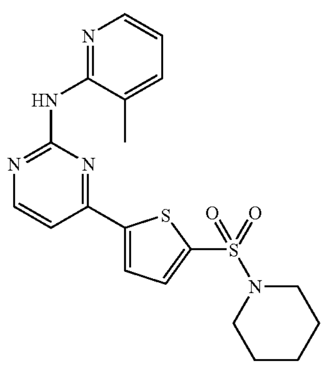 | 416 |
| 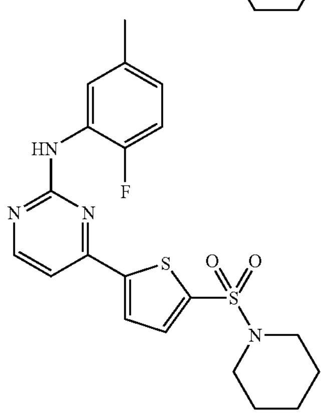 | 433 |

Method 2:

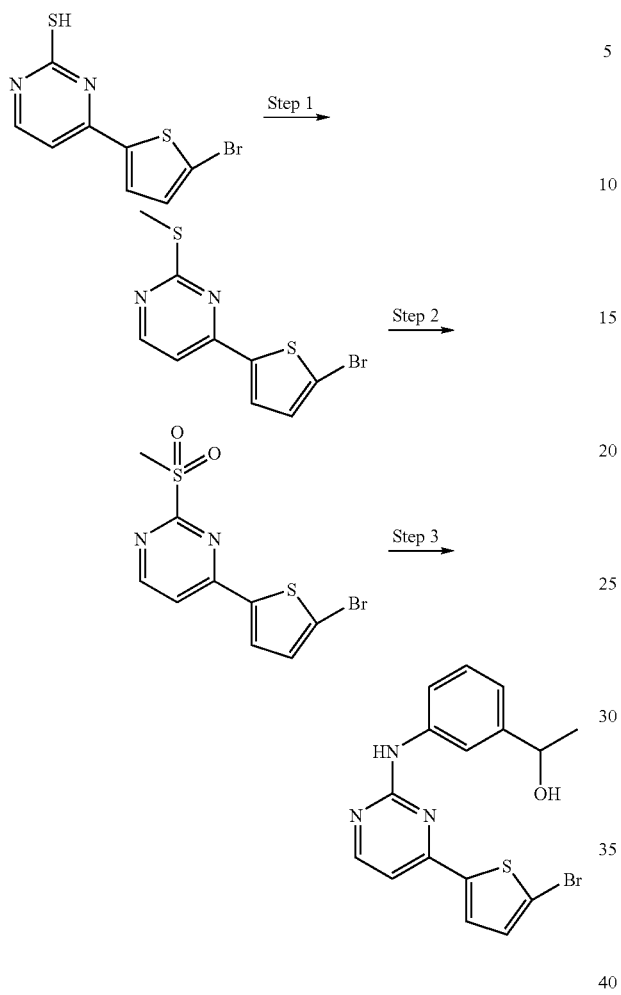

Step 1: Synthesis of 4-(5-bromothiophen-2-yl)-2-methylsulfanyl-pyrimidine 4-(5-Bromothiophen-2-yl)-pyrimidine thiol (2.5 g, 9.15 mmol) was completely dissolved in 14.8 mL DI water and 2.4 mL 4 N NaOH. The mixture was diluted with EtOH (25 mL) and MeI (0.598 mL, 9.61 mmol) was added. The reaction was stirred 18 hours. The yellow solids were collected by filtration, washed with EtOH and dried to afford 4-(5-Bromothiophen-2-yl)-2-methylsulfanyl-pyrimidine (2.32 g, 88.6%) as a pale yellow solid. MS: m/z 287 (M+H$^+$).

Step 2: Synthesis of 4-(5-bromothiophen-2-yl)-2-methylsulfonyl-pyrimidine 4-(5-Bromothiophen-2-yl)-2-methylsulfanyl-pyrimidine (2.32 g, 8.08 mmol) was dissolved in 40 mL DCM and cooled in an ice water bath. A solution of m-CPBA (4.88 g, 28.3 mmol) in DCM (40 mL) was added dropwise via addition funnel. After 1 hour, the mixture was filtered and the DCM was washed with saturated NaHCO$_3$ (2×) and brine (1×). The solution was dried over Na$_2$SO$_4$ and concentrated to dryness. The material was triturated with EtOAc to yield 4-(5-Bromothiophen-2-yl)-2-methylsulfonyl-pyrimidine a light yellow solid (999 mg, 38.7%). MS: m/z 319 (M+H$^+$).

Step 3: 1-{3-[4-(5-Bromothiophen-2-yl)pyrimidin-2-ylamino]-phenyl}-ethanol was Prepared According to the Procedure in Method 1, Step 3

$^1$H NMR (500 MHz, DMSO-d6) δ1.34 (d, J=6 Hz, 3H), 4.69 (q, J=6.5 Hz, 1H), 5.13 (br s, 1H), 6.95 (d, J=8 Hz, 1H), 7.22 (t, J=7.5 Hz, 1H), 7.31 (d, J=5 Hz, 1H) 7.36 (d, J=3.5 Hz, 1H), 7.56 (d, J=8 Hz, 1H), 7.80 (br t, H), 7.84 (d, J=4 Hz, 1H), 8.48 (d, J=5.5 Hz, 1H), 9.63 (s, 1H). MS: m/z 376 (M+H$^+$).

TABLE 2

Other compounds prepared by Method 2:

| Structure | M + H |
|---|---|
| 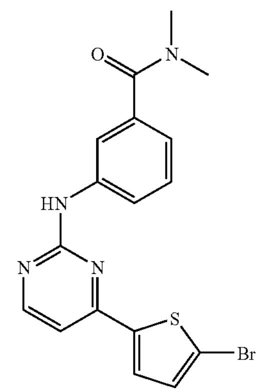 | 403/405 |
| 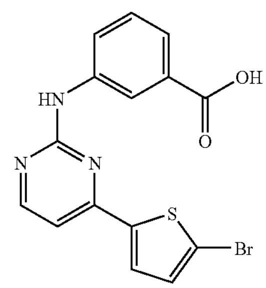 | 376/378 |
| 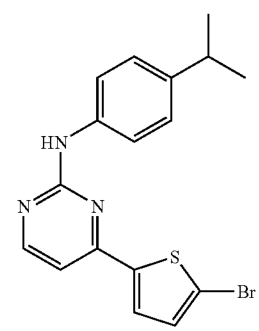 | 374/376 |
| 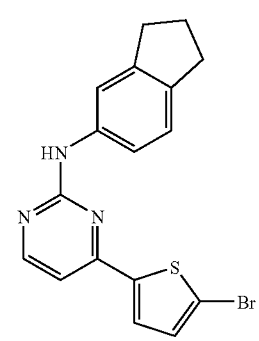 | 372/374 |

TABLE 2-continued

Other compounds prepared by Method 2:

| Structure | M + H |
|---|---|
| 4-methoxyphenyl-NH-pyrimidine-thiophene-Br | 362/364 |
| 3,5-dimethylphenyl-NH-pyrimidine-thiophene-Br | 360/362 |
| 3-methylthiophenyl-NH-pyrimidine-thiophene-Br | 378/380 |
| 3,4-dimethylphenyl-NH-pyrimidine-thiophene-Br | 360/362 |
| 3-methoxyphenyl-NH-pyrimidine-thiophene-Br | 362/364 |
| 3-methylphenyl-NH-pyrimidine-thiophene-Br | 346/348 |
| 4-methylphenyl-NH-pyrimidine-thiophene-Br | 346/348 |
| 3-bromophenyl-NH-pyrimidine-thiophene-Br | 410/413 |
| 3-cyanophenyl-NH-pyrimidine-thiophene-Br | 357/359 |
| 3-nitrophenyl-NH-pyrimidine-thiophene-Br | 377/379 |

TABLE 2-continued

Other compounds prepared by Method 2:

| Structure | M + H |
|---|---|
| (structure) | 376/378 |
| (structure) | 376/378 |
| (structure) | 481/483 |
| (structure) | 455/457 |
| (structure) | 445/447 |
| (structure) | 429/431 |
| (structure) | 474/476 |
| (structure) | 375/377 |

TABLE 2-continued

Other compounds prepared by Method 2:

| Structure | M + H |
|---|---|
| 4-[[4-(5-bromothiophen-2-yl)pyrimidin-2-yl]amino]benzamide | 375/377 |
| N-[4-[(dimethylamino)methyl]phenyl]-4-(5-bromothiophen-2-yl)pyrimidin-2-amine | 389/391 |
| N-[3-[(dimethylamino)methyl]phenyl]-4-(5-bromothiophen-2-yl)pyrimidin-2-amine | 389/391 |
| N-[3-(morpholin-4-ylmethyl)phenyl]-4-(5-bromothiophen-2-yl)pyrimidin-2-amine | 431/433 |
| N-(4-fluorophenyl)-4-(5-bromothiophen-2-yl)pyrimidin-2-amine | 350/352 |
| N-(3,4-dimethoxyphenyl)-4-(5-bromothiophen-2-yl)pyrimidin-2-amine | 392/394 |
| N-(3-isopropoxyphenyl)-4-(5-bromothiophen-2-yl)pyrimidin-2-amine | 390/392 |
| N-(2-methylbenzothiazol-5-yl)-4-(5-bromothiophen-2-yl)pyrimidin-2-amine | 403/405 |

TABLE 2-continued

Other compounds prepared by Method 2:

| Structure | M + H |
|---|---|
| (4-methoxy-3-hydroxyphenyl)amino pyrimidine with 5-bromothiophene | 378/380 |
| (benzo[d][1,3]dioxol-5-yl)amino pyrimidine with 5-bromothiophene | 376/378 |
| (1H-indol-5-yl)amino pyrimidine with 5-bromothiophene | 371/373 |
| (4-cyanophenyl)amino pyrimidine with 5-bromothiophene | 357/359 |
| (3-(methylsulfinyl)phenyl)amino pyrimidine with 5-bromothiophene | 394/396 |
| (4-(morpholinosulfonyl)phenyl)amino pyrimidine with 5-bromothiophene | 527/529 |

Method 3:

5-acetylthiophene-2-carboxylic acid →(Step 1)→ 5-(3-(dimethylamino)acryloyl)thiophene-2-carboxylic acid →(Step 2)→ 5-(2-((4-(2-hydroxyethyl)phenyl)amino)pyrimidin-4-yl)thiophene-2-carboxylic acid →(Step 3)→

-continued

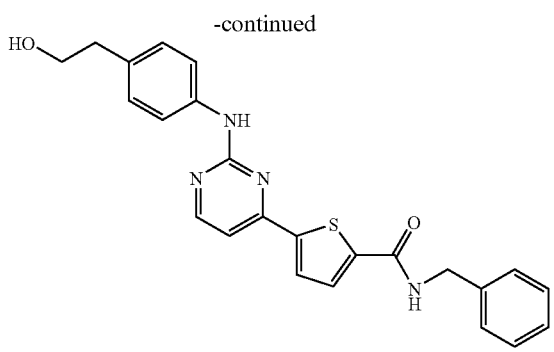

Step 1: Synthesis of 5-(3-dimethylamino-acryloyl)thiophene-2-carboxylic acid 5-Acetyl-thiophene-2-carboxylic acid (1 g, 5.87 mmol) was treated with N,N-dimethylformamide dimethylacetal (10 mL) and heated at 120° C. for 16 hours. The mixture was dried in vacuo to give 5-(3-dimethylamino-acryloyl)thiophene-2-carboxylic acid which was taken to the next step. MS: m/z 226 (M+H$^+$).

Step 2: Synthesis of 5-(2-m-tolylamino-pyrimidin-4-yl)thiophene-2-carboxylic acid 5-(3-dimethylamino-acryloyl)thiophene-2-carboxylic acid (200 mg, 0.888 mmol), N-m-tolylguanidine (71.1 mg, 1.77 mmol) and NaOH (264 mg, 1.77 mmol) were dissolved in 2-methoxyethanol (2 mL) and heated at 100° C. for 48 hours. After cooling, the reaction was diluted with 10% Aqueous citric acid solution and the solids were collected by filtration. The solids were washed with water and Et$_2$O and dried to afford 5-(2-m-tolylamino-pyrimidin-4-yl)thiophene-2-carboxylic acid (149 mg, 53.8%) as a yellow solid. MS: m/z 312 (M+H$^+$).

Step 3: Synthesis of 5-(2-m-tolylamino-pyrimin-4-yl)-thiophene-2-carboxylic acid benzylamide 5-(2-m-Tolylamino-pyrimidin-4-yl)thiophene-2-carboxylic acid (20 mg, 0.058 mmol), benzylamine (9.5 uL, 0.087 mmol), DIEA (30.3 uL, 0.174 mmol) and HATU (33 mg, 0.087 mmol) were combined in 0.5 mL DMA in a Smith microwave vial (0.2-5.0 mL) and the mixture was heated by microwaves at 90° C. for 900 s. The mixture was diluted to 1 mL with DMSO and purified by preparative HPLC. 5-(2-m-Tolylamino-pyrimin-4-yl)-thiophene-2-carboxylic acid benzylamide (14.7 mg, 59% yield) was obtained as a yellow fluffy solid after lyophilization $^1$H NMR (500 MHz, DMSO-d6) δ2.61 (t, J=7 Hz, 2H), 3.51 (m, 2H), 4.412 (d, J=6 Hz, 2H), 4.55 (t, J=5 Hz, 1H), 7.08, (d, J=9 Hz, 2H), 7.19 (m, 2H), 7.26-7.28 (m, 5H), 7.62 (d, J=9 Hz, 2H), 7.79 (d, J=4 Hz, 1H), 7.92 (d, J=4 Hz, 1H), 8.44 (d, J=5 Hz, 1H), 9.15 (t, 1H), 9.55 (s, 1H). MS: m/z 431 (M+H$^+$).

TABLE 3

| Other Compounds prepared by Method 3: | |
|---|---|
| Structure | M + H |
| (structure) | 422 |
| (structure) | 369 |

TABLE 3-continued

Other Compounds prepared by Method 3:

| Structure | M + H |
|---|---|
| 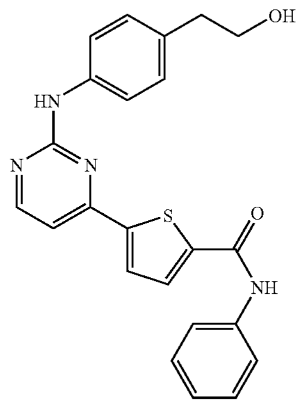 | 417 |
| 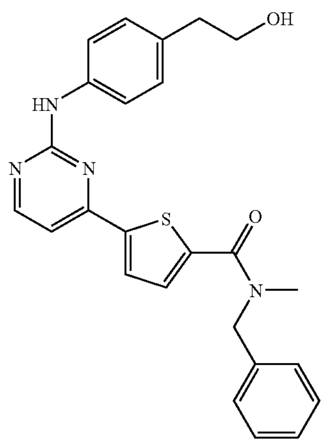 | 445 |
| 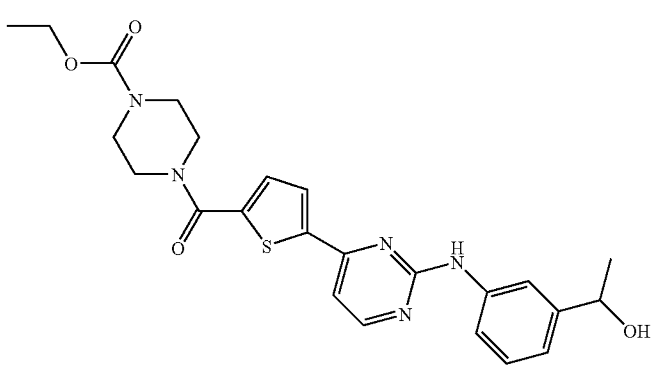 | 482 |

TABLE 3-continued

| Other Compounds prepared by Method 3: | |
|---|---|
| Structure | M + H |
| *structure* | 465 |
| *structure* | 383 |
| *structure* | 445 |

TABLE 3-continued

Other Compounds prepared by Method 3:

| Structure | M + H |
|---|---|
| (structure) | 451 |
| (structure) | 399 |
| (structure) | 397 |

TABLE 3-continued

Other Compounds prepared by Method 3:

| Structure | M + H |
|---|---|
| 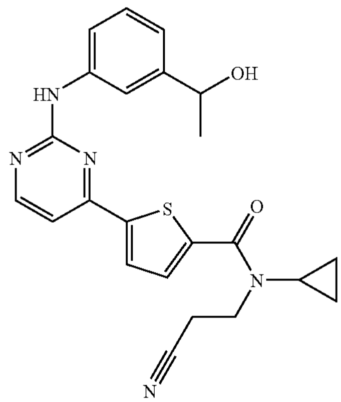 | 434 |
| 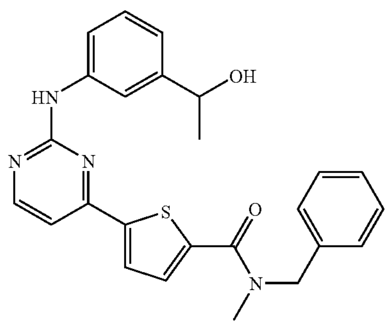 | 445 |
| 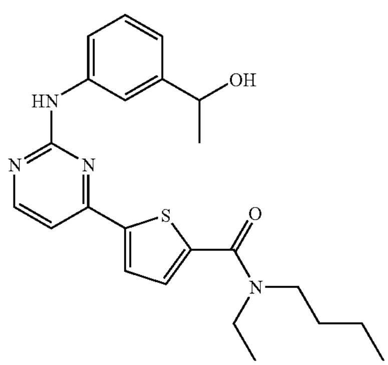 | 425 |
| 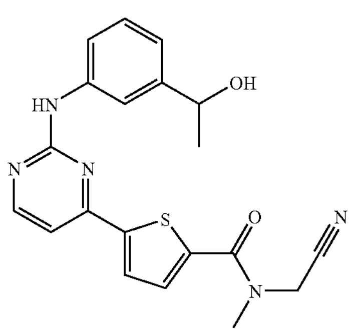 | 394 |

TABLE 3-continued

| Other Compounds prepared by Method 3: | |
|---|---|
| Structure | M + H |
| | 424.2 |
| | 422.2 |
| | 437 |
| | 369 |

TABLE 3-continued

Other Compounds prepared by Method 3:

| Structure | M + H |
|---|---|
| (structure) | 439 |
| (structure) | 397 |
| (structure) | 431 |
| (structure) | 479 |

TABLE 3-continued

| Other Compounds prepared by Method 3: | |
|---|---|
| Structure | M + H |
| *[structure: 2-((3-bromophenyl)amino)pyrimidin-4-yl thiophene-2-carboxamide with N-(furan-2-ylmethyl)]* | 455 |
| *[structure: 2-((3-(1-hydroxyethyl)phenyl)amino)pyrimidin-4-yl thiophene-2-carboxamide with N-(1-(naphthalen-2-yl)ethyl)]* | 495 |
| *[structure: 2-((3-(1-hydroxyethyl)phenyl)amino)pyrimidin-4-yl thiophene-2-carboxamide with N-(1-(naphthalen-1-yl)ethyl)]* | 495 |

TABLE 3-continued

Other Compounds prepared by Method 3:

| Structure | M + H |
|---|---|
| (structure) | 459 |
| (structure) | 452 |

TABLE 3-continued
Other Compounds prepared by Method 3:
| Structure | M + H |
|---|---|
| 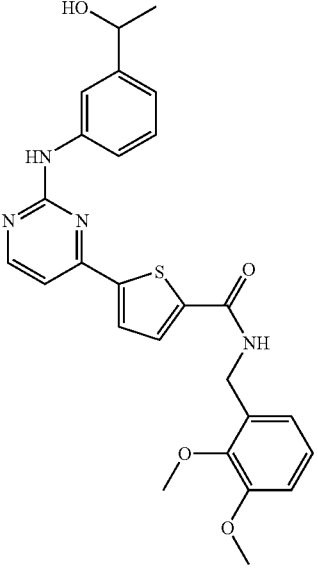 | 491 |
| 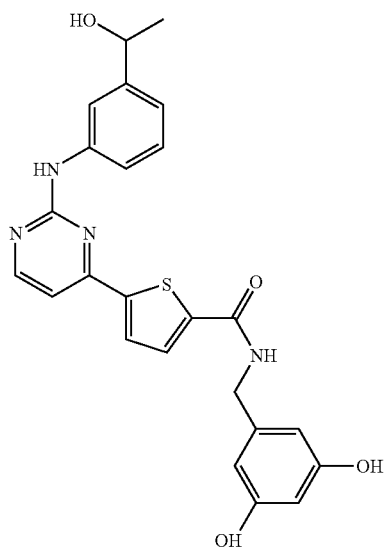 | 499 |

TABLE 3-continued
Other Compounds prepared by Method 3:
| Structure | M + H |
|---|---|
| 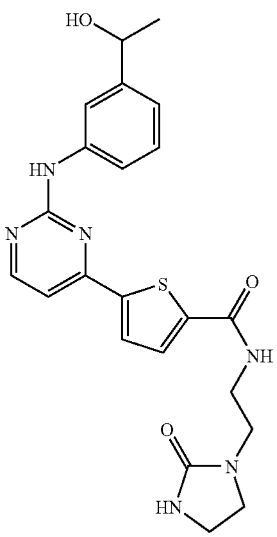 | 453 |
| 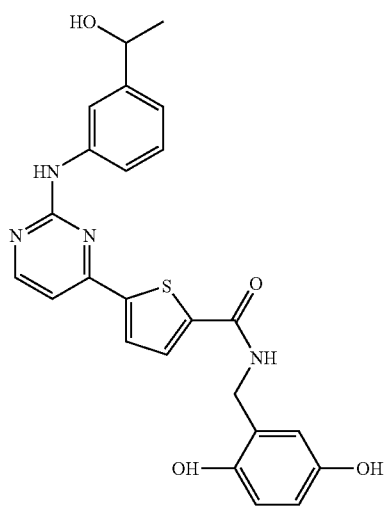 | 499 |

TABLE 3-continued

Other Compounds prepared by Method 3:

| Structure | M + H |
|---|---|
| (structure) | 445 |
| (structure) | 518 |
| (structure) | 445 |

TABLE 3-continued

Other Compounds prepared by Method 3:

| Structure | M + H |
|---|---|
| (structure) | 499 |
| (structure) | 437 |
| (structure) | 459 |
| (structure) | 471 |

TABLE 3-continued

Other Compounds prepared by Method 3:

| Structure | M + H |
|-----------|-------|
| 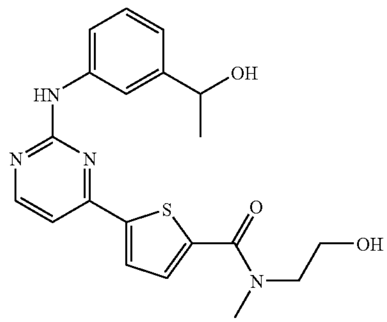 | 399 |
| 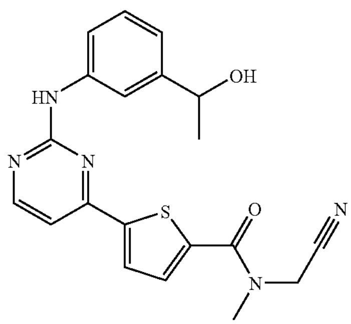 | 393 |
| 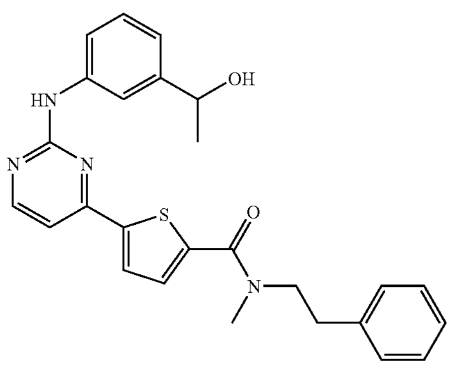 | 459 |
| 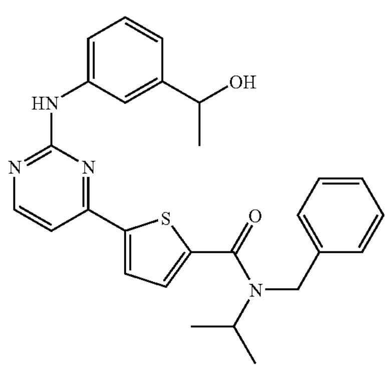 | 473 |

TABLE 3-continued

Other Compounds prepared by Method 3:

| Structure | M + H |
|---|---|
| 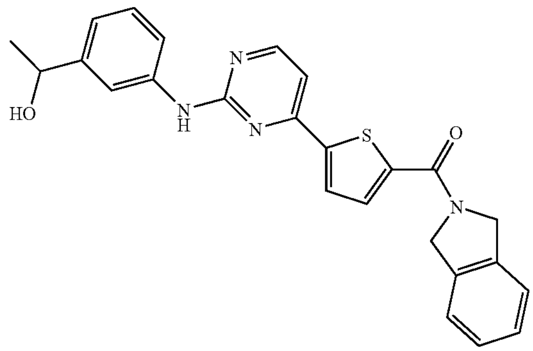 | 443 |
| 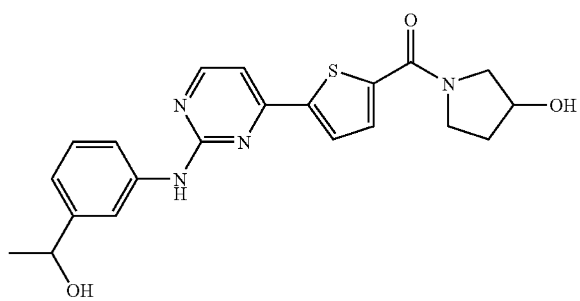 | 411 |
| 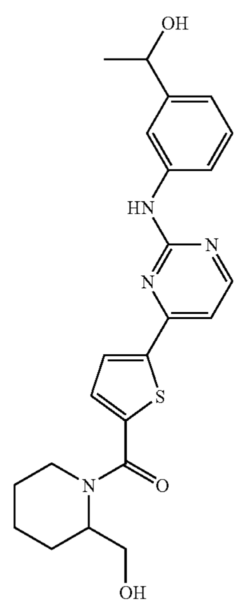 | 439 |

TABLE 3-continued
Other Compounds prepared by Method 3:
| Structure | M + H |
|---|---|
| 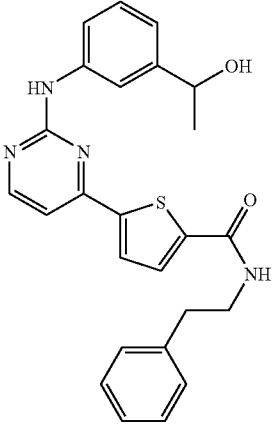 | 445 |
| 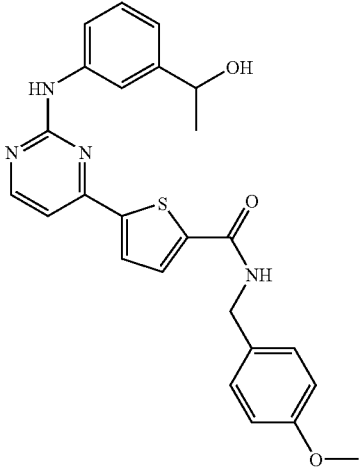 | 461 |
| 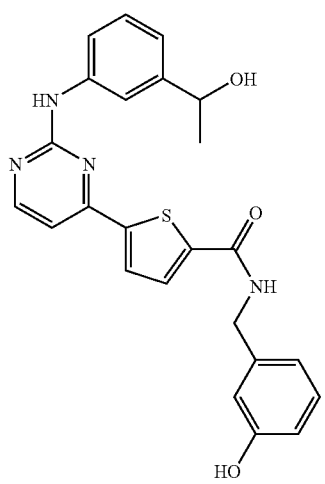 | 465 |

TABLE 3-continued

| Other Compounds prepared by Method 3: | |
|---|---|
| Structure | M + H |
| *(structure)* | 421 |
| *(structure)* | 425 |
| *(structure)* | 378.1 |

TABLE 3-continued

Other Compounds prepared by Method 3:

| Structure | M + H |
|---|---|
| (structure) | 465 |
| (structure) | 456 |
| (structure) | 425 |

TABLE 3-continued

| Other Compounds prepared by Method 3: | |
|---|---|
| Structure | M + H |
| | 475 |
| | 427 |
| | 461 |

TABLE 3-continued

Other Compounds prepared by Method 3:

| Structure | M + H |
|---|---|
| 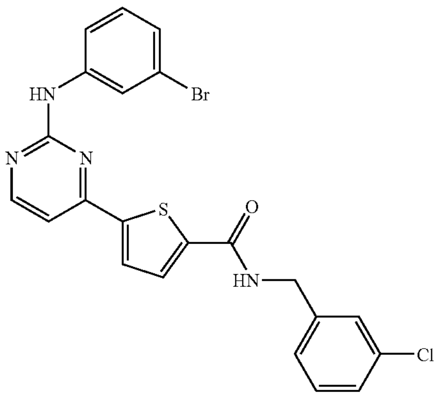 | 499 |
| 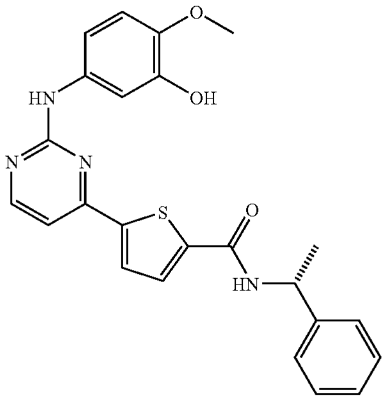 | 447 |
| 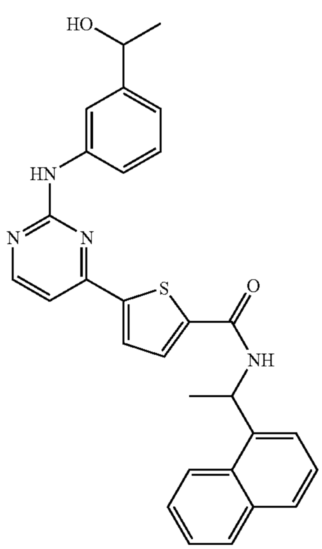 | 495 |

TABLE 3-continued
Other Compounds prepared by Method 3:
| Structure | M + H |
|---|---|
| 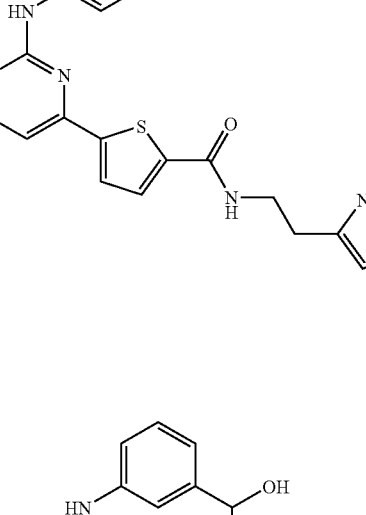 | 481 |
| 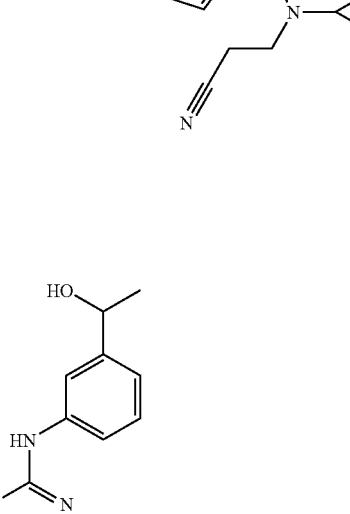 | 434 |
| 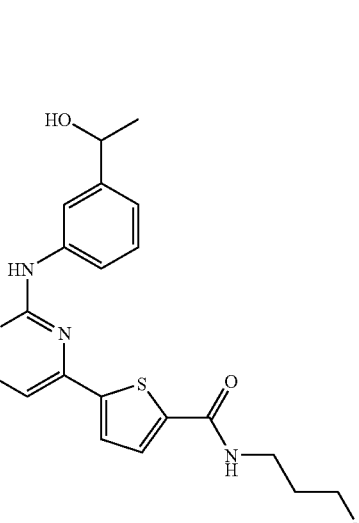 | 466 |

TABLE 3-continued

Other Compounds prepared by Method 3:

| Structure | M + H |
|---|---|
| 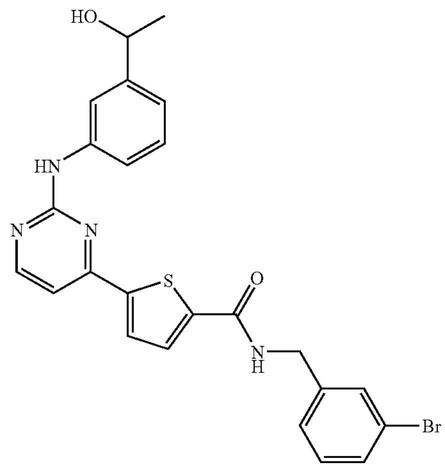 | 509 |
| 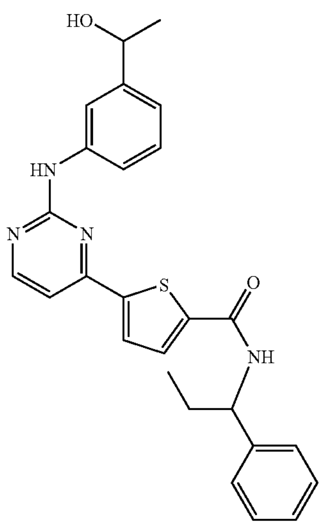 | 459 |
| 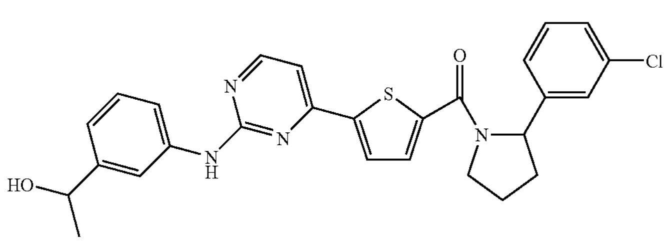 | 505 |

TABLE 3-continued

| Other Compounds prepared by Method 3: | |
|---|---|
| Structure | M + H |
| *(structure)* | 415 |
| *(structure)* | 481 |
| *(structure)* | 475 |

TABLE 3-continued
Other Compounds prepared by Method 3:
| Structure | M + H |
|---|---|
| 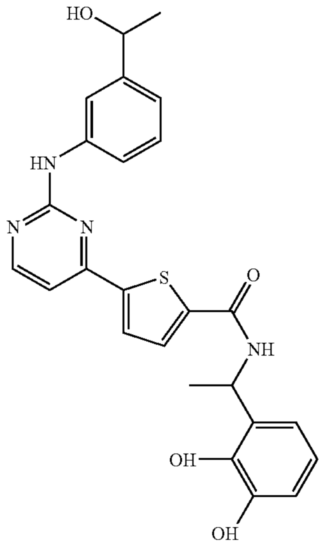 | 513 |
| 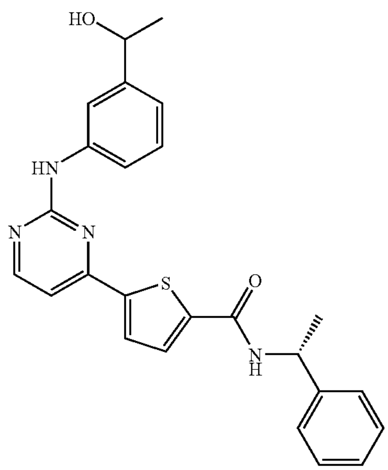 | 445 |
Method 4:
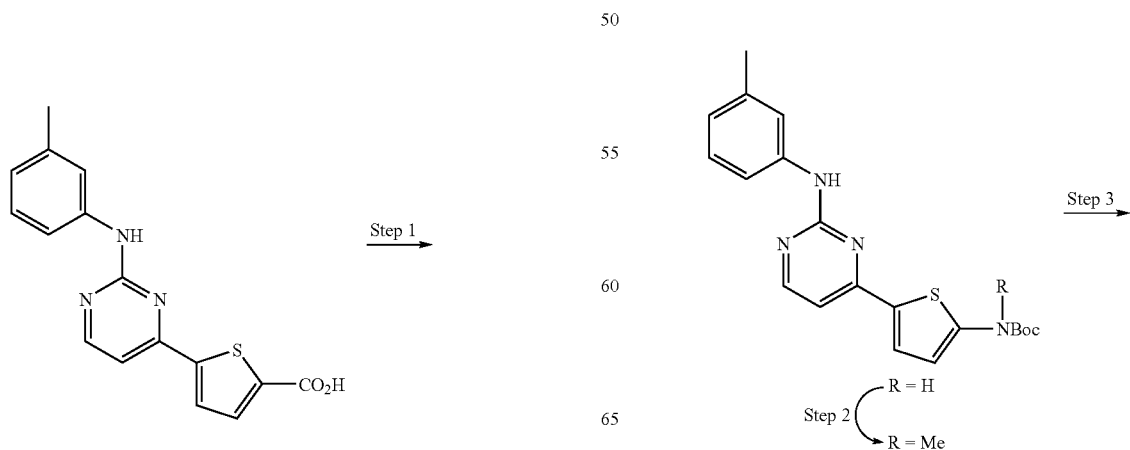

-continued

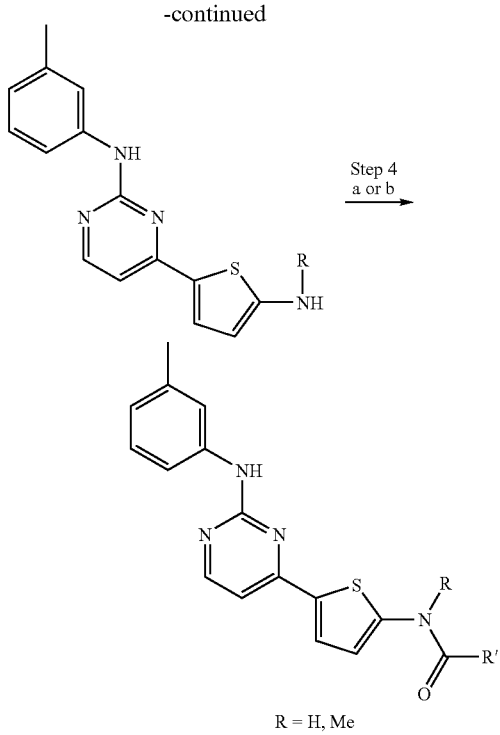

R = H, Me

Step 1: Synthesis of [5-(2-m-tolylamino-pyrimidin-4-yl)-thiophen-2-yl]-carbamic acid tert-butyl ester 5-(2-m-Tolylamino-pyrimidin-4-yl)thiophene-2-carboxylic acid (200 mg, 0.643 mmol) was treated with Diphenylphosphorylazide (277 uL, 1.28 mmol) and triethylamine (180 uL, 1.28 mmol) in t-BuOH (4 mL) for 7 hours at 100° C. The reaction was cooled to room temperature, concentrated in vacuo and purified by $SiO_2$ chromatography (0-50% B over 25 min.; Hexanes/EtOAc) to afford [5-(2-m-Tolylamino-pyrimidin-4-yl)-thiophen-2-yl]-carbamic acid tert-butyl ester (101.8 mg, 41.1%). $^1$H NMR (500 MHz, DMSO-d6) δ 1.49 (s, 9H), 2.32 (s, 3H), 6.57 (d, J=4 Hz, 1H), 6.75 (d, J=8 Hz, 1H), 7.13 (t, J=8 Hz, 1H), 7.14 (d, J=5 Hz, 1H), 7.47 (br m, 1H), 7.68 (d, J=4 Hz, 1H), 7.83 (br s, 1H), 8.32 (d, J=5 Hz, 1H), 9.42 (s, 1H), 10.8 (br s, 1H). MS: m/z 383 (M+H$^+$).

Step 2: Synthesis of methyl-[5-(2-m-tolylamino-pyrimidin-4-yl)-thiophen-2-yl]-carbamic acid tert-butyl ester Sodium hydride (60% disersion in mineral oil) (21.4 mg, 0.535 mmol) was added to a solution of [5-(2-m-tolylamino-pyrimidin-4-yl)-thiophen-2-yl]-carbamic acid tert-butyl ester (186 mg, 0.486 mmol) in anhydrous THF (5 mL) at ice bath temperature. After 15 minutes, MeI was added and the mixture was removed from the ice bath. Additional NaH (7.7 mg, 0.19 mmol) and MeI (9.0 uL, 0.145 mmol) were added after 5 hours and the reaction was stirred 3 days. The reaction was quenched by addition of a few drops of water and was concentrated to dryness and taken to the next step without further purification. MS: m/z 397 (M+H$^+$).

Step 3: Synthesis of [4-(5-aminothiophen-2-yl)-pyrimidin-2-yl]-m-tolyl-amine

[5-(2-m-Tolylamino-pyrimidin-4-yl)-thiophen-2-yl]-carbamic acid tert-butyl ester was treated with 4 N HCl in 1,4-dioxane for 6 hours or 20% TFA in DCM for 2 hours. The solution was dried in vacuo to afford [4-(5-aminothiophen-2-yl)-pyrimidin-2-yl]-m-tolyl-amine HCl salt. The amine salt was also neutralized by drying down the HCl/dioxane solution, redissolving in EtOAc and washing with saturated NaHCO$_3$ (2×) and brine (1×) and dried over Na$_2$SO$_4$. Concentrated and redissolved and dried down 2× from DCM to obtain an orange foam [4-(5-aminothiophen-2-yl)-pyrimidin-2-yl]-m-tolyl-amine (quantitative). MS: m/z 283 (M+H$^+$).

Step 4a: Synthesis of N-[5-(2-m-tolylamino-pyrimidin-4-yl)-thiophene-2-yl]-propionamide (R'=Et) (Acid Chloride Method)

A solution of propionyl chloride (4.85 uL, 0.055 mmol) in DCM (100 uL) was added dropwise to a DCM solution (400 uL) of [4-(5-aminothiophen-2-yl)-pyrimidin-2-yl]-m-tolyl-amine TFA salt (20 mg, 0.050 mmol), followed by addition of pyridine (8.9 uL, 0.11 mmol). After 16 hours, the reaction was diluted with DMSO and prep purified to afford N-[5-(2-m-tolylamino-pyrimidin-4-yl)-thiophene-2-yl]-propionamide (6.7 mg, 39.6%). The major impurity was the TFA amide. $^1$H NMR (500 MHz, DMSO-d6) δ1.11 (t, J=7 Hz, 3H), 2.33 (s, 3H), 2.38 (q, J=7 Hz, 2H), 6.69 (d, J=4 Hz, 1H), 6.75 (d, J=8 Hz, 1H), 7.12 (t, J=8 Hz, 1H), 7.18 (d, J=5.5 Hz, 1H), 7.50 (d, J=8 Hz, 1H), 7.72 (d, J=4 Hz, 1H), 7.81 (s, 1H), 8.33 (d, J=5.5 Hz, 1H), 9.44 (s, 1H), 11.38 (s, 1H). MS: m/z 339 (M+H$^+$).

Step 4b: Synthesis of N-[5-(2-m-tolylamino-pyrimidin-4-yl)-thiophene-2-yl]-benzamide (R'=Ph) (Carboxylic Acid Method)

Benzoic acid (5.2 mg, 0.042 mmol), [4-(5-aminothiophen-2-yl)-pyrimidin-2-yl]-m-tolyl-amine (10 mg, 0.035 mmol), DMAP (4.2 mg, 0.035 mmol) and HATU (15.9 mg, 0.042 mmol) were combined in 400 uL DMF and the solution was heated on a hot plate in a capped vial at 70° C. After 16 hours, the mixture was diluted with DMSO and prep purified to afford N-[5-(2-m-tolylamino-pyrimidin-4-yl)-thiophene-2-yl]-benzamide (3.0 mg, 22%). $^1$H NMR (500 MHz, DMSO-d6) δ1.29 (s, 3H), 6.70 (d, J=7.5 Hz, 1H), 6.93 (d, J=4 Hz, 1H), 7.10 (t, J=8 Hz, 1H), 7.16 (d, J=5.5 Hz, 1H), 7.47 (d, J=7.5 Hz, 1H), 7.51 (m, 2H), 7.58 (m, 1H), 7.74 (d, J=4 Hz, 1H), 7.78 (s, 1H), 7.95 (m, 2H), 8.31 (d, J=5.5 Hz, 1H), 9.42 (s, 1H). MS: m/z 387 (M+H$^+$).

Method 5:

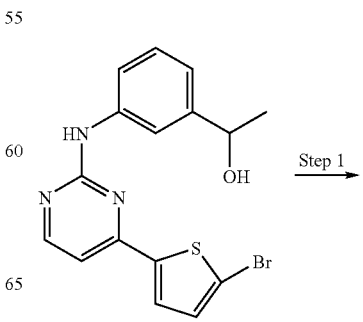

-continued

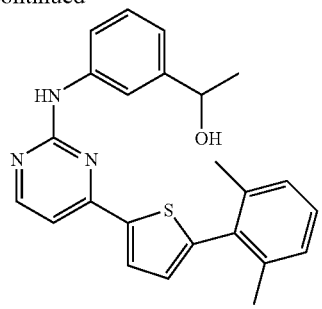

Step 1: Synthesis of 1-(3-{4-[5-(2,6-dimethylphenyl)-thiophen-2-yl]-pyrimidin-2-ylamino}-phenylethanol 1-{3-[4-(5-Bromothiophen-2-yl)pyrimidin-2-ylamino]-phenyl}-ethanol (15 mg, 0.04 mmol), 2,6-dimethylphenylboronic acid (7.2 mg, 0.048 mmol) and $PdCl_2(dppf)_2$ (1.6 mg, 0.002 mmol) were combined in Smith microwave vial (0.2-5.0 mL) in degassed DMA (300 uL) and 2 M $Na_2CO_3$ (250 uL). The mixture was micro waved at 165° C. for 900 s. The mixture was diluted with 500 uL DMSO and purified directly by preparative HPLC to afford 1-(3-{4-[5-(2,6-dimethylphenyl)-thiophen-2-yl]-pyrimidin-2-ylamino}-phenylethanol (4.9 mg, 30% yield). $^1$H NMR (500 MHz, DMSO-d6) δ1.29 (d, J=6.5 Hz, 3H), 2.14 (s, 6H), 4.64 (m, 1H), 5.07 (d, J=3.5 Hz, 1H), 6.91 (d, J=8 Hz, 1H), 7.02 (d, J=4 Hz, 1H), 7.16-7.25 (m, 4H), 7.35 (d, J=5 Hz, 1H), 7.60 (d, J=8 Hz, 1H), 7.84 (br t, 1H), 8.03 (d, J=3.5 Hz, 1H), 8.48 (d, J=5 Hz, 1H), 9.58 (s, 1H). MS: m/z 402 (M+H$^+$).

TABLE 4

Other compounds prepared by method 5:

| Structure | M + H |
|---|---|
|  | 402 |
|  | 402 |
|  | 402 |

TABLE 4-continued

Other compounds prepared by method 5:

| Structure | M + H |
|---|---|
| (morpholinomethyl-phenyl-NH-pyrimidine-thiophene-ethylphenyl) | 457 |
| (4-methylpiperazine-carbonyl-phenyl-NH-pyrimidine-thiophene-ethylphenyl) | 484 |
| (N,N-dimethylbenzamide-phenyl-NH-pyrimidine-thiophene-ethylphenyl) | 429 |
| (dimethylaminoethyl-NH-C(O)-phenyl-NH-pyrimidine-thiophene-dimethylphenyl) | 472 |
| (dimethylaminoethyl-piperazine-C(O)-phenyl-NH-pyrimidine-thiophene-ethylphenyl) | 541 |

TABLE 4-continued
| Other compounds prepared by method 5: | |
|---|---|
| Structure | M + H |
| 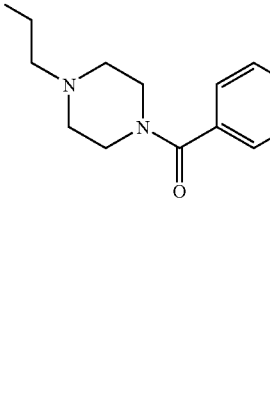 | 541 |
| 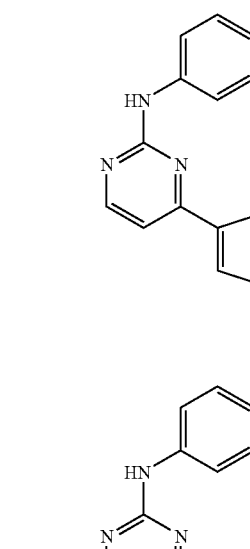 | 418 |
| 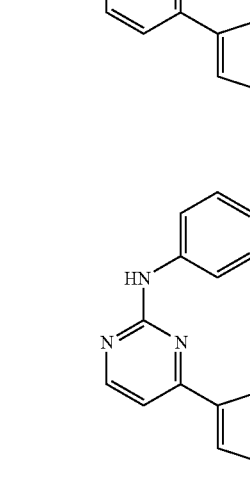 | 402 |
| | 402 |

TABLE 4-continued

| Other compounds prepared by method 5: | |
|---|---|
| Structure | M + H |
| *structure* | 404 |
| *structure* | 442 |
| *structure* | 442 |
| *structure* | 404 |
| *structure* | 413 |

TABLE 4-continued

| Other compounds prepared by method 5: | |
|---|---|
| Structure | M + H |
| | 452 |
| | 507 |
| | 413 |
| | 418 |

TABLE 4-continued

| Other compounds prepared by method 5: | |
|---|---|
| Structure | M + H |
| *(structure)* | 432 |
| *(structure)* | 487 |
| *(structure)* | 431 |
| *(structure)* | 450 |

TABLE 4-continued

Other compounds prepared by method 5:

| Structure | M + H |
|---|---|
| 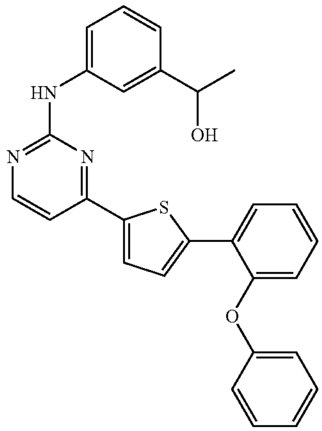 | 466 |
| 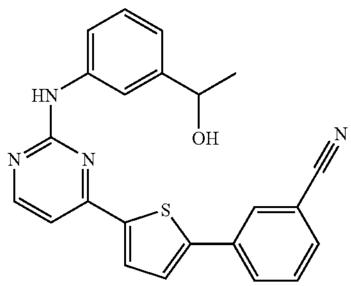 | 399 |
| 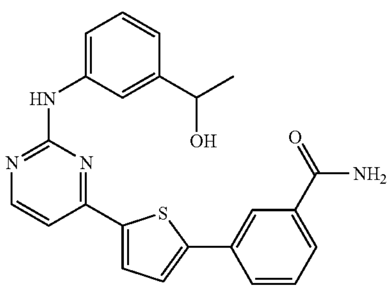 | 417 |
| 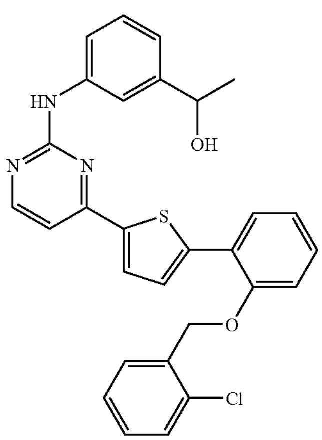 | 514 |

TABLE 4-continued
Other compounds prepared by method 5:
| Structure | M + H |
|---|---|
| | 408 |
| 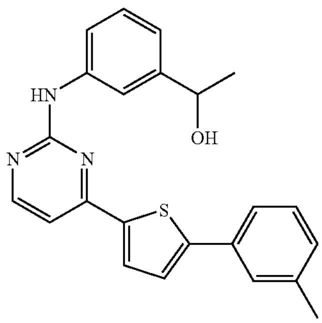 | 388 |
| | 408 |
Method 6:
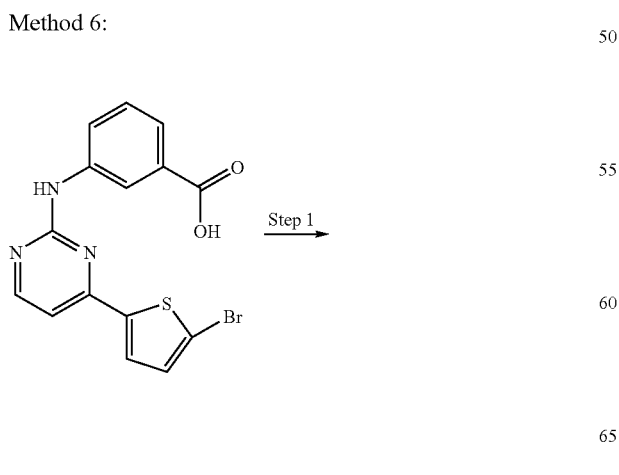
Step 1
-continued
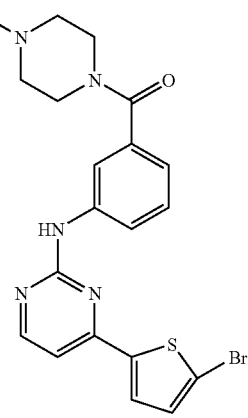

Step 1: Synthesis of {3-[4-(5-bromo-thiophen-2yl)-pyrimidin-2-ylamino}-phenyl}-(4-methyl-piperazin-1-yl)methanone 3-[4-(5-Bromo-thiophen-2-ylamino]-benzoic acid (20 mg, 0.048 mmol), prepared using method 2 (step 3) and 3-aminobenzoate, was combined with N-methylpiperazine (8.1 uL, 0.073 mmol), DIEA (29.2 uL, 0.168 mmol) and HATU (27.7 mg, 0.073 mmol) in a Smith microwave vial (0.2-5.0 mL) in 0.5 mL DMA. The mixture was micro waved at 90° C. for 900 s. The solution was diluted with 0.5 mL DMSO and purified by preparative HPLC to afford {3-[4-(5-Bromo-thiophen-2yl)-pyrimidin-2-ylamino}-phenyl}-(4-methyl-piperazin-1-yl)methanone (17.8 mg, 79.1%) after lyophilization. MS: m/z 458 (M+H$^+$).

TABLE 5

| Other Compounds prepared by method 6: | |
|---|---|
| Structure | M + H |
| | 445/447 |
| | 492/494 |

TABLE 5-continued

| Other Compounds prepared by method 6: | |
|---|---|
| Structure | M + H |
| | 403/405 |
| | 515/517 |
| | 462464 |
| | 419/421 |

TABLE 5-continued
Other Compounds prepared by method 6:
| Structure | M + H |
|---|---|
| 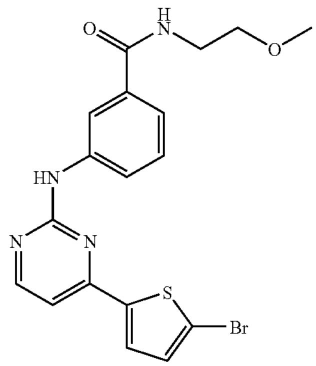 | 433/435 |
| 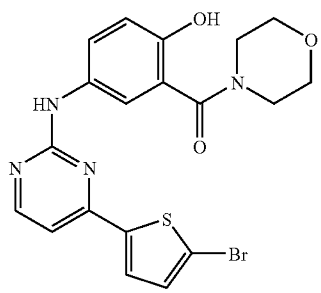 | 461/463 |
| 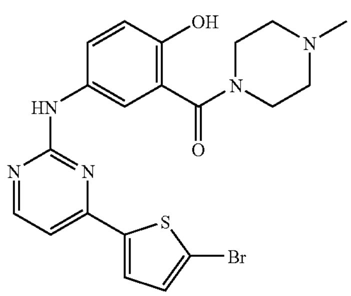 | 474/476 |
| 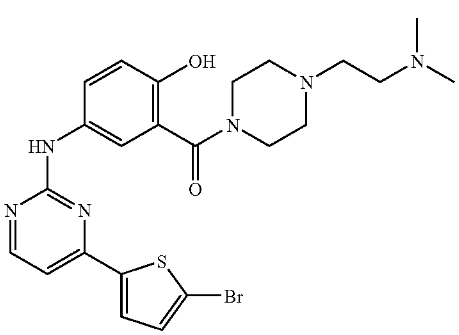 | 531/533 |
| | 504/506 |
| | 419/421 |
| | 488/490 |
Method 7:
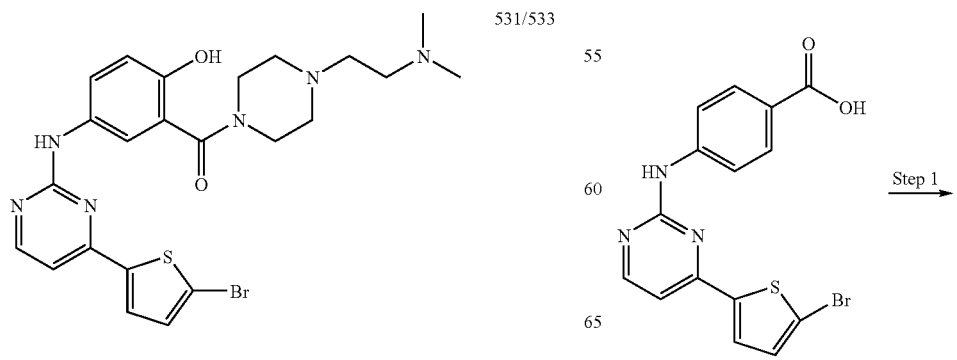

-continued

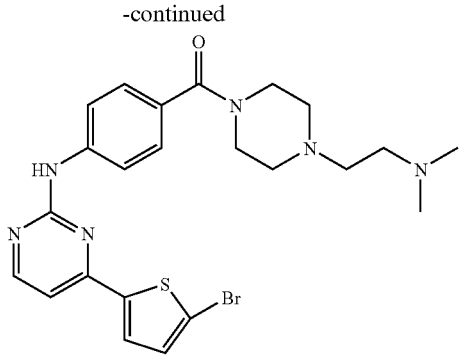

Step 1: Synthesis of (4-(4-(5-bromothiophen-2-yl)pyrimidin-2-ylamino)phenyl)(4-(2-(dimethylamino)ethyl)piperazin-1-yl)methanone 4-[4-(5-Bromo-thiophen-2-ylamino]-benzoic acid (30 mg, 0.080 mmol) (see method 2, step 3) was combined with N,N-dimethyl-2-(piperazin-1-yl)ethanamine (12.5 mg, 0.080 mmol), DIEA (20.6 mg, 0.16 mmol) and HATU (30.3 mg, 0.080 mmol) in DMF (0.5 mL) in a Smith microwave vial (0.2-5.0 mL). The mixture was irradiated at 90° C. for 1800 s. The reaction mixture was then diluted with saturated NaHCO$_3$ and extracted with ethyl acetate. The organic layers were combined, dried over sodium sulfate, filtered and concentrated to dryness. The crude product was then purified by silica gel chromatography to afford (4-(4-(5-bromothiophen-2-yl)pyrimidin-2-ylamino)phenyl)(4-(2-(dimethylamino)ethyl)piperazin-1-yl)methanone (25.9 mg, 63% yield) as a light yellow solid. $^1$H NMR (500 MHz, CD$_3$OD) δ2.27 (s, 6H), 2.53 (m, 8H), 3.60 (br, 2H), 3.75 (br, 2H), 7.15 (d, J=5.5 Hz, 1H), 7.16 (d, J=4.0 Hz, 1H), 7.40 (d, J=9.0 Hz, 2H), 7.61 (d, J=4.0 Hz, 1H), 7.84 (d, J=9.0 Hz, 2H), 8.40 (d, J=5.5 Hz, 1H). MS: m/z 515.1/517.1 (M+H$^+$).

TABLE 6

Other compounds prepared by method 7:

| Structure | M + H | Structure | M + H |
|---|---|---|---|
| 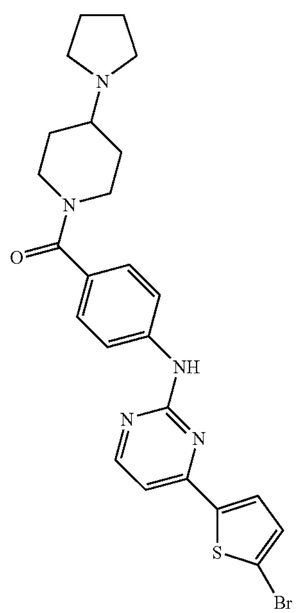 | 512/514 | 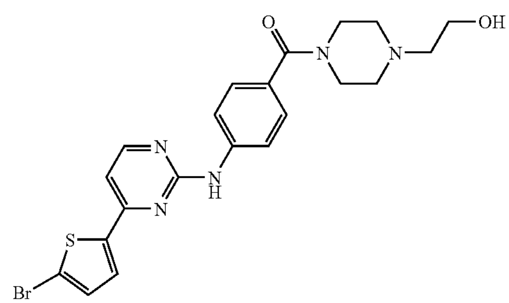 | 488/490 |
| 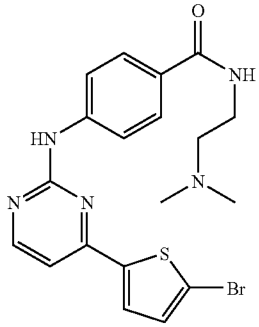 | 446/448 | 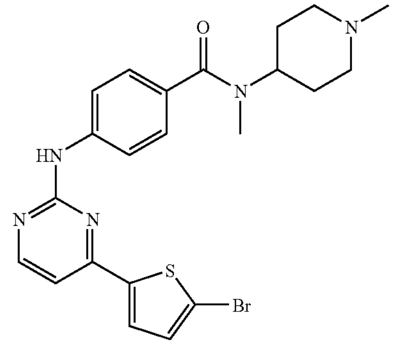 | 486/488 |

TABLE 6-continued
Other compounds prepared by method 7:
| Structure | M + H | Structure | M + H |
|---|---|---|---|
| 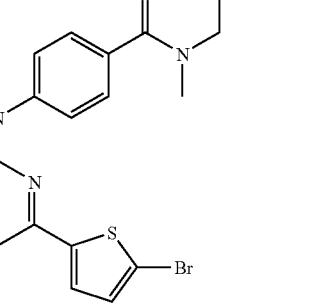 | 494/496 | 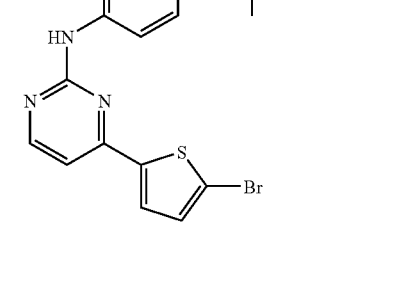 | 472/474 |
| 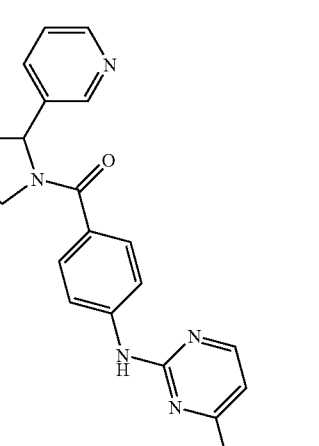 | 506/508 | 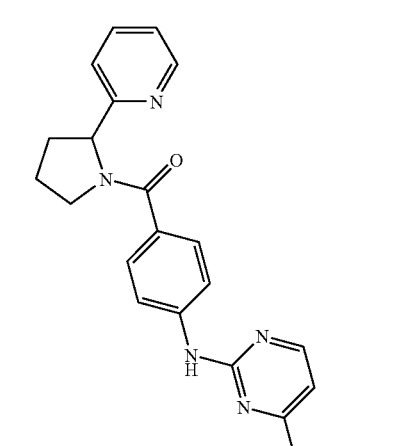 | 506/508 |
| 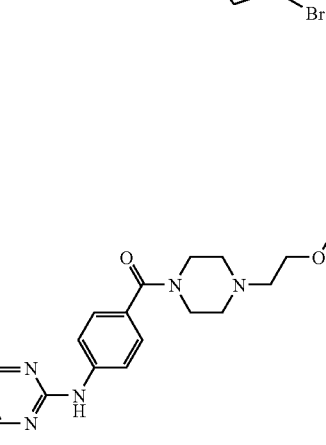 | 532/534 | 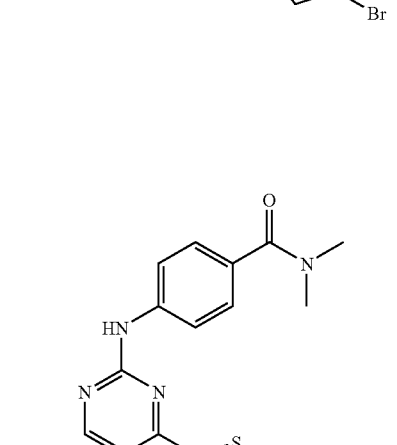 | 403/405 |

TABLE 6-continued

Other compounds prepared by method 7:

| Structure | M + H | Structure | M + H |
|---|---|---|---|
| | 458/460 | | 526/528 |
| | 419/521 | | 472/474 |

TABLE 6-continued

Other compounds prepared by method 7:

| Structure | M + H | Structure | M + H |
|---|---|---|---|
| 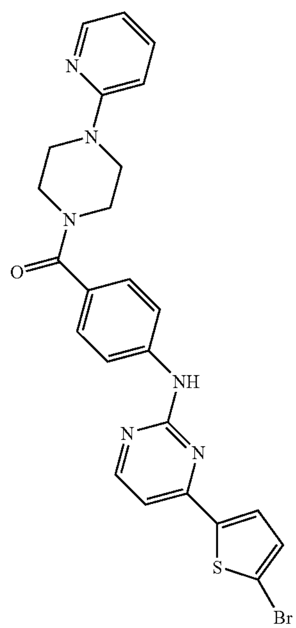 | 521/523 | 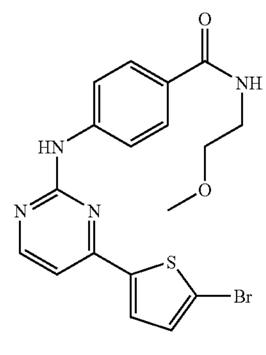 | 433/435 |
| 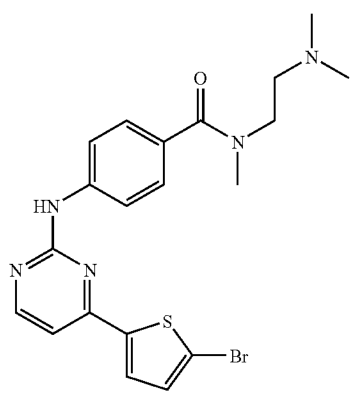 | 460/462 | 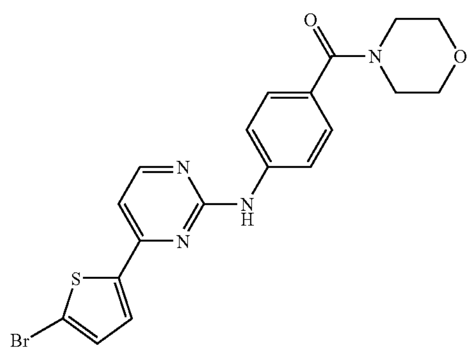 | 445/447 |
| 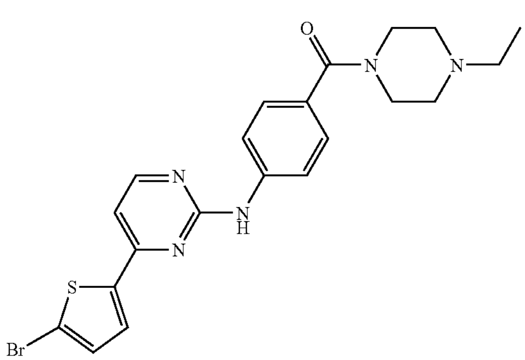 | 472/474 | 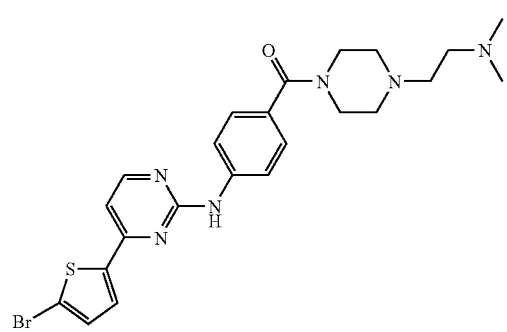 | 515/517 |

TABLE 6-continued
Other compounds prepared by method 7:
| Structure | M + H | Structure | M + H |
|---|---|---|---|
| 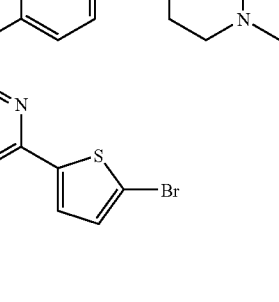 | 518/520 | 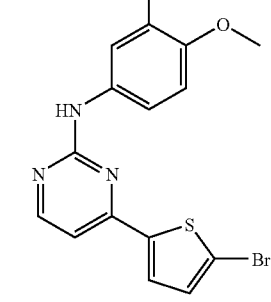 | 518/520 |
| 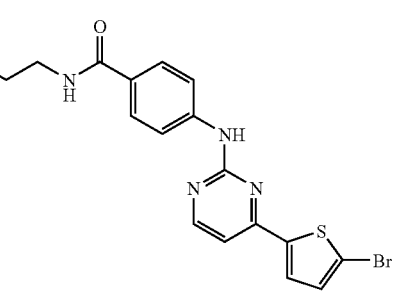 | 446/448 | 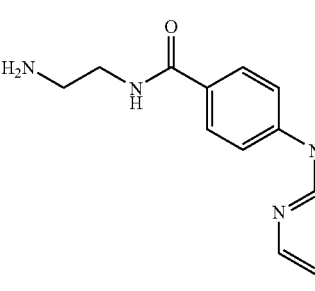 | 418/420 |
| 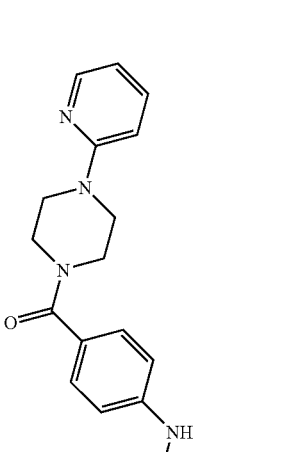 | 521/523 | 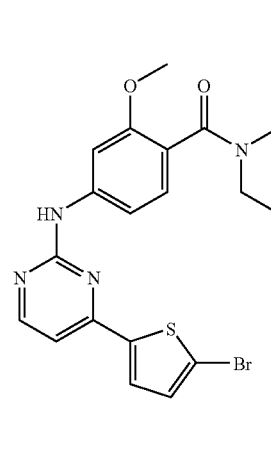 | 518/520 |

TABLE 6-continued

| Other compounds prepared by method 7: Structure | M + H | Structure | M + H |
|---|---|---|---|
| | 403/405 | | 460/462 |
| | 432/434 | | |

Method 8:

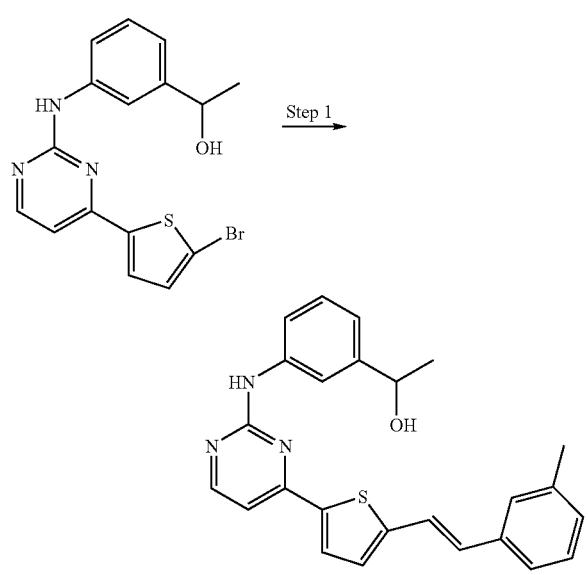

Step 1: Synthesis of 1-(3-{4-[5-(2-m-tolyl-vinyl)-thiophen-2-yl]-pyrimidin-2-ylamino}-phenyl)-ethanol 1-{3-[4-(5-Bromothiophen-2-yl)pyrimidin-2-ylamino]-phenyl}-ethanol (20 mg, 0.056 mmol), 3-methylstyrene (22 uL, 0.168 mmol), FibreCat 1001 (12 mg, 0.0056 mmol), and NaOAc (9.2 mg, 0.112 mmol) were combined in degassed DMF (0.5 mL) in an 8-mL glass vial. The reaction was heated at 100° C. for 18 hours. The mixture was diluted with DMSO, filtered and purified by preparative LCMS to afford 1-(3-{4-[5-(2-m-tolyl-vinyl)-thiophen-2-yl]-pyrimidin-2-ylamino}-phenyl)-ethanol (1.0 mg, 4.3%). $^1$H NMR (500 MHz, DMSO-d6) δ1.35 (d, J=6 Hz, 3H), 2.27 (s, 3H), 4.68 (q, J=6 Hz, 1H), 5.12 (br s, 1H), 6.90 (d, J=7.5 Hz, 1H), 6.98 (d, J=16.5 Hz, 1H), 7.05 (d, J=7.5 Hz, 1H), 7.18-7.26 (m, 3H), 7.32 (d, J=8 Hz, 1H), 7.38 (Br s, 1H), 7.41 (d, J=16 Hz, 1H), 7.50 (dd, J=1.5 Hz, J=8.5 Hz, 1H), 7.87 (d, J=4 Hz, 1H), 7.92 (br s, 1H), 8.34 (s, 1H), 8.40 (d, J=5 Hz, 1H), 9.57 (s, 1H). MS: m/z 414 (M+H$^+$).

TABLE 7
Other compounds prepared by method 8:
| Structure | M + H | Structure | M + H |
|---|---|---|---|
| 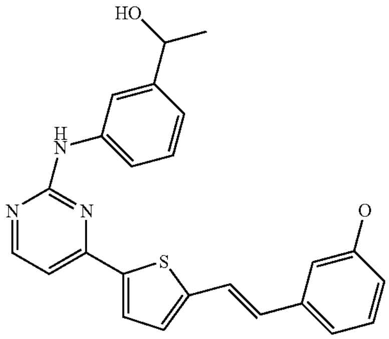 | 434 | 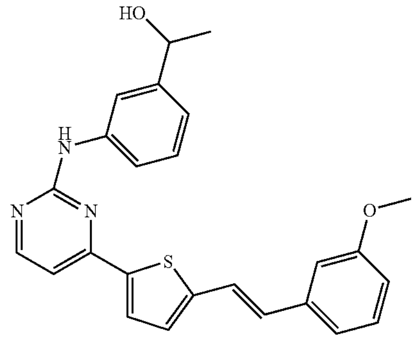 | 430 |
| 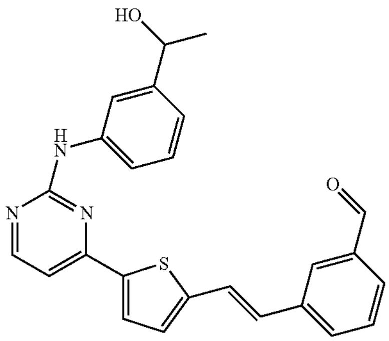 | 428 | | |
Method 9:
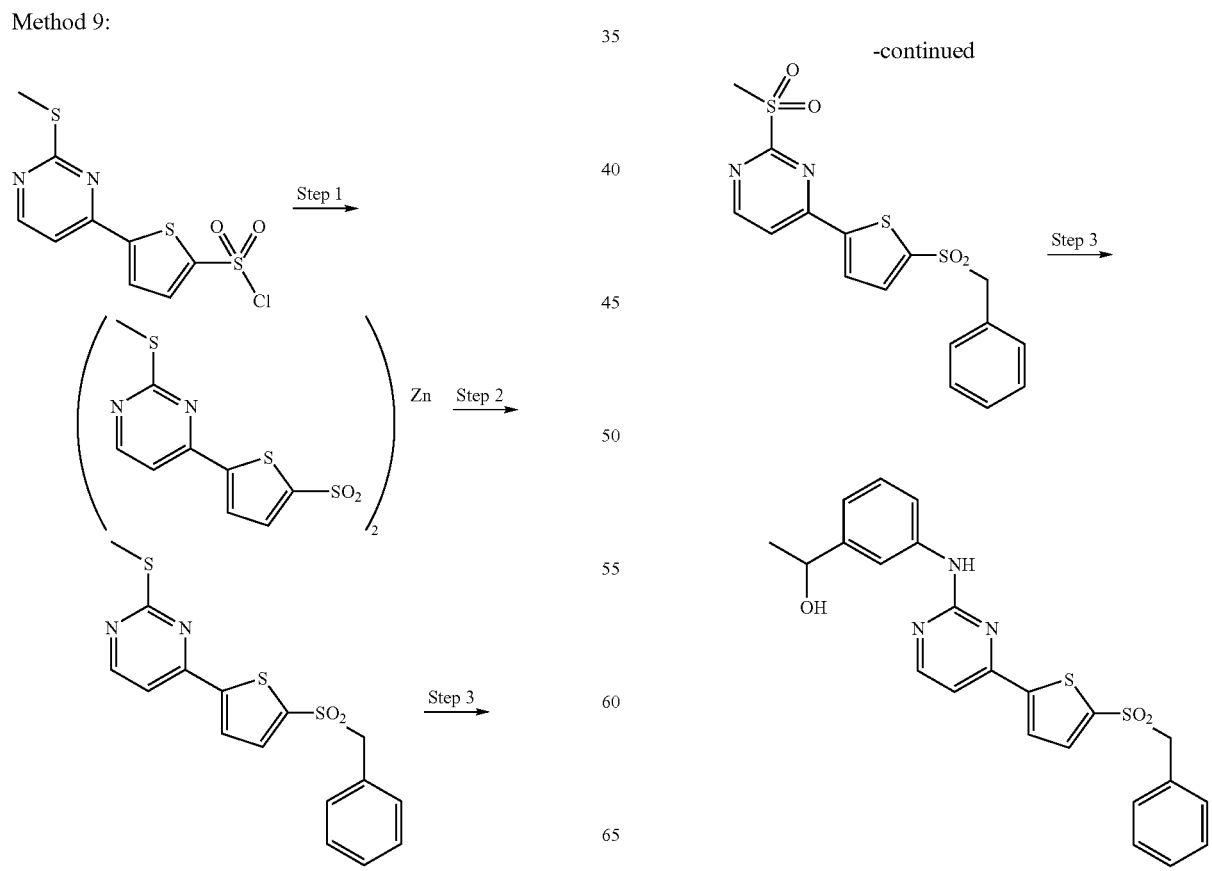

Step 1: Synthesis of bis-5-(2-methylsulfanyl-pyrimidin-4-yl)-thiophene-2-sulfonyl Zinc Zinc dust (106.5 mg, 1.63 mmol) in THF/H$_2$O (2:1, 7.5 mL) was sonicated 15 minutes and 5-(2-Methylsulfanyl-pyrimidin-4-yl)-thiophene-2-sulfonyl chloride (500 mg, 1.63 mmol) was added all at once as a solid. After 22 hours, the mixture was concentrated to ¼ volume and a precipitate formed. Water was added and the suspension was sonicated for 1 minute. The solids were collected by filtration, washed with water and dried in vacuo to afford bis-5-(2-Methylsulfanyl-pyrimidin-4-yl)-thiophene-2-sulfonyl Zinc as a light yellow solid (1.3 g, >100%). This material was used in the next step. $^1$H NMR (500 MHz, DMSO-d6) δ 2.52 (s, 3H), 7.15 (d, J=3.5 Hz, 1H), 7.59 (d, J=5.5 Hz, 1H), 7.88 (d, J=3.5 Hz, 1H), 8.54 (d, J=5.5 Hz, 1H).

Step 2: Synthesis of 2-methylsulfanyl-4-(5-phenyl-methanesulfonyl-thiophen-2-yl)-pyrimidine Benzyl bromide (30.9 uL, 0.180 mmol) was added to a solution of bis-5-(2-methylsulfanyl-pyrimidin-4-yl)-thiophene-2-sulfonyl Zinc dissolved in 3 mL THF and 1.5 mL H$_2$O. The mixture was heated to 70° C. After 12 hours, the mixture was cooled to room temperature and diluted with EtOAc and water and the layers were separated. The material was purified by column chromatography (EtOAc/Hex, gradient 0-80% B) to afford 2-Methylsulfanyl-4-(5-phenyl-methanesulfonyl-thiophen-2-yl)-pyrimidine (7.1 mg, 23.9%). MS: m/z 363 (M+H$^+$).

Step 3: Synthesis of 2-methanesulfonyl-4-(5-phenyl-methanesulfonyl-thiophen-2-yl)-pyrimidine was prepared according to Method 1, step 2, except that the product was filtered through Si—CO$_3$ to remove any remaining m-CPBA/BA. MS: m/z 395 (M+H$^+$).

Step 4: Synthesis of 1-{3-[4-(5-phenylmethanesulfonyl-thiophen-2-yl)-pyrimidin-2-ylamino]-phenyl}-ethanol was prepared according to Method 1, step 3. $^1$H NMR (500 MHz, DCCl$_3$) δ 1.55 (d, J=6 Hz, 3H), 2.64 (s, 2H), 4.47 (s, 1H), 4.96 (q, J=6 Hz, 1H), 7.07 (d, J=5.5 Hz, 1H), 7.16-7.21 (m, 2H), 7.30-7.40 (m, 5H), 7.52 (br d, J=10 Hz, 1H), 7.62 (d, J=4 Hz, 1H), 7.76 (br s, 1H), 8.04 (s, 1H), 8.38 (d, J=5.5 Hz, 1H). MS: m/z 452 (M+H$^+$).

Method 10:

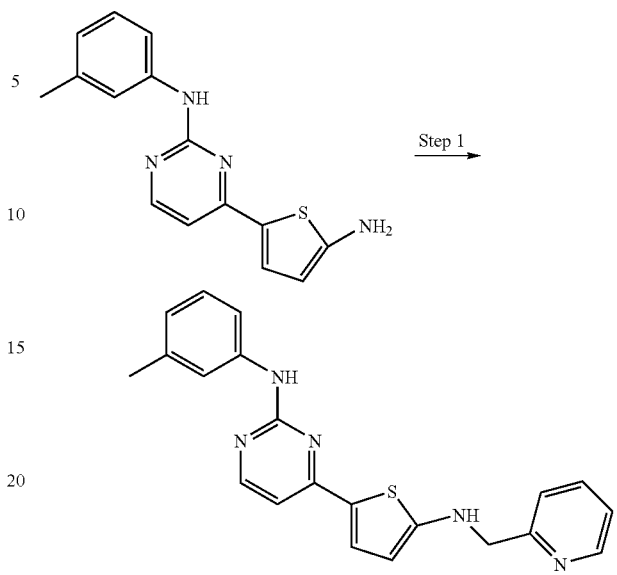

Step 1: Synthesis of (4-{5-[(pyridine-2-ylmethyl)-amino]-thiophen-2-yl}-pyrimidin-2-yl)-m-tolyl-amine A solution of [4-(5-aminothiophen-2-yl)-pyrimidin-2-yl]-m-tolyl-amine (prepared according to Method 4) (15 mg, 0.053 mmol) and pyridine-2-carbaldehyde (4.5 uL, 0.048 mmol) were dissolved in a 25% solution of HOAc in DMA (0.5 mL). MP-CNBH$_3$ resin (2.5 eq.) was added after 2 h and the reaction was shaken for 18 h. The reaction was filtered and the resin washed with DMA. The crude mixture was purified by preparative LCMS to afford 11.1 mg, 61.2%). MS: m/z 374 (M+H$^+$). $^1$H NMR (500 MHz, DMSO-d6) δ2.26 (s, 3H), 4.42 (d, J=6.5 Hz, 2H), 5.96 (d, J=4.5 Hz, 1H), 6.72 (d, J=7.5 Hz, 1H), 6.986 (d, J=5.5 Hz, 1H), 7.10 (t, J=7.5 Hz, 1H), 7.27 (m, 1H), 7.38 (d, J=7.5 Hz, 1H), 7.47 (d, J=7.5 Hz, 1H), 7.56 (d, J=4.0 Hz, 1H), 7.73 (br s, 1H), 7.76 (m, 1H), 7.81 (t, J=5.5 Hz, 1H), 8.16 (d, J=6.0 Hz, 1H), 8.53 (br dd, J=4.5 Hz, 1H), 9.24 (s, 1H).

TABLE 8

Other compounds prepared by method 9:

| Structure | M + H | Structure | M + H |
|---|---|---|---|
| 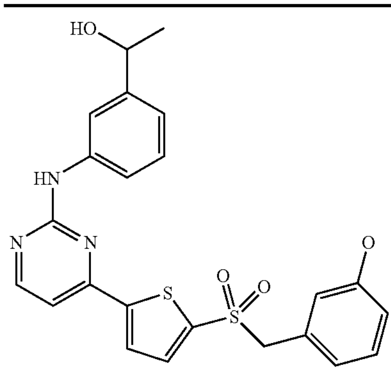 | 486 | 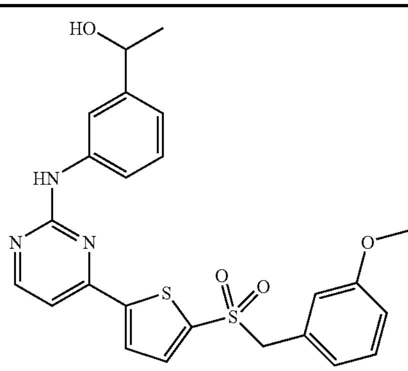 | 482 |

TABLE 9

Other compounds prepared by method 10:

| Structure | M + H | Structure | M + H |
|---|---|---|---|
| (structure) | 430 | (structure) | 407 |
| (structure) | 474 | (structure) | 403 |
| (structure) | 374 | (structure) | 373 |
| (structure) | 407 | (structure) | 363 |

Method 11:

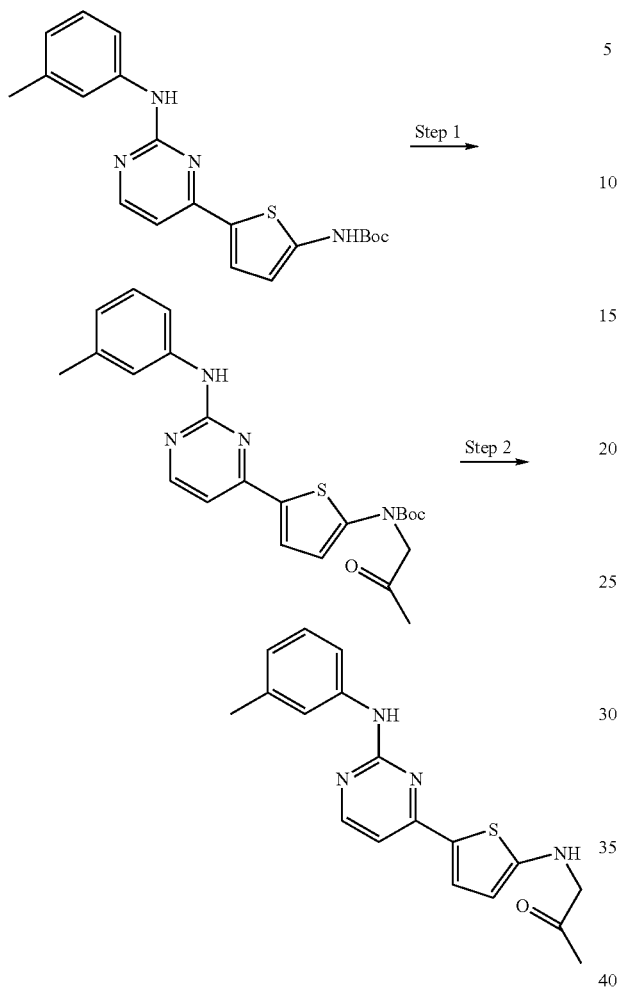

Step 1: Synthesis of (2-Oxo-propyl)-[5-(2-m-tolylamino-pyrimidin-4-yl)-thiophen-2-yl]-carbamic acid tert-butyl ester

[5-(2-m-Tolylamino-pyrimidin-4-yl)-thiophen-2-yl]-carbamic acid tert-butyl ester (30 mg, 0.078 mmol) was dissolved in DMF (0.8 mL) and 60% NaH (4.7 mg, 0.117 mmol) was added. After 8 min., KI (12.9 mg, 0.078 mmol) and chloroacetone (9.4 uL, 0.117 mmol) were added and the reaction was heated to 60° C. for 15 h. The reaction was ~60% converted and an additional aliquot of 60% NaH (3.1 mg, 0.078 mmol) and chloroacetone (6.2 uL, 0.078 mmol) were added and reaction heated at 60° C. for another 18 h. The reaction was concentrated in vacuo and taken to the next step crude.

Step 2: Synthesis of 1-[5-(2-m-Tolylamino-pyrimidine-4-yl)-thiophen-2-ylamino]-propan-2-one (2-Oxo-propyl)-[5-(2-m-tolylamino-pyrimidin-4-yl)-thiophen-2-yl]-carbamic acid tert-butyl ester (0.078 mmol) was treated with 1 mL 4N HCl in dioxane. After 1½ hours, the mixture was concentrated in vacuo and redissolved in EtOAc. The organics were washed with saturated NaHCO$_3$, dried over Na$_2$SO$_4$ and concentrated. The residue was purified by prep LCMS to afford title compound (2.8 mg, 10.5% yield for 2 steps). %). MS: m/z 339 (M+H$^+$). $^1$H NMR (500 MHz, DMSO-d6) δ2.15 (s, 3H), 2.318 (s, 3H), 4.077 (d, J=5.5 Hz, 2H), 5.94 (d, J=4 Hz, 1H), 6.73 (d, J=8 Hz, 1H), 7.02 (d, J=5.5 Hz, 1H), 7.13 (t, J=8 Hz, 1H), 7.41 (t, J=6 Hz, 1H), 7.52 (br d, J=9 Hz, 1H), 7.59 (d, J=4 Hz, 1H), 7.75 (br s, 1H), 8.19 (d, J=5.5 Hz, 1H), 9.27 (s, 1H).

Method 12:

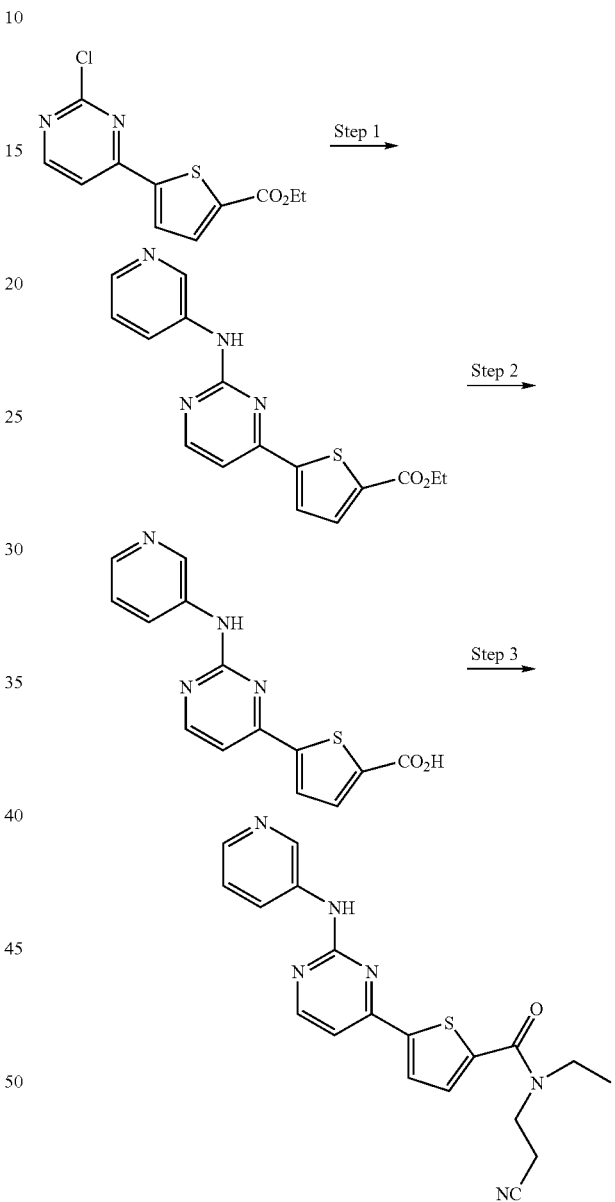

Step 1: Synthesis of 5-[2-(Pyridin-3-ylamino)-pyrimidin-4-yl]-thiophene-2-carboxylic acid ethyl ester Palladium II acetate (8.3 mg, 0.1 mmol) and xantphos 42.8 mg, 0.2 mmol) were precombined in 4 mL dry dioxane under nitrogen gas. Potassium carbonate (1.03 g, 7.46 mmol) was added followed by a solution of 5-(2-Chloro-pyrimidin-4-yl)-thiophene-2-carboxylic acid ethyl ester (100 mg, 0.373 mmol) and 3-aminopyridine (42 mg, 0.447 mmol) in 3 mL dioxane. The reaction was heated in a capped vial at 100° C.

for 20 h. The cooled reaction mixture was diluted with EtOAc and water and the layers were separated. The organic layer was dried over Na₂SO₄ and concentrated in vacuo. The residue was redissolved in ethyl ether and treated with 2 M HCl in ether to generate a precipitate which was collected by filtration to afford 76 mg (56.3%) of the title compound. The crude material was used in the next step.

7.497 (dd, J=1.5, 4 Hz, 1H), 7.985 (dd, J=1.5, 4 Hz, 1H), 8.16 (m, 1H), 8.22 (m, 1H), 8.56 (dd, J=1.5, 5 Hz, 1H), 8.95 (d, J=2.5 Hz, 1H), 9.91, (s, 1H).

TABLE 10

Other compounds prepared by method 12:

| Structure | M + H | Structure | M + H |
|---|---|---|---|
| (pyridin-3-ylamino structure) | 402 | (pyridin-4-ylamino with cyanoethyl/ethyl amide) | 379 |
| (pyridin-4-ylamino with phenylethyl amide) | 402 | | |

Step 2: Synthesis of 5-[2-(Pyridin-3-ylamino)-pyrimidin-4-yl]-thiophene-2-carboxylic acid 5-[2-(Pyridin-3-ylamino)-pyrimidin-4-yl]-thiophene-2-carboxylic acid ethyl ester (76 mg, 0.209 mmol) was saponified by treatment with 4 N LiOH (0.524 mL, 2.09 mmol) in MeOH (1.5 mL) at 40° C. for 15 h. 6 N HCl (2.09 mmol) was added and the mixture was diluted with water. The precipitate was collected by filtration, rinsed with EtOH and dried on vacuum to afford title compound (45 mg, 72%). The crude material was used in the next step.

Step 3: Synthesis of 5-[2-(Pyridin-3-ylamino)-pyrimidin-4-yl]-thiophene-2-carboxylic acid (2-cyanoethyl)-ethyl amide Combined 5-[2-(Pyridin-3-ylamino)-pyrimidin-4-yl]-thiophene-2-carboxylic acid (22 mg, 0.065 mmol), DIEA (27 uL, 0.195 mmol), and HATU (36.8 mg, 0.097 mmol) in DMA (0.5 mL) in a Smith microwave vial. Added 3-ethylamino propionitrile (10.9 uL, 0.097 mmol) and heated in microwave for 900 seconds at 90° C. The crude mixture was purified by prep LCMS to afford title compound (2.7 mg, 10.9%). MS: m/z 379 (M+H⁺). ¹H NMR (500 MHz, DMSO-d6) δ1.203 (br t, 3H), 2.88 (br t, J=6.5 Hz, 2H), 3.65 (Br s, 2H), 3.70 (Br s, 2H), 7.33 (dd, J=5, 8.5 Hz, 1H), 7.469 (dd, J=1.5, 6.5 Hz, 1H), Method 13:

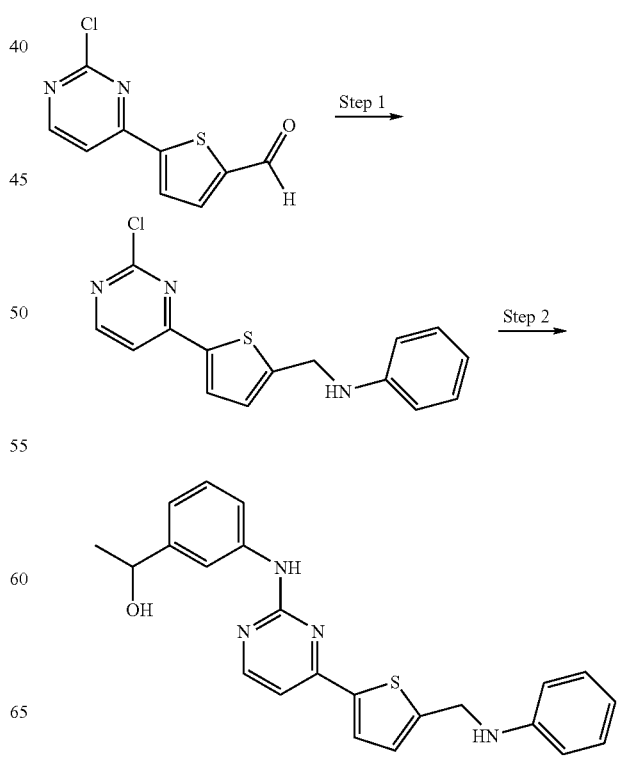

Step 1: Synthesis of [5-(2-Chloro-pyrimidin-4-yl)-thiophen-2-ylmethyl]-phenyl-amine

[5-(2-Chloro-pyrimidin-4-yl)-thiophene-2-carbaldehyde (100 mg, 0.446 mmol) was dissolved in 25% HOAc in DMA (4 mL) and was treated with aniline (61 uL, 0.669 mmol) for 2 h. MP-CNBH$_3$ resin was added the reaction was shaken for 18 h. The reaction was filtered and rinsed with DMA and the solution was concentrated in vacuo. The crude material was purified by SiO$_2$ chromatography using a gradient 0-100% hexanes/EtOAc to afford title compound (80 mg, 59%).

Step 2: Synthesis of 1-{3-[4-(5-Phenylaminomethyl-thiophen-2-yl)-pyrimidin-2-ylamino]-phenyl}-ethanol This product was prepared as described in Method 2. MS: m/z 403 (M+H$^+$). $^1$H NMR (500 MHz, DMSO-d6) δ1.25 (s, 3H), 4.42 (d, J=6.5 Hz, 2H), 4.6 (m, 1H), 5.01 (d, J=3.5 Hz, 1H), 6.31 (t, J=8 Hz, 1H), 6.48 (t, J=8 Hz, 1H), 6.56 (d, J=7 Hz, 2H), 6.87 (d, J=8 Hz, 1H), 7.00 (t, J=6 Hz, 1H), 7.06 (d, J=3 Hz, 1H), 7.13 (t, J=8 Hz, 1H), 7.16 (d, J=5.5 Hz, 1H), 7.55 (br d, J=8 Hz, 1H), 7.71 (br s, 1H), 7.77 (d, J=3 Hz, 1H), 8.35 (d, J=5 Hz, 1H), 9.46 (s, 1H).

TABLE 11

Other compounds prepared by method 13:

| Structure | M + H | Structure | M + H |
|---|---|---|---|
| 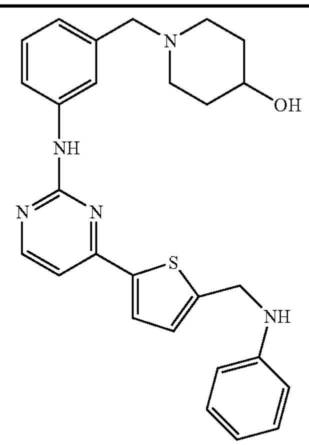 | 472 | 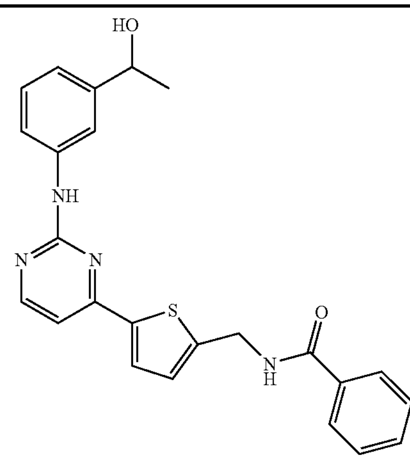 | 431 |
| 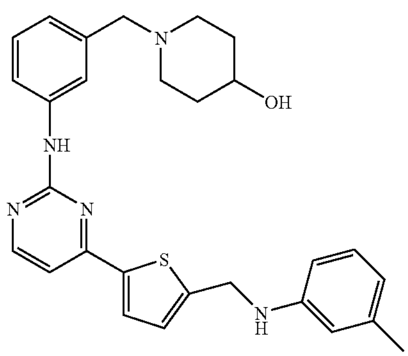 | 486 | 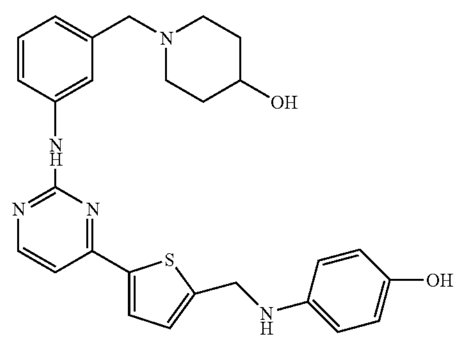 | 506 |
| 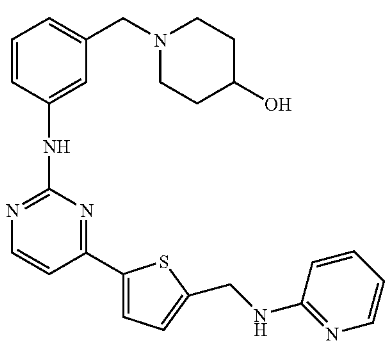 | 473 | 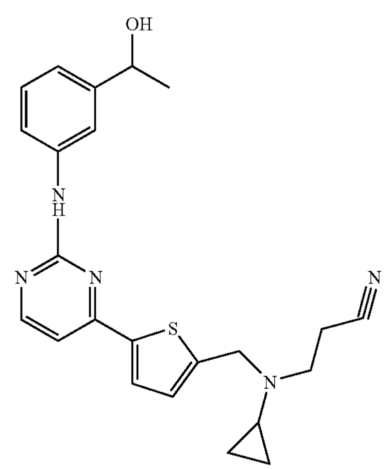 | 420 |

TABLE 11-continued

Other compounds prepared by method 13:

| Structure | M + H | Structure | M + H |
|---|---|---|---|
| 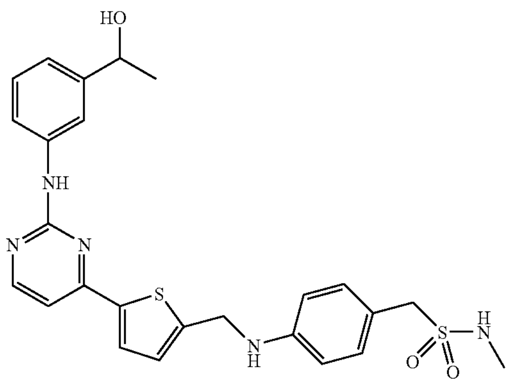 | 510 | 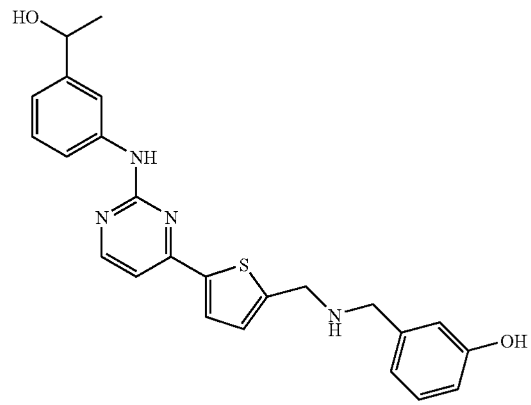 | 451 |
| | 506 | | 486 |
| | 506 | | 510 |
| 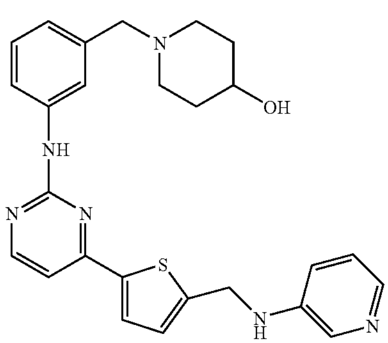 | 473 | 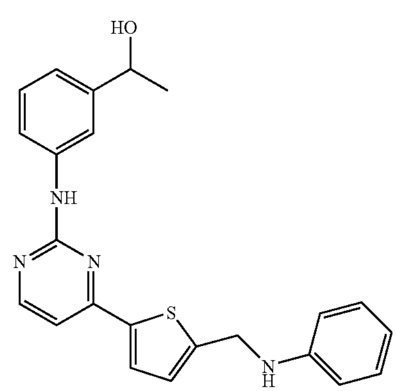 | 403 |

TABLE 11-continued

Other compounds prepared by method 13:

| Structure | M + H | Structure | M + H |
|---|---|---|---|
| 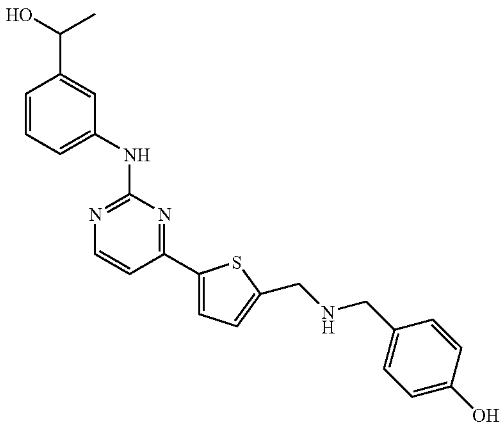 | 451 | 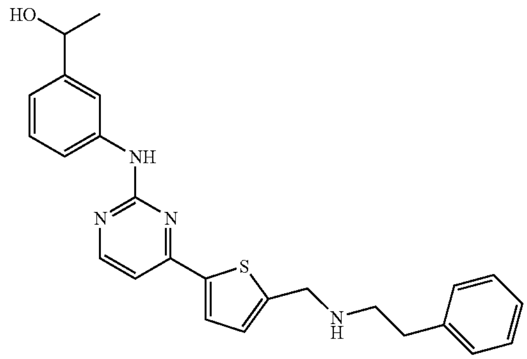 | 431 |
| 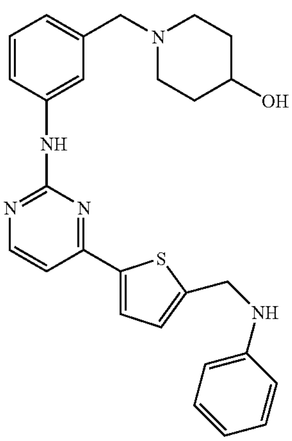 | 472 | 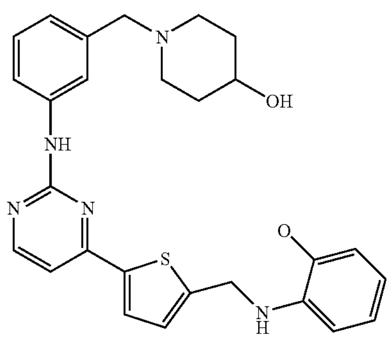 | 506 |
| 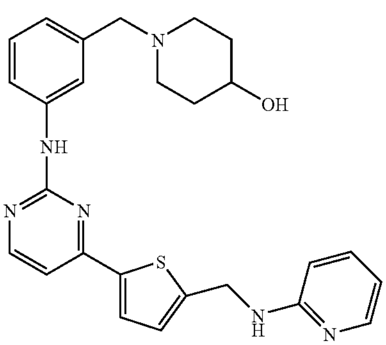 | 473 | 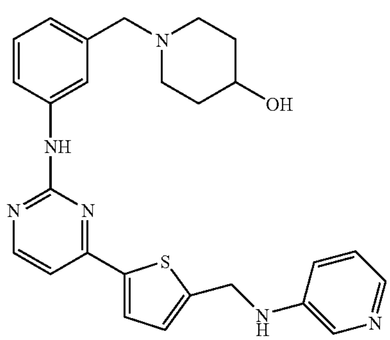 | 473 |

TABLE 11-continued

Other compounds prepared by method 13:

| Structure | M + H | Structure | M + H |
|---|---|---|---|
| 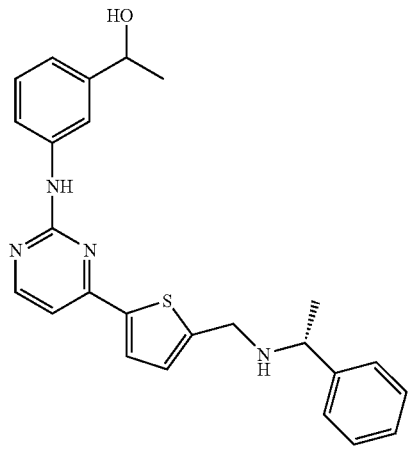 | 431 | | |

Method 14:

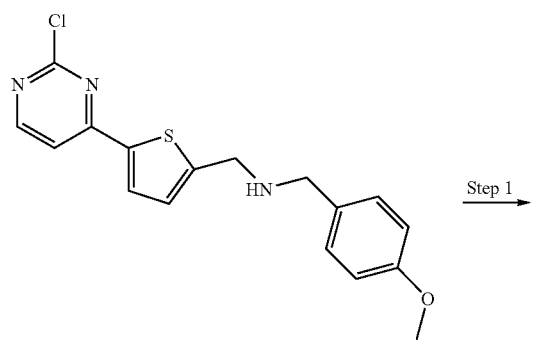

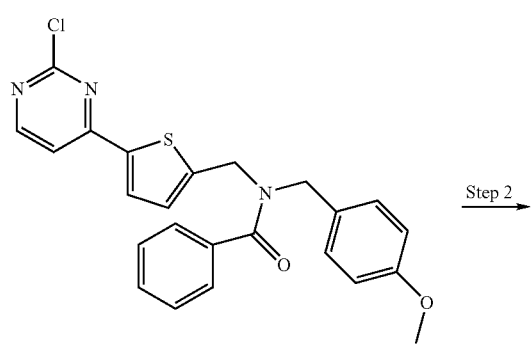

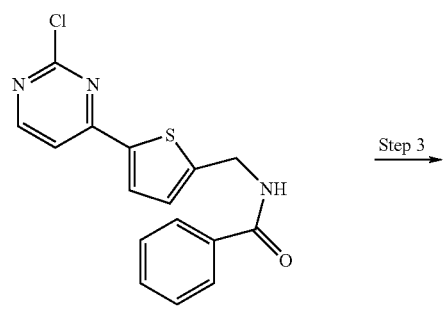

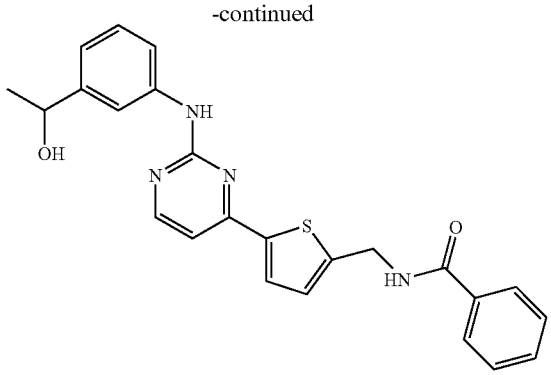

Step 1: Synthesis of N-[5-(2-Chloro-pyrimidin-4-yl)-thiophen-2-ylmethyl]-N-(4-methoxybenzyl)-benzamide

[5-(2-Chloro-pyrimidin-4-yl)-thiophen-2-ylmethyl]-(4-methoxybenzyl)-amine (22 mg, 0.063 mmol) was dissolved in CH$_2$Cl$_2$ (1 mL) and treated with pyridine (4.3 uL, 0.076 mmol) and Et$_3$N (17.8 uL, 0.127 mmol), followed by benzoyl chloride (8.9 uL, 0.765 mmol). The mixture was allowed to stir for 18 h and was then washed with 1 N HCl, dried over Na$_2$SO$_4$ and concentrated. The material was used crude in the next step.

Step 2: Synthesis of N-[5-(2-Chloro-pyrimidin-4-yl)-thiophen-2-ylmethyl]-benzamide A solution of N-[5-(2-Chloro-pyrimidin-4-yl)-thiophen-2-ylmethyl]-N-(4-methoxybenzyl)-benzamide (25 mg, 0.055 mmol) in 0.25 mL CH$_2$Cl$_2$ was treated with trifluoroacetic acid (0.25 mL) as co-solvent and PS-thiophenol resin (3 eq.) at 40° C. for 15 h. The material was filtered and concentrated to a yellow solid (16 mg, 88%). The crude material was used in the next step.

185

Step 2: Synthesis of N-(5-{2-[3-(1-hydroxyethyl)-phenylamino]-pyrimidin-4-yl}-thiophen-2-ylmethyl)-benzamide The title compound was prepared according to method 2. MS: m/z 431 (M+H$^+$). $^1$H NMR (500 MHz, DMSO-d6) δ1.23 (d, J=6 Hz, 1H), 4.61 (m, 3H), 5.0 (br s, 1H), 6.86 (d, J=7.5 Hz, 1H), 7.04 (d, J=3.5 Hz, 1H), 7.10 (t, J=8 Hz, 1H), 7.19 (d, J=5 Hz, 1H), 7.42 (m, 2H), 7.47 (d, J=7 Hz, 1H), 7.55 (d, J=6.5 Hz, 1H), 7.7 (br s, 1H), 7.77 (d, J=3.5 Hz, 1H), 7.83 (m, 2H), 8.36 (d, J=5 Hz, 1H), 9.19 (t, J=5.5 Hz, 1H), 9.47 (s, 1H). Method 15:

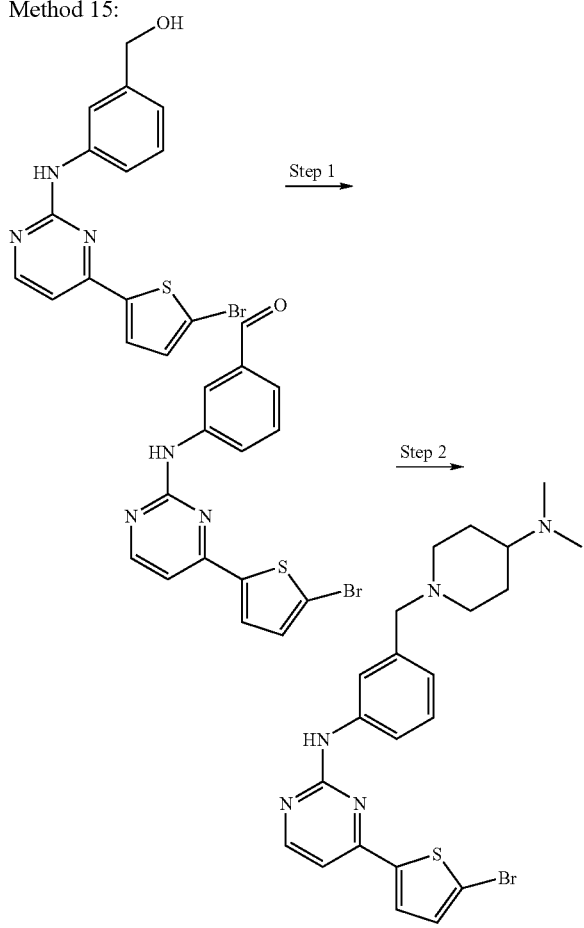

186

Step 1: Synthesis of 3-[4-(5-Bromo-thiophen-2-yl)-pyrimidin-2-ylamino]-benzaldehyde A suspension of {3-[4-(5-Bromo-thiophen-2-yl)-pyrimidin-2-ylamino]-phenyl}-methanol (566 mg, 1.57 mmol) was treated with MnO$_2$ (1.4 g, 15.7 mmol) for 15 h. Another aliquot of 500 mg MnO$_2$ was added and the reaction was allowed to stir for 48 h. The mixture was filtered over celite and dried in vacuo to afford 375 mg (88% pure by LCMS and $^1$H NMR) which was used crude in the next step.

Step 2: Synthesis of [4-(5-Bromo-thiophen-2-yl)-pyrimidin-2-yl]-[3-(4-dimethylaminopiperidin-1-ylmethyl)-phenyl]-amine A solution of 3-[4-(5-Bromo-thiophen-2-yl)-pyrimidin-2-ylamino]-benzaldehyde (25 mg, 0.069 mmol) and 4-dimethylaminopiperidine (13.3 mg, 0.104 mmol) in 25% HOAc in DMA was mixed for 2 h and then treated with MP-CNBH$_3$ (2.5 eq.) for 18 h. The reactions were filtered and purified directly by LCMS to afford title compound (2.3 mg, 7%) for 2 steps. MS: m/z 472 (M+H$^+$). $^1$H NMR (500 MHz, DMSO-d6) δ1.37 (br q, J=11 Hz, 2H), 1.70 (br d, J=12 Hz, 2H), 1.94 (br t, J=11 Hz, 2H), 2.04 (br t, 1H), 2.87 (br d, J=11 Hz, 2H), 3.33 (s, 2H), 6.89 (d, J=7.5 Hz, 1H), 7.24 (t, J=7.5 Hz, 1H), 7.33 (dd, J=1, 5 Hz, 1H), 7.37 (m, 1H), 7.55 (br d, J=8 Hz, 1H), 7.86 (m, 1H), 7.89 (br s, 1H), 8.51 (dd, J=1.5, 5 Hz, 1H), 9.68 (s, 1H).

Products containing a BOC protection group were treated, after filtration of the resin, with 0.5 mL 6 N HCl at 50° C. for 2 h, and were dried in vacuo and redissolved in DMSO for prep purification.

TABLE 12

| Other compounds prepared by method 15: | | | |
|---|---|---|---|
| Structure | M + H | Structure | M + H |
| | 404/406 | | 432/434 |

TABLE 12-continued
Other compounds prepared by method 15:
| Structure | M + H | Structure | M + H |
|---|---|---|---|
| 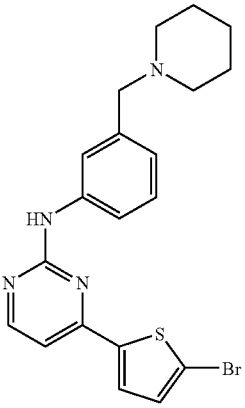 | 429/431 | 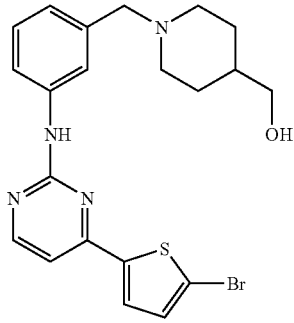 | 459/461 |
| 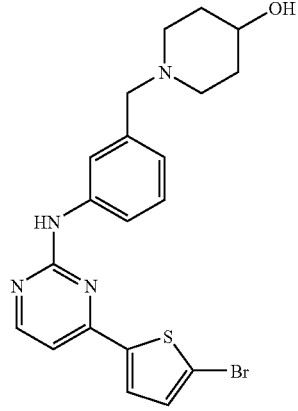 | 445/447 | 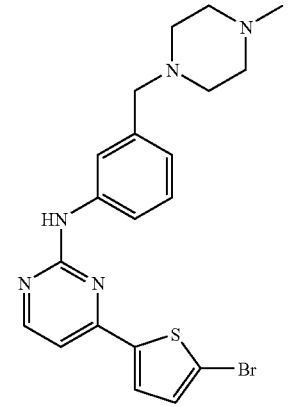 | 444/446 |
| 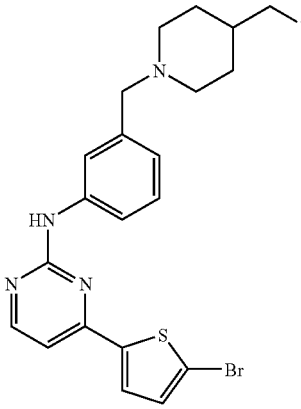 | 458/460 | 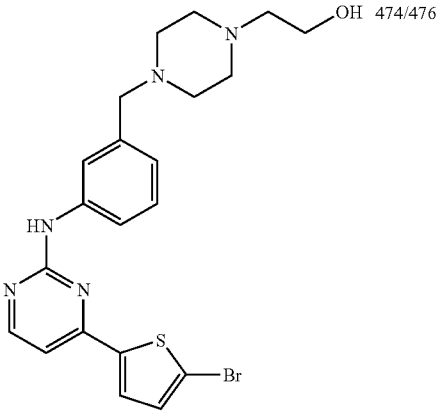 | 474/476 |

TABLE 12-continued
Other compounds prepared by method 15:
| Structure | M + H | Structure | M + H |
|---|---|---|---|
| 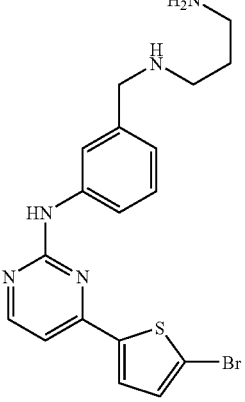 | 418/420 | 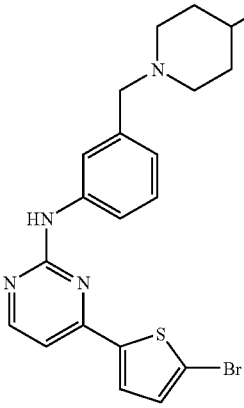 | 473/475 |
| 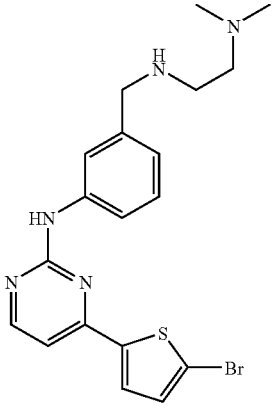 | 432/434 | 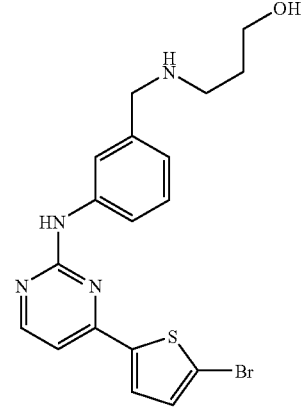 | 419/421 |
| 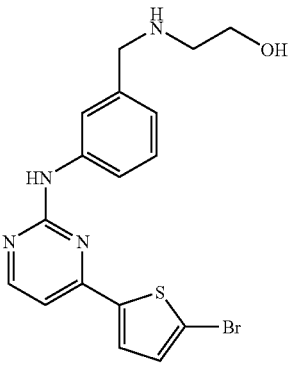 | 405/407 | 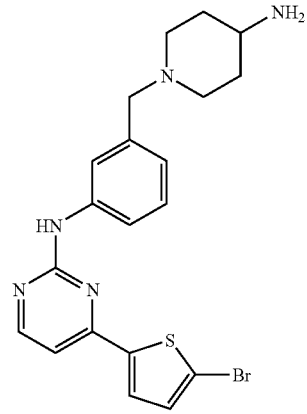 | 444/446 |

TABLE 12-continued
Other compounds prepared by method 15:
| Structure | M + H | Structure | M + H |
|---|---|---|---|
| 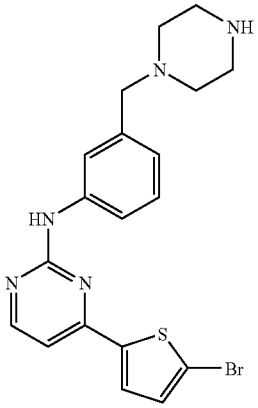 | 430/432 | 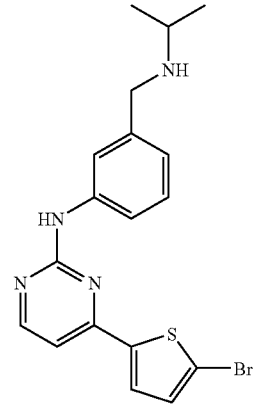 | 403/405 |
| 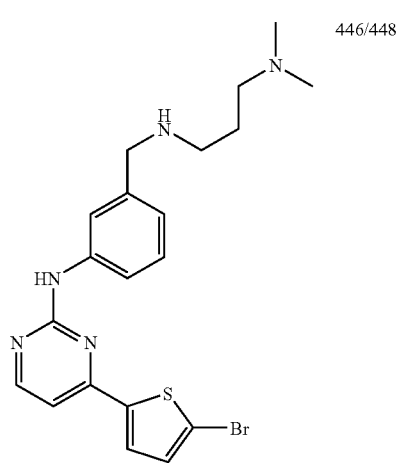 | 446/448 | | |
Method 16:
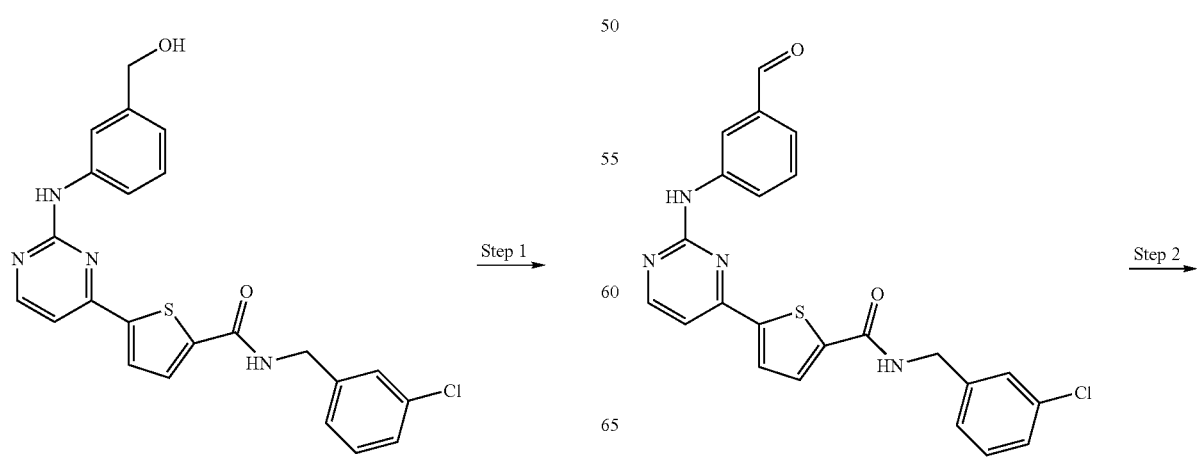

-continued

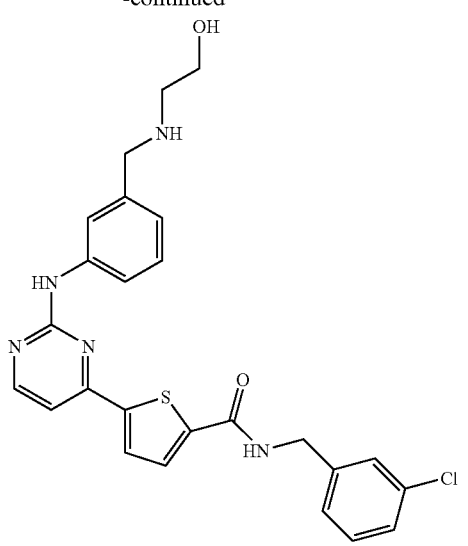

Step 1: Synthesis of 5-[2-formyl-phenylamino)-pyrimidin-4-yl]-thiophene-2-carboxylic acid 4-chloro benzylamide Crude 5-[2-(3-Hydroxymethyl-phenylamino)-pyrimidin-4-yl]-thiophene-2-carboxylic acid 4-chloro benzylamide (137.2 mg, 0.305 mmol), prepared as described in method 12, was treated with $MnO_2$ (265 mg, 3.05 mmol) in 1 mL acetone. After 12 h at room temperature, the mixture was concentrated in vacuo, redissolved in EtOAc and passed through a 5 g $SiO_2$ cartridge using EtOAc as eluent. A yellow oil (69.6 mg, 50.8%, 2 steps) was obtained and used in the next step.

Step 2: Synthesis of 5-(2-{3-[(2-hydroxy-ethylamino)-methyl]-phenylamino}-pyrimidin-4-yl)-thiophene-2-carboxylic acid 4-chloro benzylamide 5-[2-formyl-phenylamino)-pyrimidin-4-yl]-thiophene-2-carboxylic acid 4-chloro benzylamide (22.4 mg, 0.05 mmol) and 2-aminoethanol (4.5 uL, 0.075 mmol) were incubated in 25% HOAc/DMA (0.5 mL) for 2 h and then treated with 2.5 eq. $MP-CNBH_3$ resin for 15 h. The reaction was filtered and the eluent was prep purified to afford title compound (8.9 mg, 36%). MS: m/z 494 (M+H$^+$). $^1$H NMR (500 MHz, DMSO-d6) δ2.67 (t, J=6 Hz, 2H), 3.50 (t, J=6 Hz, 2H), 3.79 (s, 2H), 4.47 (d, J=6.5 Hz, 2H), 6.98 (d, J=7.5 Hz, 1H), 7.25-7.38 (m, 5H), 7.69 (br d, J=7.5 Hz, 1H), 7.81 (br s, 1H), 7.86 (d, J=4 Hz, 1H), 8.00 (d, J=4 Hz, 1H), 8.539 (d, J=5.5 Hz, 1H), 9.25 (t, J=6 Hz, 1H), 9.70 (s, 1H).

TABLE 13

Other compounds prepared by method 16:

| Structure | M + H | Structure | M + H |
|---|---|---|---|
| 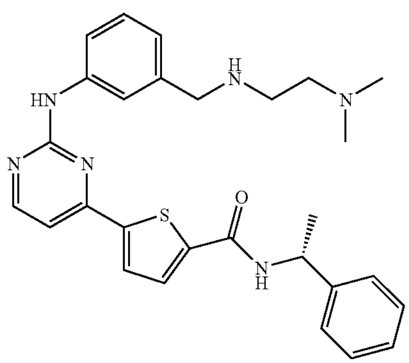 | 501 | 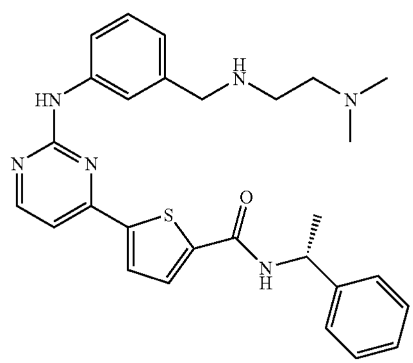 | 501 |
| 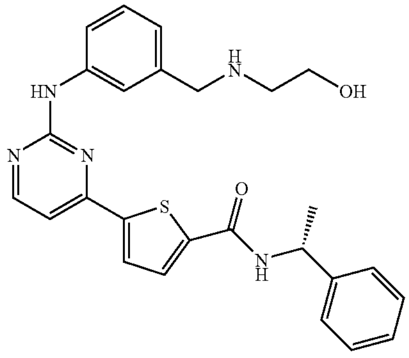 | 474 | 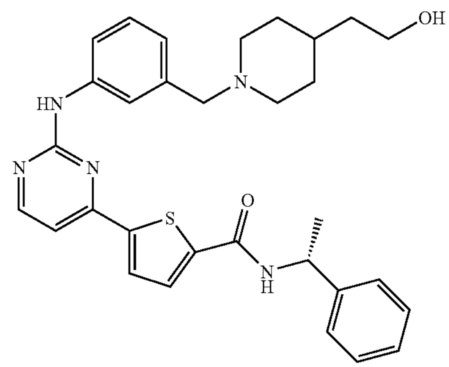 | 542 |

TABLE 13-continued

Other compounds prepared by method 16:

| Structure | M + H | Structure | M + H |
|---|---|---|---|
| 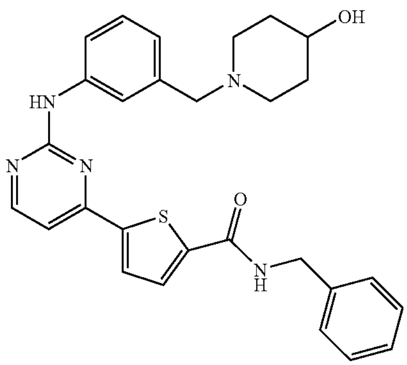 | 515 | 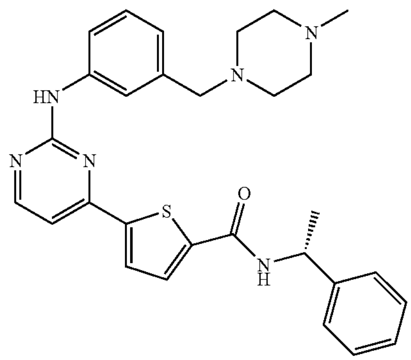 | 513 |
| 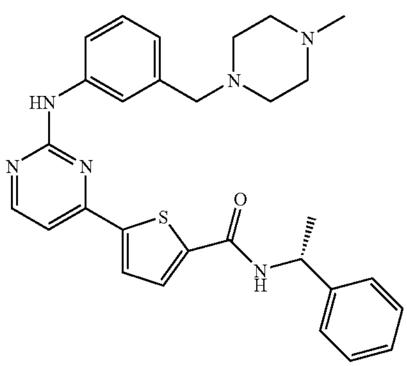 | 513 | 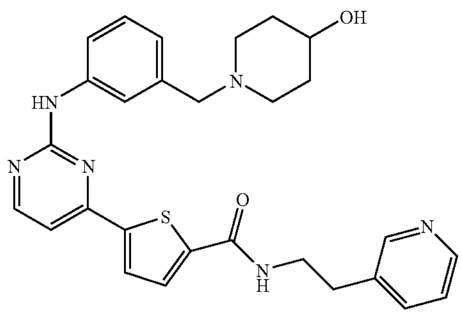 | 515 |
| 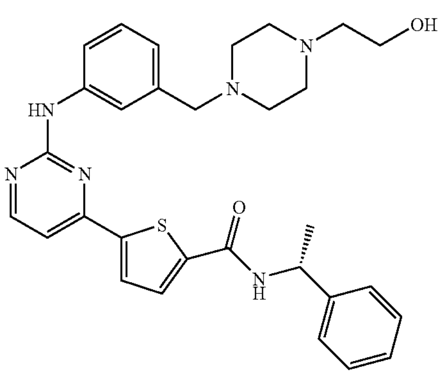 | 543 | 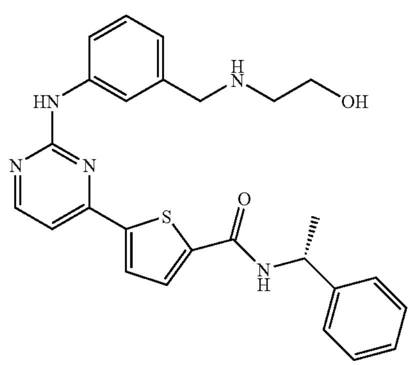 | 474 |

TABLE 13-continued

Other compounds prepared by method 16:

| Structure | M + H | Structure | M + H |
|---|---|---|---|
| (structure) | 542 | (structure) | 451 |
| (structure) | 518 | (structure) | 562 |
| (structure) | 543 | (structure) | 534 |

TABLE 13-continued
Other compounds prepared by method 16:
| Structure | M + H | Structure | M + H |
|---|---|---|---|
|  | 490 |  | 514 |
|  | 450 |  | 491 |
Method 17:
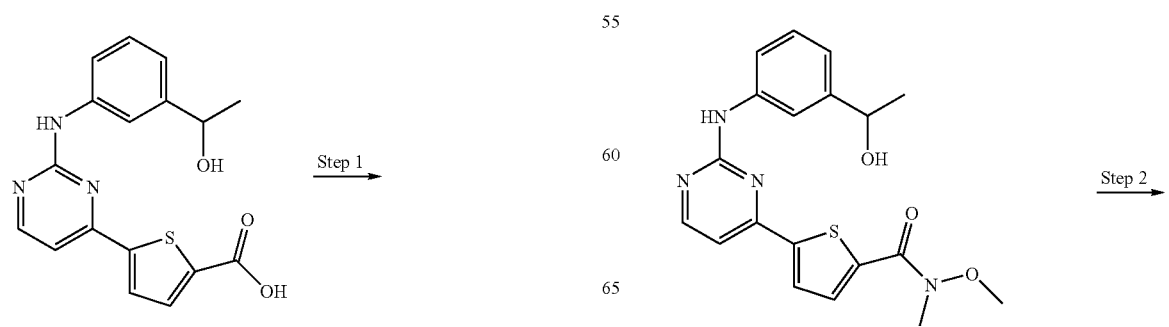
-continued -continued

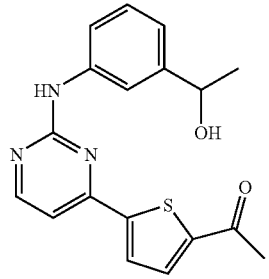

Step 1: Synthesis of 5-{2-[3-(1-Hydroxy-ethyl)-phenylamino]-pyrimidin-4-yl}-thiophene-2-carboxylic acid methoxy-methyl-amide 5-(3-dimethylamino-acryloyl)thiophene-2-carboxylic acid (692 mg, 2.02 mmol), N,O-Dimethylhydroxylamine hydrochloride (297 mg, 3.04 mmol), O-(7-Azabenzotriazol-1-yl)-N,N,N',N'-tetramethyluronium hexafluorophosphate (925 mg, 2.43 mmol), and diisopropylamine (1.39 mL, 8.11 mmol) were dissolved in 4 mL of dry DMF. Stirred at 90° C. for 1 hr. The mixture was concentrated and purified via flash chromatography (hexanes/ethyl acetate+10% methanol gradient) to give 297 mg of 5-{2-[3-(1-Hydroxy-ethyl)-phenylamino]-pyrimidin-4-yl}-thiophene-2-carboxylic acid methoxy-methyl-amide as a yellow solid (0.76 mmol, 38%).

Step 2: Synthesis of 1-(5-{2-[3-(1-Hydroxy-ethyl)-phenylamino]-pyrimidin-4-yl}-thiophen-2-yl)-ethanone 5-{2-[3-(1-Hydroxy-ethyl)-phenylamino]-pyrimidin-4-yl}-thiophene-2-carboxylic acid methoxy-methyl-amide (30 mg, 78 µmol) was dissolved in 5 mL of dry THF and cooled to −78° C. Methylmagnesium bromide (3M in ether, 130 µl, 390 µmol) was added dropwise. The mixture was slowly warmed to room temperature and stirred until all the starting material was consumed (LCMS). The reaction mixture was quenched by addition of a saturated ammonium chloride solution and passed through a Varian Chem Elut cartridge. The crude product was concentrated and purified via flash chromatography (hexanes/ethyl acetate+10% methanol gradient) and preparative HPLC (water/acetonitrile gradient) to give 6.6 mg of 1-(5-{2-[3-(1-Hydroxy-ethyl)-phenylamino]-pyrimidin-4-yl}-thiophen-2-yl)-ethanone as a yellow solid (0.19 µmol, 25%). $^1$H NMR (500 MHz, DMSO-d6) δ 9.71 (s, 1H), 8.56 (d, J=5 Hz, 1H), 8.07 (d, J=4 Hz, 1H), 7.99 (d, J=4 Hz, 1H), 7.83 (s, 1H), 7.61 (m, 1H), 7.43 (d, J=5 Hz, 1H), 7.25 (t, J=8 Hz, 1H), 6.98 (d, J=8 Hz, 1H), 5.13 (bs, 1H), 4.71 (q, J=6.5 Hz, 1H), 2.57 (s, 3H), 1.36 (d, J=6.5 Hz, 3H). MS: m/z 340 (M+H$^+$).

TABLE 14

Other compounds prepared by method 17:

| Structure | M + H | Structure | M + H |
|---|---|---|---|
| 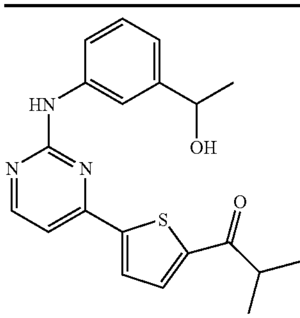 | 368 | 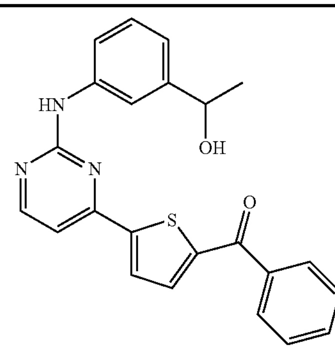 | 402 |

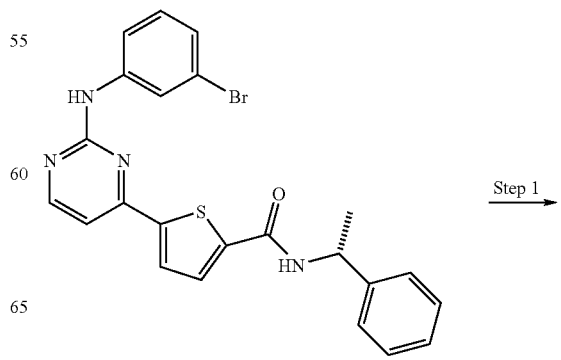

Method 18:

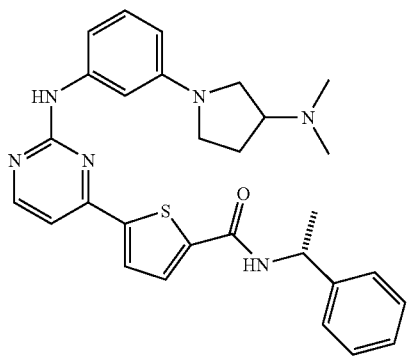

Step 1: Synthesis of 5-[2-(3-Morpholin-4-yl-phenylamino)-pyrimidin-4-yl]-thiophene-2-carboxylic acid (1-phenyl-ethyl)-amide 5-[2-(3-Bromo-phenylamino)-pyrimidin-4-yl]-thiophene-2-carboxylic acid (1-phenyl-ethyl)-amide (20 mg, 41 μmol), 3-dimethylamino pyrrolidine (6 mg, 0.5 μmol), tris(dibenzylideneacetone)dipalladium(0) chloroform adduct (1.5 mg, 2 μmol), and 2-dicyclohexylphosphino-2'-(N,N-dimethylamino)biphenyl (2 mg, 5 μmol) were suspended in 0.2 mL lithium bis(trimethylsilyl)amide solution in THF (1M). The reaction mixture was stirred at 65° C. for 48 hours. The reaction was quenched with 1 mL MeOH and concentrated and the crude product was redissolved in DMSO and purified by mass triggered reverse phase HPLC to afford 1.2 mg of pure 5-{2-[3-(3-Dimethylamino-pyrrolidin-1-yl)-phenylamino]-pyrimidin-4-yl}-thiophene-2-carboxylic acid (1-phenyl-ethyl)-amide (2.5 μmol, 6%, 1:1 mixture of diastereomers). $^1$H NMR (500 MHz, DMSO-d6) δ 9.45 (s, 1H), 8.94 (d, J=8 Hz, 1H), 8.50 (d, J=5 Hz, 1H), 7.97 (d, J=4 Hz, 1H), 7.92 (d, J=4 Hz, 1H), 7.39 (d, J=5 Hz, 2H), 7.33 (m, 4H), 7.23 (t, J=7 Hz, 1H), 7.18 (s, 1H), 6.98 (m, 1H), 6.17 (d, J=7.5 Hz, 1H), 5.14 (quintet, J=6.5 Hz, 1H), 3.45 (q, J=8 Hz, 1H), 3.39 (t, J=8 Hz, 1H), 3.32 (m, 2H), 3.02 (q, J=8 Hz, 1H), 2.77 (m, 1H), 2.15 (s, 6H), 1.79 (m, 1H), 1.49 (d, J=6.5 Hz, 3H). MS: m/z 513 (M+H$^+$).

TABLE 15

Other compounds prepared by method 18:

| Structure | M + H | Structure | M + H |
|---|---|---|---|
| 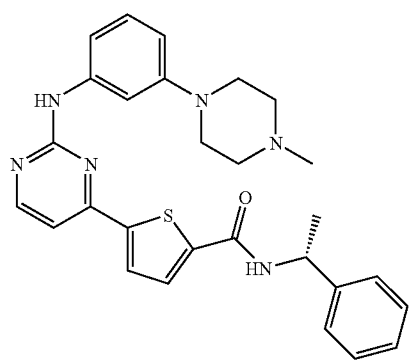 | 499 | 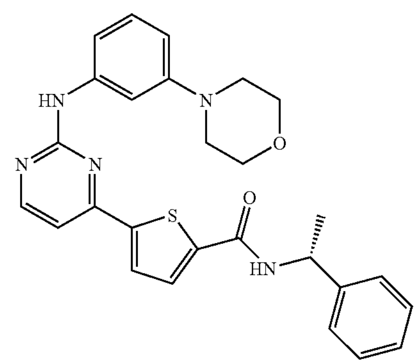 | 486 |
| 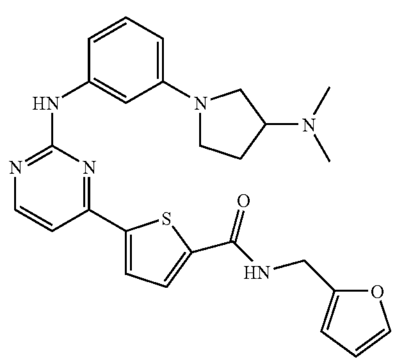 | 489 | 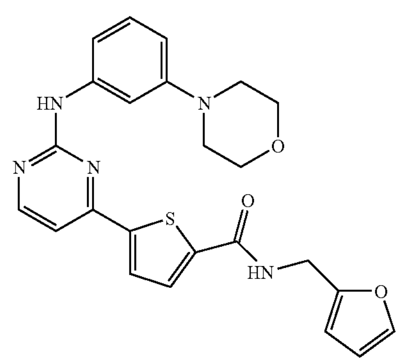 | 462 |

TABLE 15-continued

Other compounds prepared by method 18:

| Structure | M + H | Structure | M + H |
| --- | --- | --- | --- |
| 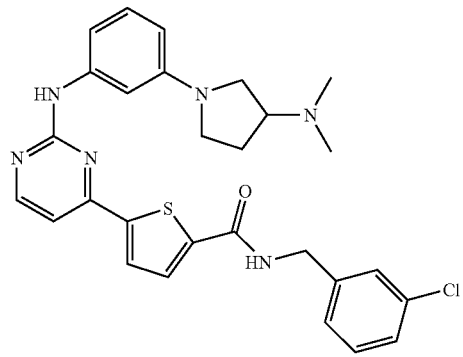 | 534 | | |

Method 19:

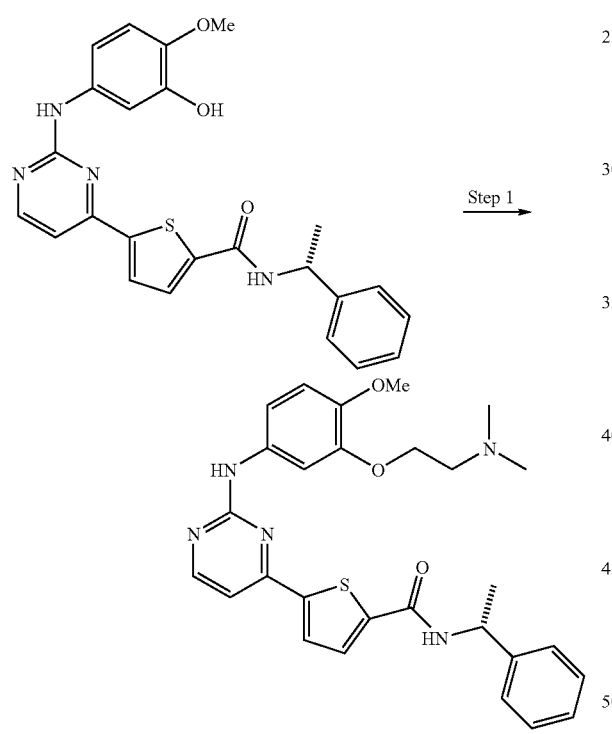

Step 1: Synthesis of 5-{2-[3-(2-Dimethylamino-ethoxy)-4-methoxy-phenylamino]-pyrimidin-4-yl}-thiophene-2-carboxylic acid (1-phenyl-ethyl)-amide 5-[2-(3-Hydroxy-4-methoxy-phenylamino)-pyrimidin-4-yl]-thiophene-2-carboxylic acid (1-phenyl-ethyl)-amide (35 mg, 78 µmol), dimethylaminoethanol (26 µL, 156 µmol), and triphenylphosphine (41 mg, 156 µmol) were dissolved in 0.14 mL THF and cooled to 0° C. Diisopropyldiazodicarboxylate (31 µL, 156 µmol) were added dropwise. The reaction mixture was slowly warmed to room temperature and stirred overnight. The crude product was diluted with DMSO and purified by mass triggered reverse phase HPLC to afford 0.3 mg of pure 5-{2-[3-(2-Dimethylamino-ethoxy)-4-methoxy-phenylamino]-pyrimidin-4-yl}-thiophene-2-carboxylic acid (1-phenyl-ethyl)-amide (0.6 µmol, 1%). $^{1}$H NMR (500 MHz, DMSO-d6) δ 9.49 (s, 1H), 8.94 (d, J=8 Hz, 1H), 8.47 (d, J=5 Hz, 1H), 7.98 (d, J=4 Hz, 1H), 7.93 (d, J=4 Hz, 1H), 7.57 (m, 1H), 7.38 (m, 2H), 7.31 (m, 4H), 7.23 (m, 1H), 6.88 (d, J=8 Hz, 1H), 5.12 (quintet, J=7.5 Hz, 1H), 4.05 (t, J=6 Hz, 2H), 3.71 (s, 3H), 2.64 (t, J=6 Hz, 2H), 2.17 (s, 6H), 1.48 (d, J=6.5 Hz, 3H). MS: m/z 518 (M+H$^{+}$).

TABLE 16

Other compounds prepared by method 19:

| Structure | M + H |
| --- | --- |
| 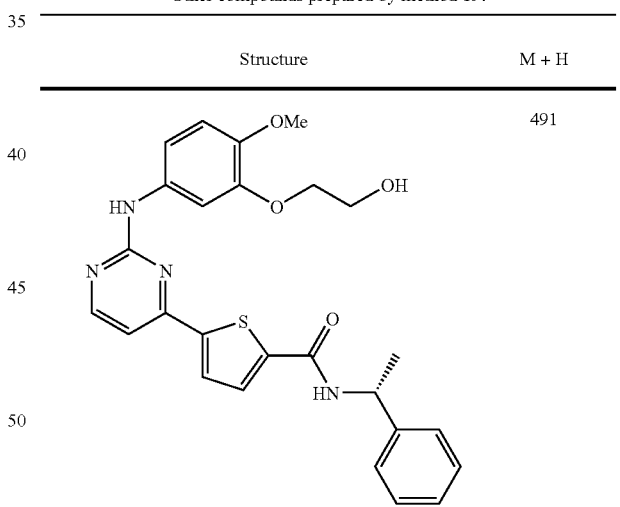 | 491 |

Method 20:

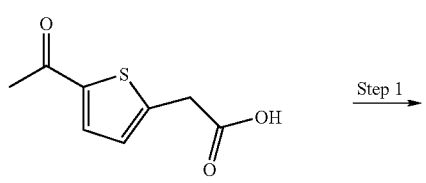

Step 1

-continued

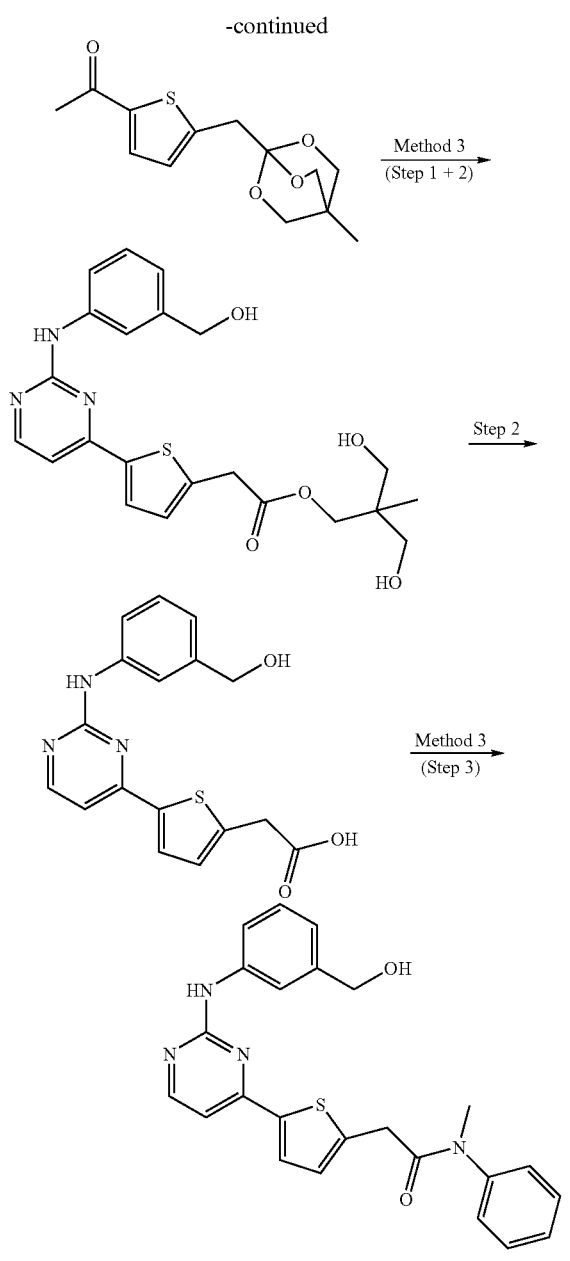

Step 1: Synthesis of 1-[5-(4-Methyl-2,6,7-trioxa-bicyclo[2.2.2]oct-1-ylmethyl)-thiophen-2-yl]-ethanone (5-Acetyl-thiophen-2-yl)-acetic acid (2 g, 10.8 mmol), 3-hydroxymethyl-3-methyloxetane (1.07 mL, 10.8 mmol), and dimethylaminopyridine (221 mg, 1.08 mmol) were dissolved in 5 mL of dry THF and cooled to 0° C. Dicyclohexylcarbodiimide (2.24 g, 10.8 mmol) was added and the mixture was stirred at 0° C. for 1 hr, then warmed to room temperature and stirred overnight. The mixture was cooled to 0° C. and filtered. The white solid was washed with cold THF and the combined filtrates were concentrated. The crude product was purified via flash chromatography (hexanes/ethyl acetate gradient) to give 2.3 g of (5-Acetyl-thiophen-2-yl)-acetic acid 3-methyl-oxetan-3-ylmethyl ester (8.5 mmol, 79%). The product was dissolved in 20 mL DCM and cooled to −5° C.

Boron trifluoride diethyletherate (121 µL, 1 mmol) was added dropwise, the mixture was slowly warmed to room temperature and stirred for 30 minutes. The reaction was quenched with triethylamine, concentrated and purified via flash chromatography (hexanes/ethyl acetate gradient) to give 1.44 g of 1-[5-(4-Methyl-2,6,7-trioxa-bicyclo[2.2.2]oct-1-ylmethyl)-thiophen-2-yl]-ethanone (4.1 mmol, 38% over two steps).

1-[5-(4-Methyl-2,6,7-trioxa-bicyclo[2.2.2]oct-1-ylmethyl)-thiophen-2-yl]-ethanone was converted to {5-[2-(3-Hydroxymethyl-phenylamino)-pyrimidin-4-yl]-thiophen-2-yl}-acetic acid 3-hydroxy-2-hydroxymethyl-2-methyl-propyl ester following method 3, steps 1 and 2.

Step 2: Synthesis of {5-[2-(3-Hydroxymethyl-phenylamino)-pyrimidin-4-yl]-thiophen-2-yl}-acetic acid {5-[2-(3-Hydroxymethyl-phenylamino)-pyrimidin-4-yl]-thiophen-2-yl}-acetic acid 3-hydroxy-2-hydroxymethyl-2-methyl-propyl ester (717 mg, 1.6 mmol) was dissolved in 30 mL of THF and 1N sodium hydroxide solution (3.5 mL, 3.5 mmol). The mixture was stirred overnight, quenched with acetic acid, and concentrated. The crude product was triturated with water to give 496 mg of {5-[2-(3-Hydroxymethyl-phenylamino)-pyrimidin-4-yl]-thiophen-2-yl}-acetic acid as an orange solid (1.45 mmol, 90%).

{5-[2-(3-Hydroxymethyl-phenylamino)-pyrimidin-4-yl]-thiophen-2-yl}-acetic acid was converted to 2-{5-[2-(3-Hydroxymethyl-phenylamino)-pyrimidin-4-yl]-thiophen-2-yl}-N-methyl-N-phenyl-acetamide following method 3, steps 1 and 2. MS: m/z 431 (M+H$^+$).

Method 21:

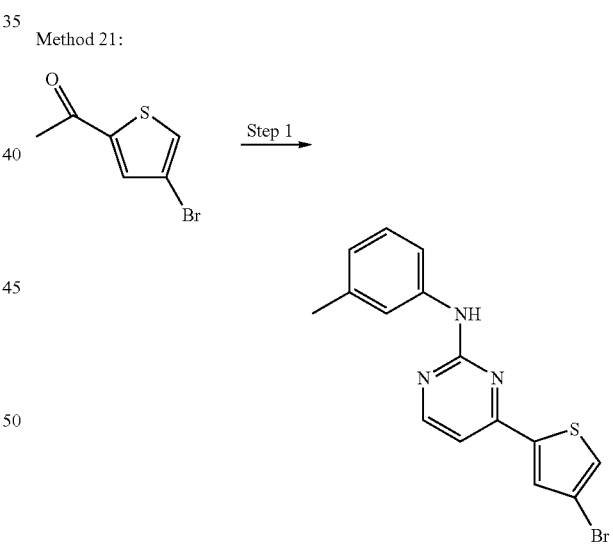

Synthesis of [4-(4-(Bromo-thiophen-2-yl)-pyrimidin-2-yl]-m-tolyl amine

[4-(4-(Bromo-thiophen-2-yl]-m-tolyl amine was prepared according to method 3, steps 1 and 2, from commercially available 1-(4-Bromo-thiophen-2-yl)-ethanone. MS: m/z 346 (M+H$^+$). $^1$H NMR (500 MHz, DMSO-d6) δ 2.30 (s, 3H), 6.77 (d, J=7.5 Hz, 1H), 7.17 (t, J=8 Hz, 1H), 7.37 (d, J=5.5 Hz, 1H), 7.53 (br d, J=8 Hz, 1H), 7.71 (s, 1H), 7.92 (d, J=1.5 Hz, 1H), 8.07 (d, J=1.5 Hz, 1H), 8.51 (d, J=5.5 Hz, 1H), 9.64 (s, 1H).

Method 22:

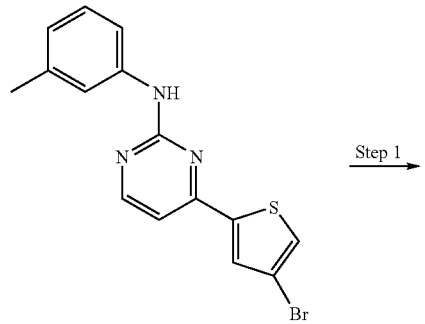

Synthesis of {4-[4-(2,6-Dimethylphenyl)-thiophen-2-yl]-pyrimidin-2-yl}-m-tolyl amine {4-[4-(2,6-Dimethylphenyl)-thiophen-2-yl]-pyrimidin-2-yl}-m-tolyl amine was prepared according to method 5. MS: m/z 373 (M+H$^+$). $^1$H NMR (500 MHz, DMSO-d6) δ 2.09 (s, 6H), 2.32 (s, 3H), 6.77 (d, J=7 Hz, 1H), 7.11-7.19 (m, 4H), 7.35 (d, J=5 Hz, 1H), 7.57 (br d, J=8.5 Hz, 1H), 7.60 (d, J=1.5 Hz, 1H), 7.80 (br s, 1H), 7.92 (d, J=1.5 Hz, 1H), 8.46 (d, J=5 Hz, 1H), 9.58 (s, 1H).

Method 23:

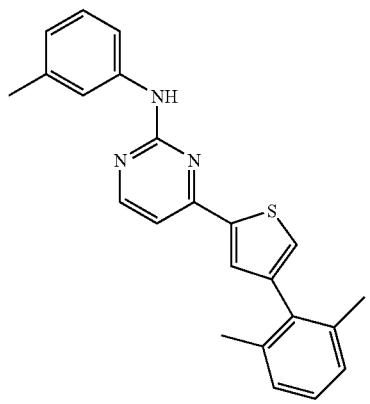

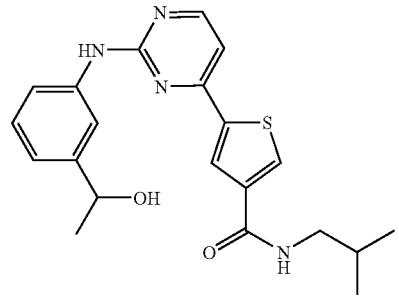

Synthesis of 5-{2-[3-(1-Hydroxy-ethyl)-phenylamino]-pyrimidin-4-yl}-thiophene-3-carboxylic acid isobutyl-amide A 5 mL Personal Chemistry™ microwave vial was charged with 1-{3-[4-(4-Bromo-thiophen-2-yl)-pyrimidin-2-ylamino]-phenyl}-ethanol (149.3 mg, 0.40 mmol, prepared according to Method 22), isobutylamine (120 uL, 1.20 mmol), molybdenum hexacarbonyl (109.2 mg, 0.41 mmol), THF (2 mL), 20 mg (0.02 mmol) of Hermann's Palladacycle [trans-di-mu-acetatobis[2-9di-O-tolylphosphino)benzyl]dipalladium(II)], and DBU (180 uL, 1.20 mmol). The reaction mixture was heated to 150° C. in a microwave reactor for 15 min. The crude reaction mixture was diluted with DMSO (2 mL), filtered through a plug of silica gel, then purified by mass-triggered reverse-phase HPLC, (C-18; eluting with a 5-95% gradient consisting of 0.1% formic acid in water: 0.1% formic acid in ACN). Lyophilization of the purified fraction provided 39.5 mg (25% yield) of 5-{2-[3-(1-Hydroxy-ethyl)-phenylamino]-pyrimidin-4-yl}-thiophene-3-carboxylic acid isobutyl-amide as a white powder. $^1$H NMR (d$_6$-DMSO) δ 9.49 (br. s, 1H), 8.34 (d, J=5.0 Hz, 1H), 8.20 (t, J=6.0 Hz, 1H), 8.16 (dd, J=6.0, 0.5 Hz, 1H), 7.67 (br.s, 1H), 7.49 (dd, J=5.0, 1.2 Hz, 1H), 7.15 (d, J=5.0 Hz, 1H), 7.09 (t, J=7.5 Hz, 1H), 6.80 (d, J=7.5 Hz, 1H), 4.97 (br.d, J=3.5 Hz, 1H), 4.55 (qrt, J=5.5 Hz, 1H), 2.91 (t, J=6.5 Hz, 2H), 1.67 (m, 1H), 1.19 (d, J=6.0 Hz, 3H), 0.74 (d, J=7.0 Hz, 6H); HPLC/MS m/z: 397 [MH]$^+$.

TABLE 17

Other compounds prepared by method 23:

| Structure | M + H |
|---|---|
| 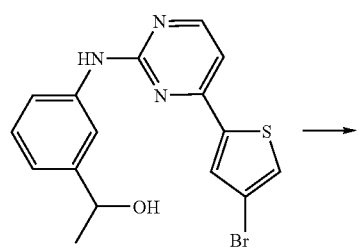 | 355 |

TABLE 17-continued

Other compounds prepared by method 23:

| Structure | M + H |
|---|---|
| (structure) | 369 |
| (structure) | 383 |
| (structure) | 397 |
| (structure) | 397 |
| (structure) | 411 |
| (structure) | 395 |
| (structure) | 409 |
| (structure) | 431 |
| (structure) | 432 |

TABLE 17-continued

Other compounds prepared by method 23:

| Structure | M + H |
|---|---|
| (structure) | 369 |
| (structure) | 445 |
| (structure) | 438 |

Example 2

Bioassays

Kinase assays known to those of skill in the art may be used to assay the inhibitory activities of the compounds and compositions of the present invention. Kinase assays include, but are not limited to, the following examples.

Screening data was evaluated using the equation: $Z'=1-[3*(\sigma_+ +\sigma_-)/|\mu_+ -\mu_-|]$ (Zhang, et al., 1999 J Biomol Screening 4(2) 67-73), where $\mu$ denotes the mean and $\sigma$ the standard deviation. The subscript designates positive or negative controls. The Z' score for a robust screening assay should be $\geq 0.50$. The typical threshold=$\mu_+ - 3*\sigma_+$. Any value that falls below the threshold was designated a "hit".

MET Luminescence-Based ATP Depletion Enzyme Assay

Materials: Poly Glu-Tyr (4:1) substrate (Sigma Cat#P-0275), ATP (Sigma Cat#A-3377, FW=551), HEPES buffer, pH 7.5, Bovine serum albumin (BSA) (Roche 92423420), MgCl$_2$, Staurosporine (*Streptomyces* sp. Sigma Cat#85660-1MG), white Costar 384-well flat-bottom plate (VWR Cat#29444-088). MET kinase (see below), Kinase-Glo™ (Promega Cat#V6712).

Stock Solutions: 10 mg/ml poly Glu-Tyr in water, stored at −20° C.; 100 mM HEPES buffer, pH 7.5 (5 ml 1M stock+45 ml miliQH$_2$O); 10 mM ATP (5.51 mg/ml in dH$_2$O) stored at −20° C. (diluted 50 µl into total of 10 ml miliQH$_2$O daily=50 µM ATP working stock); 1% BSA (1 g BSA in 100 ml 0.1M HEPES, pH 7.5, stored at −20° C.), 100 mM MgCl$_2$; 200 µM Staurosporine, 2× Kinase-Glo™ reagent (made fresh or stored at −20° C.).

Standard Assay Setup for 384-well format (20 µl kinase reaction, 40 µl detection reaction): 10 mM MgCl$_2$; 0.3 mg/ml poly Glu-Tyr; 0.1% BSA; 1 µl test compound (in DMSO); 0.4 µg/ml MET kinase; 10 µM ATP; 100 mM HEPES buffer. Positive controls contained DMSO with no test compound. Negative controls contained 10 µM staurosporine. The kinase reactions were initiated at time t=0 by the addition of ATP. Kinase reactions were incubated at 21° C. for 60 min, then 20 µl of Kinase-Glo™ reagent were added to each well to quench the kinase reaction and initiate the luminescence reaction. After a 20 min incubation at 21° C., the luminescence was detected in a plate-reading luminometer.

AurA Luminescence-Based ATP Depletion Enzyme Assay

Materials: Kemptide peptide substrate=LRRASLG (Biopeptide, San Diego, Calif.), ATP (Sigma Cat#A-3377, FW=5551), HEPES buffer, pH 7.5, 10% Brij 35 (Calbiochem Cat#203728), MgCl$_2$, Staurosporine (*Streptomyces* sp. Sigma Cat#85660-1MG), white Costar 384-well flat-bottom plate (VWR Cat#29444-088), Autophosphorylated AurA kinase (see below), Kinase-Glo™ (Promega Cat#V6712).

Stock Solutions: 10 mM Kemptide peptide (7.72 mg/ml in water), stored at −20° C.; 100 mM HEPES buffer+0.015% Brij 35, pH 7.5 (5 ml 1M HEPES stock+75 µL 10% Brij 35+45 ml miliQH$_2$O); 10 mM ATP (5.51 mg/ml in dH$_2$O) stored at −20° C. (diluted 50 µl into total of 10 ml miliQH$_2$O daily=50 µM ATP working stock); 100 mM MgCl$_2$; 200 µM Staurosporine, 2× Kinase-Glo™ reagent (made fresh or stored at −20° C.).

AurA Autophosphorylation Reaction: ATP and MgCl$_2$ were added to 1-5 mg/ml AurA at final concentrations of 10 mM and 100 mM, respectively. The autophosphorylation reaction was incubated at 21° C. for 2-3 h. The reaction was stopped by the addition of EDTA to a final concentration of 50 mM, and samples were flash frozen with liquid N$_2$ and stored at −80° C.

Standard Assay Setup for 384-well format (20 µl kinase reaction, 40 µl detection reaction): 10 mM MgCl$_2$; 0.2 mM Kemptide peptide; 1 µl test compound (in DMSO); 0.3 µg/ml Autophosphorylated AurA kinase; 10 µM ATP; 100 mM HEPES+0.015% Brij buffer. Positive controls contained DMSO with no test compound. Negative controls contained 5 µM staurosporine. The kinase reactions were initiated at time t=0 by the addition of ATP. Kinase reactions were incubated at 21° C. for 45 min, then 20 µl of Kinase-Glo™ reagent were added to each well to quench the kinase reaction and initiate the luminescence reaction. After a 20 min incubation at 21° C., the luminescence was detected in a plate-reading luminometer.

JAK2 Luminescence-Based ATP Depletion Enzyme Assay

Materials: JAK3tide peptide substrate=GGEEEEYFELVKKKK (Biopeptide, San Diego, Calif.), ATP (Sigma Cat#A-3377, FW=551), HEPES buffer, pH 7.6, 10% Brij 35 (Calbiochem Cat#203728), MgCl$_2$, Staurosporine (*Streptomyces* sp. Sigma Cat#85660-1MG), white Corning (Costar) 384-well flat bottom plate (VWR Cat#29444-088), JAK2 KD (kinase domain) or JAK2 JH1JH2 V617F kinase (see below), Kinase-Glo™ (Promega Cat#V6712).

Stock Solutions: 5 mM JAK3tide peptide (9.86 mg/ml in 100 mM HEPES, pH 7.6), stored at −20° C.; 100 mM HEPES buffer, pH 7.6, 10% Brij 35; 10 mM ATP (5.51 mg/ml in 100 mM HEPES, pH 7.6) stored at −20° C. (diluted 50 µl into total of 10 ml 100 mM HEPES, pH 7.6, daily=50 µM ATP working stock); 100 mM $MgCl_2$; 200 µM Staurosporine, 2× Kinase-Glo™ reagent (made fresh or stored at −20° C.).

Standard Assay Conditions for 384-well format (20 µl kinase reaction, 40 µl detection reaction): 10 mM $MgCl_2$; 0.1 mM JAK3tide peptide (or, 0.5 mM JAK3tide peptide for JAK2 JH1JH2 V617F assay); 1 µl test compound (in 100% DMSO); 0.4 µg/ml JAK2 KD kinase or 12 µg/ml JAK2 JH1JH2 V617F kinase; 10 µM ATP; 100 mM HEPES+0.01% Brij, pH 7.6. Positive controls contained 5% DMSO with no test compound. Negative controls contained 10 µM staurosporine. The kinase reactions were initiated at time t=0 by the addition of ATP. Kinase reactions were incubated at 21-23° C. for 30 min, after which 20 µl of Kinase-Glo™ reagent were added to each well to quench the kinase reaction and initiate the luminescence reaction. After a 20 min incubation at 21-23° C., the luminescence was detected in a plate-reading luminometer (Tecan Ultra Evolution).

Purification of Met:

The cell pellets produced from half of a 12 L Sf9 insect cell culture expressing the kinase domain of human Met were resuspended in a buffer containing 50 mM Tris-HCl pH 7.7 and 250 mM NaCl, in a volume of approximately 40 ml per 1 L of original culture. One tablet of Roche Complete, EDTA-free protease inhibitor cocktail (Cat#1873580) was added per 1 L of original culture. The suspension was stirred for 1 hour at 4° C. Debris was removed by centrifugation for 30 minutes at 39,800×g at 4° C. The supernatant was decanted into a 500 ml beaker and 10 ml of 50% slurry of Qiagen Ni-NTA Agarose (Cat#30250) that had been pre-equilibrated in 50 mM Tris-HCl pH 7.8, 50 mM NaCl, 10% Glycerol, 10 mM Imidazole, and 10 mM Methionine, were added and stirred for 30 minutes at 4° C. The sample was then poured into a drip column at 4° C. and washed with 10 column volumes of 50 mM Tris-HCl pH 7.8, 500 mM NaCl, 10% Glycerol, 10 mM Imidazole, and 10 mM Methionine. The protein was eluted using a step gradient with two column volumes each of the same buffer containing 50 mM, 200 mM, and 500 mM Imidazole, sequentially. The 6× Histidine tag was cleaved overnight using 40 units of TEV protease (Invitrogen Cat#10127017) per 1 mg of protein while dialyzing in 50 mM Tris-HCl pH 7.8, 500 mM NaCl, 10% Glycerol, 10 mM Imidazole, and 10 mM Methionine at 4° C. The 6× Histidine tag was removed by passing the sample over a Pharmacia 5 ml IMAC column (Cat#17-0409-01) charged with Nickel and equilibrated in 50 mM Tris-HCl pH 7.8, 500 mM NaCl, 10% Glycerol, 10 mM Imidazole, and 10 mM Methionine. The cleaved protein bound to the Nickel column at a low affinity and was eluted with a step gradient. The step gradient was run with 15% and then 80% of the B-side (A-side=50 mM Tris-HCl pH 7.8, 500 mM NaCl, 10% Glycerol, 10 mM Imidazole, and 10 mM Methionine; B-side=50 mM Tris-HCl pH 7.8, 500 mM NaCl, 10% Glycerol, 500 mM Imidazole, and 10 mM Methionine) for 4 column volumes each. The Met protein eluted in the first step (15%), whereas the non-cleaved Met and the cleaved Histidine tag eluted in the 80% fractions. The 15% fractions were pooled after SDS-PAGE gel analysis confirmed the presence of cleaved Met; further purification was done by gel filtration chromatography on an Amersham Biosciences HiLoad 16/60 Superdex 200 prep grade (Cat#17-1069-01) equilibrated in 50 mM Tris-HCl pH 8.5, 150 mM NaCl, 10% Glycerol and 5 mM DTT. The cleanest fractions were combined and concentrated to ~10.4 mg/ml by centrifugation in an Amicon Ultra-15 10,000 Da MWCO centrifugal filter unit (Cat#UFC901024).

Purification of AurA:

The Sf9 insect cell pellets (~18 g) produced from 6 L of cultured cells expressing human Aurora-2 were resuspended in 50 mM Na Phosphate pH 8.0, 500 mM NaCl, 10% glycerol, 0.2% n-octyl-β-D-glucopyranoside (BOG) and 3 mM β-Mercaptoethanol (BME). One tablet of Roche Complete, EDTA-free protease inhibitor cocktail (Cat#1873580) and 85 units Benzonase (Novagen Cat#70746-3)) were added per 1 L of original culture. Pellets were resuspended in approximately 50 ml per 1 L of original culture and were then sonicated on ice with two 30-45 sec bursts (100% duty cycle). Debris was removed by centrifugation and the supernatant was passed through a 0.8 µm syringe filter before being loaded onto a 5 ml $Ni^{2+}$ HiTrap column (Pharmacia). The column was washed with 6 column volumes of 50 mM Na Phosphate pH 8.0, 500 mM NaCl, 10% glycerol, 3 mM BME. The protein was eluted using a linear gradient of the same buffer containing 500 mM Imidazole. The eluant (24 ml) was cleaved overnight at 4° C. in a buffer containing 50 mM Na Phosphate pH 8.0, 500 mM NaCl, 10% glycerol, 3 mM BME and 10,000 units of TEV (Invitrogen Cat#10127-017). The protein was passed over a second nickel affinity column as described above; the flow-through was collected. The cleaved protein fractions were combined and concentrated using spin concentrators. Further purification was done by gel filtration chromatography on a S75 sizing column in 50 mM Na Phosphate (pH 8.0), 250 mM NaCl, 1 mM EDTA, 0.1 mM AMP-PNP or ATP buffer, and 5 mM DTT. The cleanest fractions were combined and concentrated to approximately 8-11 mg/ml, and were either flash frozen in liquid nitrogen in 120 µl aliquots and stored at −80° C., or stored at 4° C.

Purification of Jak2:

The pellet of Sf9 insect cells produced from a 6 L expression of Jak2 was resuspended in a buffer containing 50 mM Tris-HCl pH 8.5, 250 mM NaCl, 5% Glycerol, 0.2% β-octyl-glucoside, 5 mM β-mercaptoethanol (or with ligand added to the buffer eg. 5 mM ATP and 10 mM MgCl2; 0.05 mM compound of the invention) in a volume of approximately 40 mL per 1 L of original culture. One tablet of Roche Complete, EDTA-free protease inhibitor cocktail (Cat. #1873580) was added per 1 L of original culture. The suspension was then stirred for 1 hour at 4° C. Debris was removed by centrifugation for 30 minutes at 39,800 g at 4° C. The supernatant was decanted into a 500 mL beaker and 10 mL of 50% Qiagen Ni-NTA Agarose (Cat. #30250) pre-equilibrated in 50 mM Tris-HCl pH 8.5, 250 mM NaCl, 5% Glycerol, 0.2% β-octyl-glucoside, 5 mM β-mercaptoethanol was added and stirred for 30 minutes at 4° C. The sample was poured through a drip column at 4° C. and washed with 10 column volumes (CV) of 50 mM Tris-HCl pH 8.5, 250 mM NaCl, 5% Glycerol, 0.2% β-octylglucoside, 5 mM β-mercaptoethanol. The protein was eluted in 5 mL fractions using 5 CV of the same buffer containing 250-500 mM Imidazole. Fractions were pooled by SDS-PAGE analysis and the protein concentration determined by a Bradford assay. 5 mM TCEP was added to the pool and the protein sample was concentrated to ~8 mL by centrifugation in an Amicon Ultra-15 10,000 Da MWCO centrifugal filter unit (Cat. #UFC901024). The concentrated protein was applied to a GE Healthcare HiLoad 16/60 Superdex 75 or 200 prep grade column (Cat. #17-1068-01, Cat.

17-1069-01) equilibrated in 20 mM Tris-HCl pH 8.5, 250 mM NaCl, and 1 mM DTT. Fractions were run on a SDS-PAGE gel and the cleanest fractions were pooled. The protein was concentrated to approximately 6.5-10 mg/mL. Samples in the final buffer (20 mM Tris-HCl pH 8.5, 250 mM NaCl, 1 mM DTT; [or with ligand added eg. 2 mM ATP/5 mM MgCl2 or 0.05 mM compound of the invention]) are delivered fresh to crystallization and stored at 4° C. or flash frozen in liquid nitrogen (as 120 μL aliquots) and stored at −80° C.

Example 3

Cell Assays

HCT116 cells were maintained in McCoy's 5a Medium supplemented with 10% fetal bovine serum (FBS) 2 mM L-Glutamine and 100 units penicillin/100 μg streptomycin, at 37° C. in 5% $CO_2$.

Cell Survival Assays

Compounds were tested in the following assays in duplicate.

96-well XTT assay: Cells were grown in growth media containing various concentrations of compounds (duplicates) on a 96-well flat bottom plate for 72 hours at 37° C. in 5% $CO_2$. The starting cell number was 5000 cells per well and volume was 120 μl. At the end of the 72-hour incubation, 40 μl of XTT labeling mixture (50:1 solution of sodium 3'-[1-(phenylaminocarbonyl)-3,4-tetrazolium]-bis(4-methoxy-6-nitro) benzene sulfonic acid hydrate and Electron-coupling reagent: PMS (N-methyl dibenzopyrazine methyl sulfate) were added to each well of the plate. After an additional 2-6 hours of 650 nm was measured with a spectrophotometer.

Histone-H3 phosphorylation assay: HCT116 cells were plated out at 1×10^6 cells per 60×15 mm dish (Falcon) in 3 mL of growth media (McCoy's 5A Media, 10% FBS, 1% pen-strep) and incubated overnight (37° C. 5% CO2). The next day compound was added and incubated for 1 hr (37° C. 5% CO2). After 1 hr, the cells were washed once with 1×PBS, and then lysed directly on the plate with 100 μL of lysis buffer (125 mM Tris HCl pH 6.8 and 2×

SDS loading buffer) and transferred to a 1.7 mL eppendorf tube and put on ice. The samples were sonicated for approximately 5 seconds and were put in a 95° C. heat block for 3 minutes. After heating, the samples were loaded on a NuPage 4-12% Bis-Tris Gel (Invitrogen), followed by electrophoretic transfer to 0.45 μm nitrocellulose membranes (Invitrogen). After transferring, the membranes were placed in Qiagen blocking buffer with 0.1% Tween for 1 hour at room temperature with gentle rocking. Anti-phospho-Histone H3 (Ser10) antibody (Upstate #06-570), was diluted 1:250 in blocking buffer and was added to the blots and incubated for 1 hour at room temperature. The blot was then washed three times with 1×PBS+0.1% Tween20. Goat-anti Rabbit HRP secondary antibody (Jackson ImmunoResearch Laboratories, Inc. #111-035-003) was diluted 1:3000 in blocking buffer, and was then added for 1 hr at room temperature. The blot was washed three times with 1×PBS+0.1% Tween20, and visualized by chemiluminescence with SuperSignal West Pico Chemiluminescent Substrate (Pierce #34078).

The activities for selected compounds are listed in Table 18

TABLE 18

| Activities for selected compounds: | | | | | |
|---|---|---|---|---|---|
| Structure | AurA enzyme IC50 A < 0.1 μM 0.1 μM < B < 0.5 μM C > 0.5 μM | AurA XTT IC50 D < 1 μM 1 μM < E < 5 μM | MET enzyme IC50 F < 1 μM 1 μM < G < 5 μM | JAK2-WT enzyme IC50 H < 0.1 μM | JAK2-V617F enzyme IC50 I < 0.5 μM |
| 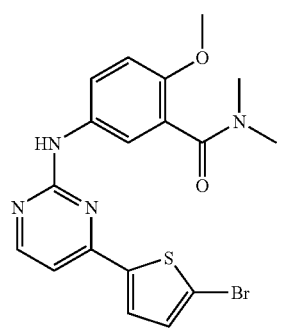 | B | E | G | | |

TABLE 18-continued

Activities for selected compounds:

| Structure | AurA enzyme IC50 A < 0.1 µM 0.1 µM < B < 0.5 µM C > 0.5 µM | AurA XTT IC50 D < 1 µM 1 µM < E < 5 µM | MET enzyme IC50 F < 1 µM 1 µM < G < 5 µM | JAK2-WT enzyme IC50 H < 0.1 µM | JAK2-V617F enzyme IC50 I < 0.5 µM |
|---|---|---|---|---|---|
| | B | D | | H | I |
| | B | E | G | H | |
| | B | | F | | |

TABLE 18-continued
Activities for selected compounds:
| Structure | AurA enzyme IC50 A < 0.1 µM 0.1 µM < B < 0.5 µM C > 0.5 µM | AurA XTT IC50 D < 1 µM 1 µM < E < 5 µM | MET enzyme IC50 F < 1 µM 1 µM < G < 5 µM | JAK2-WT enzyme IC50 H < 0.1 µM | JAK2-V617F enzyme IC50 I < 0.5 µM |
|---|---|---|---|---|---|
| 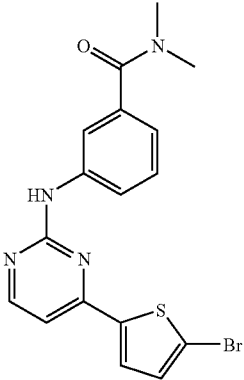 | B | | G | | |
| 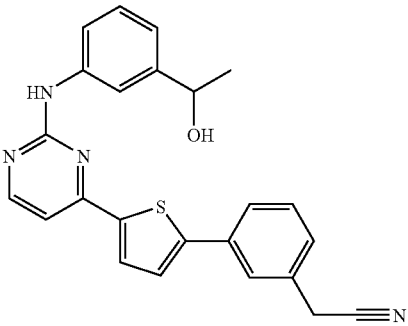 | B | | | H | I |
| 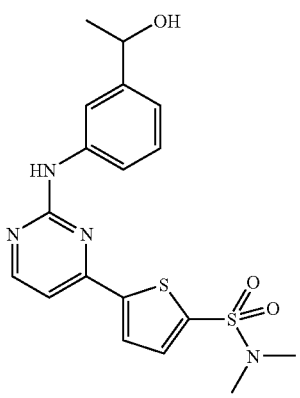 | A | E | G | H | I |

TABLE 18-continued

Activities for selected compounds:

| Structure | AurA enzyme IC50 A < 0.1 μM 0.1 μM < B < 0.5 μM C > 0.5 μM | AurA XTT IC50 D < 1 μM 1 μM < E < 5 μM | MET enzyme IC50 F < 1 μM 1 μM < G < 5 μM | JAK2-WT enzyme IC50 H < 0.1 μM | JAK2-V617F enzyme IC50 I < 0.5 μM |
|---|---|---|---|---|---|
| | B | | | H | I |
| 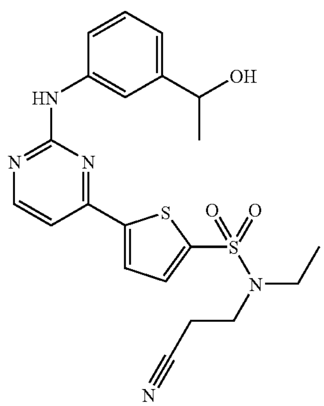 | A | E | F | H | I |
| | B | | | | |
| | B | E | G | H | |

TABLE 18-continued
Activities for selected compounds:
| Structure | AurA enzyme IC50 A < 0.1 μM 0.1 μM < B < 0.5 μM C > 0.5 μM | AurA XTT IC50 D < 1 μM 1 μM < E < 5 μM | MET enzyme IC50 F < 1 μM 1 μM < G < 5 μM | JAK2-WT enzyme IC50 H < 0.1 μM | JAK2-V617F enzyme IC50 I < 0.5 μM |
|---|---|---|---|---|---|
| 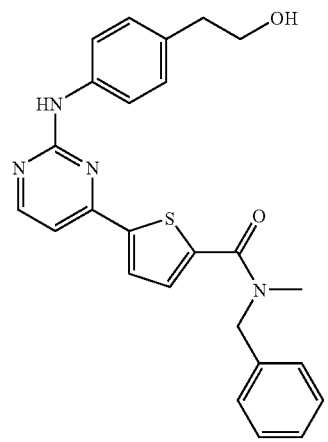 | A | E | | H | |
| 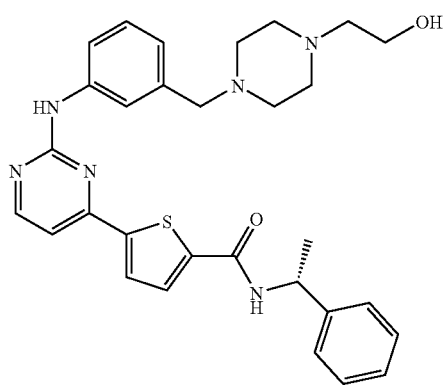 | A | D | F | H | |
| 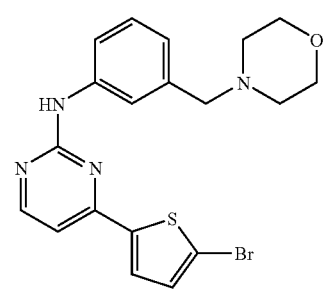 | C | | G | | |

TABLE 18-continued

Activities for selected compounds:

| Structure | AurA enzyme IC50 A < 0.1 µM 0.1 µM < B < 0.5 µM C > 0.5 µM | AurA XTT IC50 D < 1 µM 1 µM < E < 5 µM | MET enzyme IC50 F < 1 µM 1 µM < G < 5 µM | JAK2-WT enzyme IC50 H < 0.1 µM | JAK2-V617F enzyme IC50 I < 0.5 µM |
|---|---|---|---|---|---|
| | C | | G | H | |
| | B | E | G | | |
| | B | | | H | |
| | C | E | | | |

TABLE 18-continued

Activities for selected compounds:

| Structure | AurA enzyme IC50 A < 0.1 μM 0.1 μM < B < 0.5 μM C > 0.5 μM | AurA XTT IC50 D < 1 μM 1 μM < E < 5 μM | MET enzyme IC50 F < 1 μM 1 μM < G < 5 μM | JAK2-WT enzyme IC50 H < 0.1 μM | JAK2-V617F enzyme IC50 I < 0.5 μM |
|---|---|---|---|---|---|
| *structure* | A | E | F | H | I |
| *structure* | A | E | G | H | I |
| *structure* | B | | | | |

TABLE 18-continued
| | Activities for selected compounds: | | | | |
|---|---|---|---|---|---|
| Structure | AurA enzyme IC50 A < 0.1 µM 0.1 µM < B < 0.5 µM C > 0.5 µM | AurA XTT IC50 D < 1 µM 1 µM < E < 5 µM | MET enzyme IC50 F < 1 µM 1 µM < G < 5 µM | JAK2-WT enzyme IC50 H < 0.1 µM | JAK2-V617F enzyme IC50 I < 0.5 µM |
| 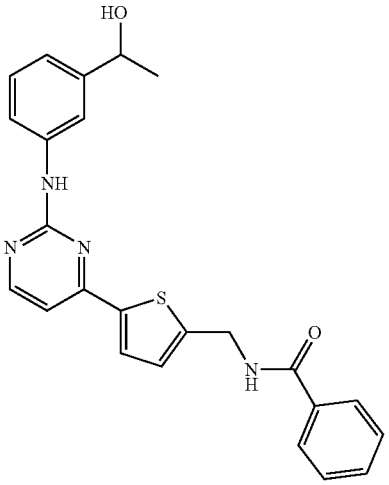 | B | | | | |
| 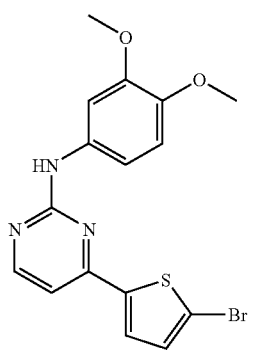 | A | | G | | |
| 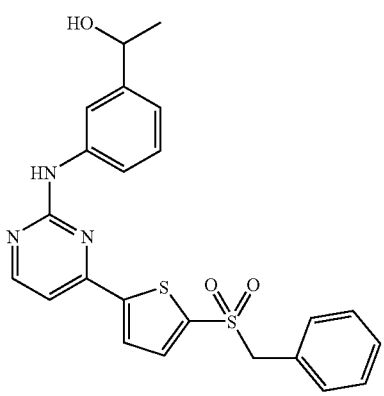 | B | | F | H | |

TABLE 18-continued

Activities for selected compounds:

| Structure | AurA enzyme IC50 A < 0.1 μM 0.1 μM < B < 0.5 μM C > 0.5 μM | AurA XTT IC50 D < 1 μM 1 μM < E < 5 μM | MET enzyme IC50 F < 1 μM 1 μM < G < 5 μM | JAK2-WT enzyme IC50 H < 0.1 μM | JAK2-V617F enzyme IC50 I < 0.5 μM |
|---|---|---|---|---|---|
| (structure) | A | D | F | H | I |
| (structure) | A | | | | |
| (structure) | C | | | H | |
| (structure) | A | | G | H | I |

TABLE 18-continued
Activities for selected compounds:
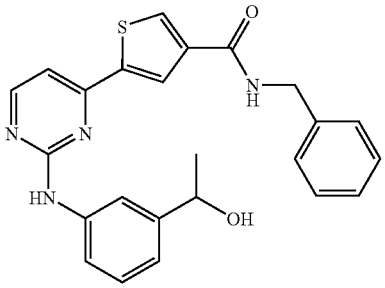
What is claimed is:
1. A compound, or salt thereof, selected from
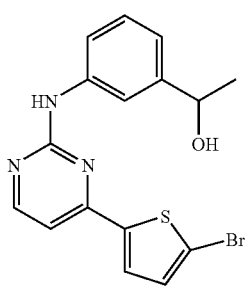
403/405
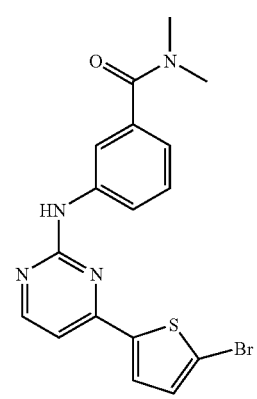
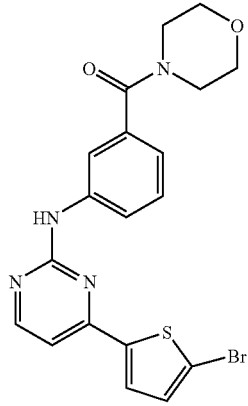
445/447
-continued
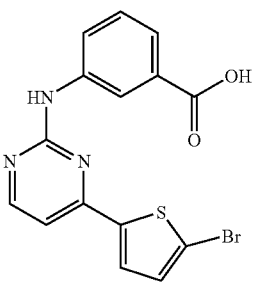
376/378

-continued
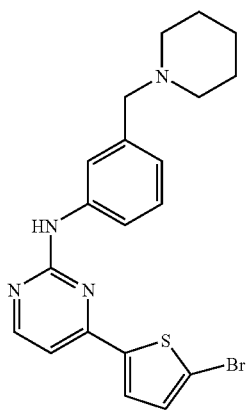 429/431
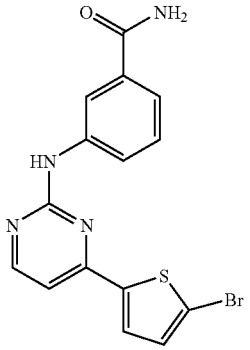 374/376
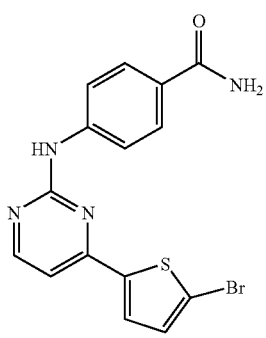 474/476
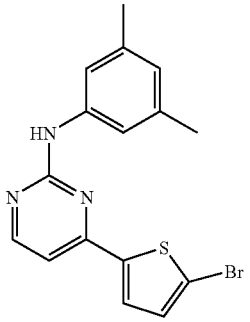 372/374
-continued
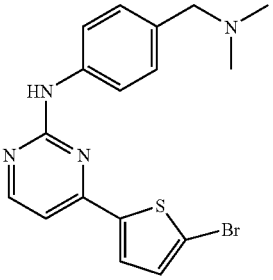 375/377
362/364
375/377
360/362
389/391

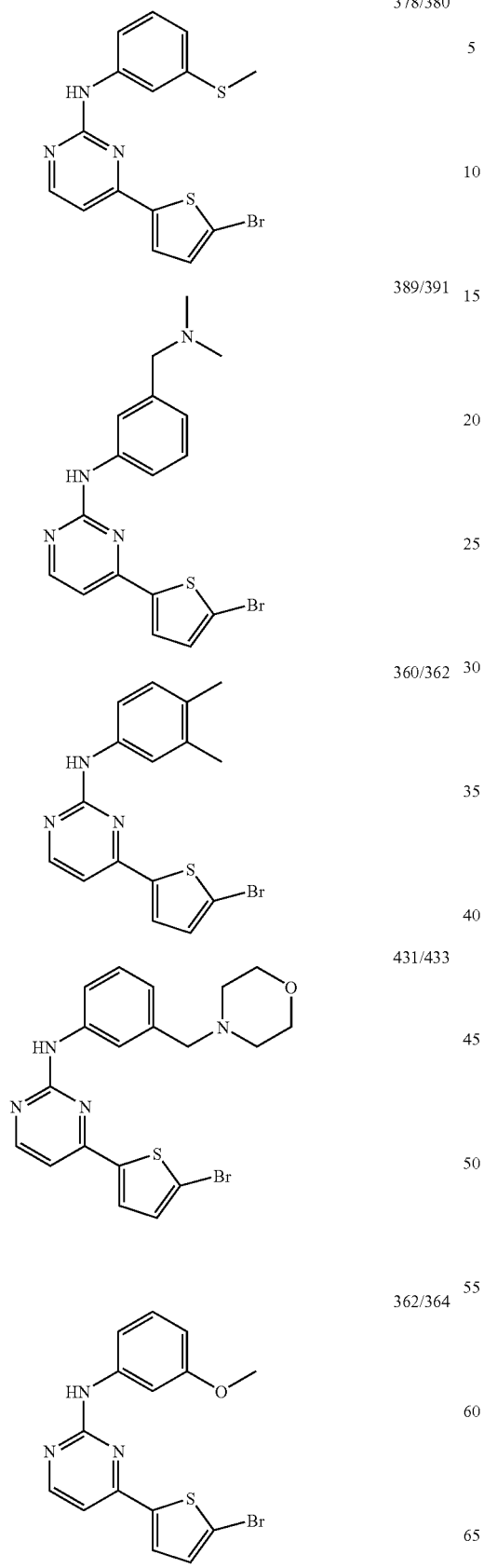
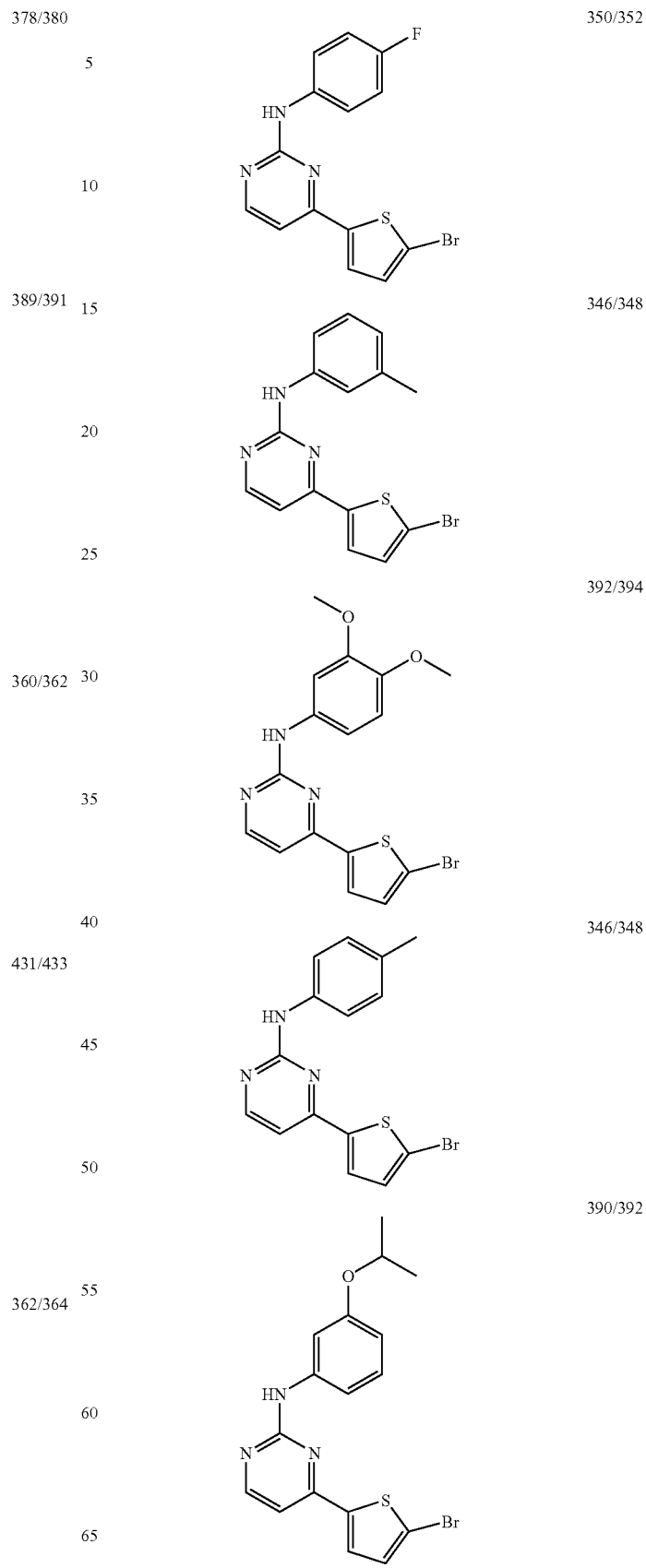

-continued
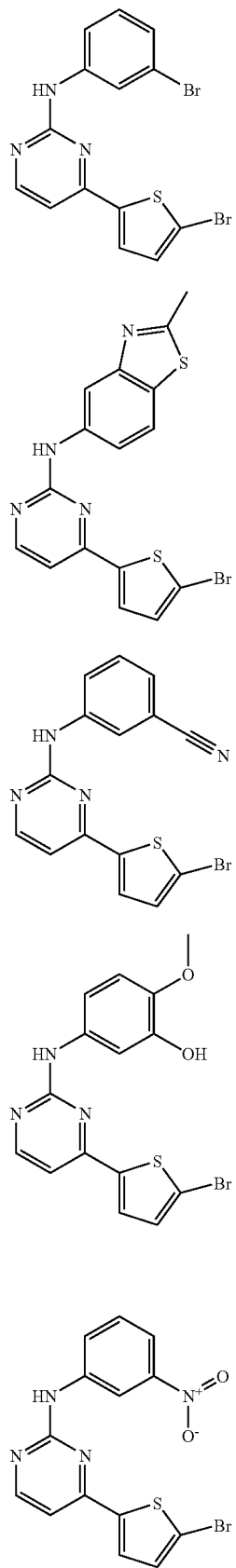
410/413
403/405
357/359
378/380
377/379
-continued
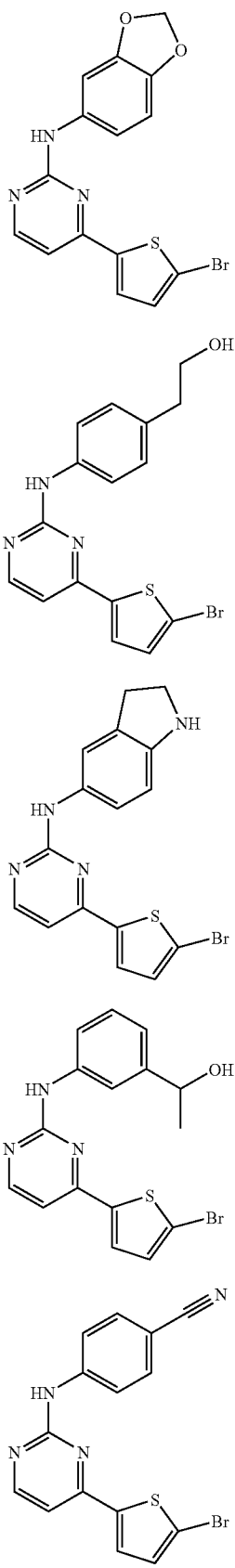
376/378
376/378
371/373
376/378
357/359

-continued
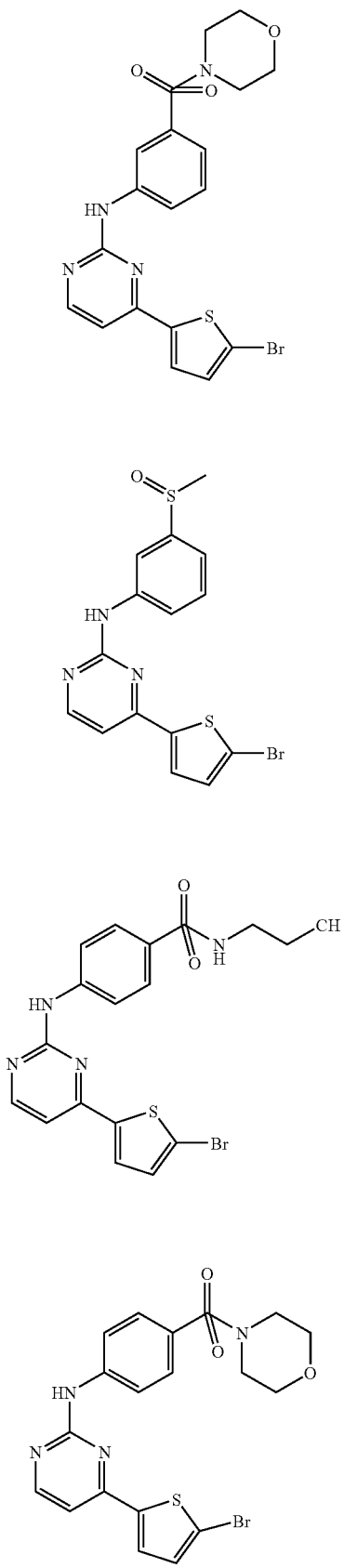
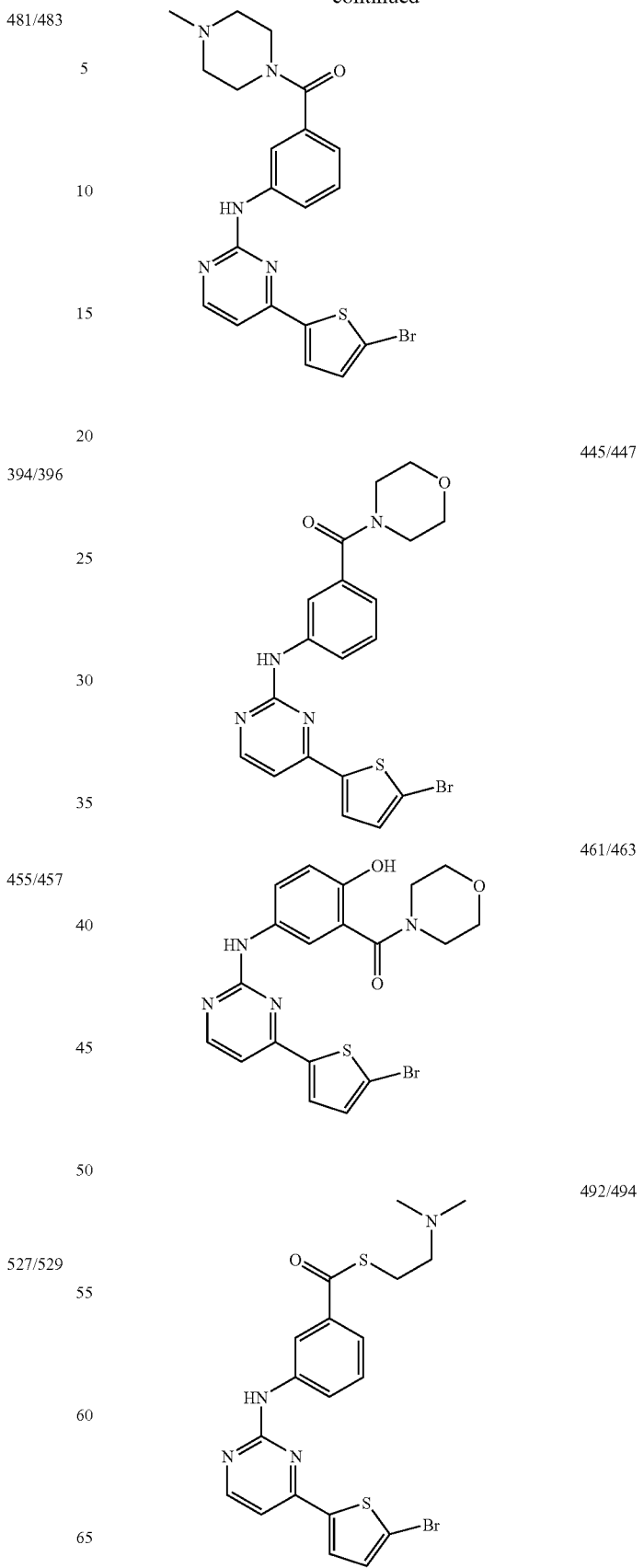
481/483
394/396
455/457
527/529
445/447
461/463
492/494

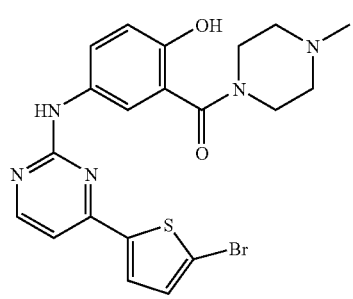 474/476
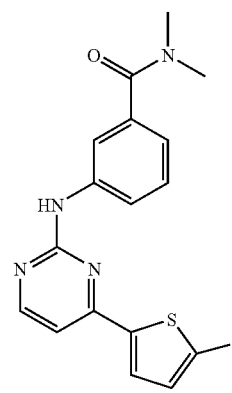 403/405
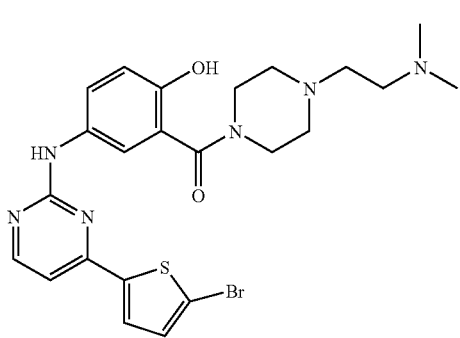 531/533
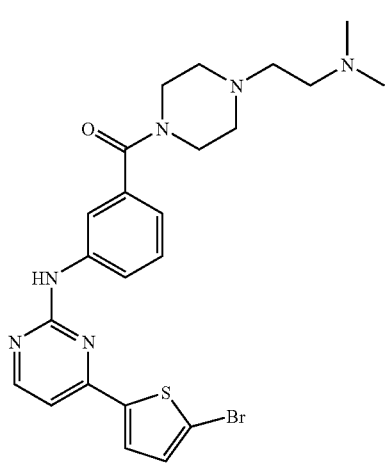 515/517
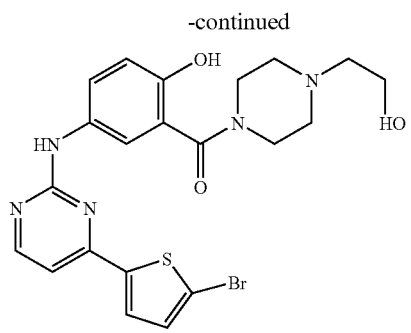 504/506
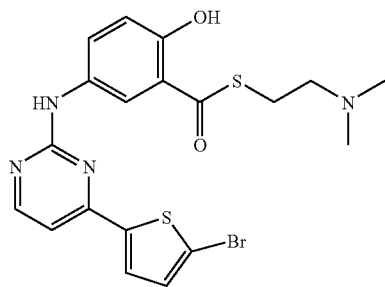 462-464
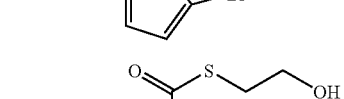 419/421
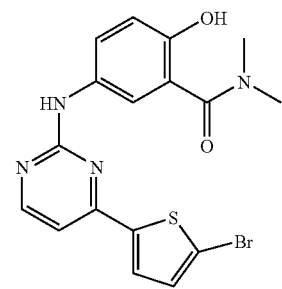 419/421
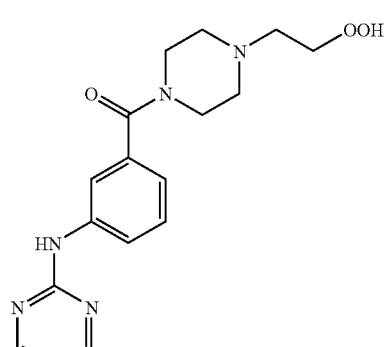 488/490

-continued
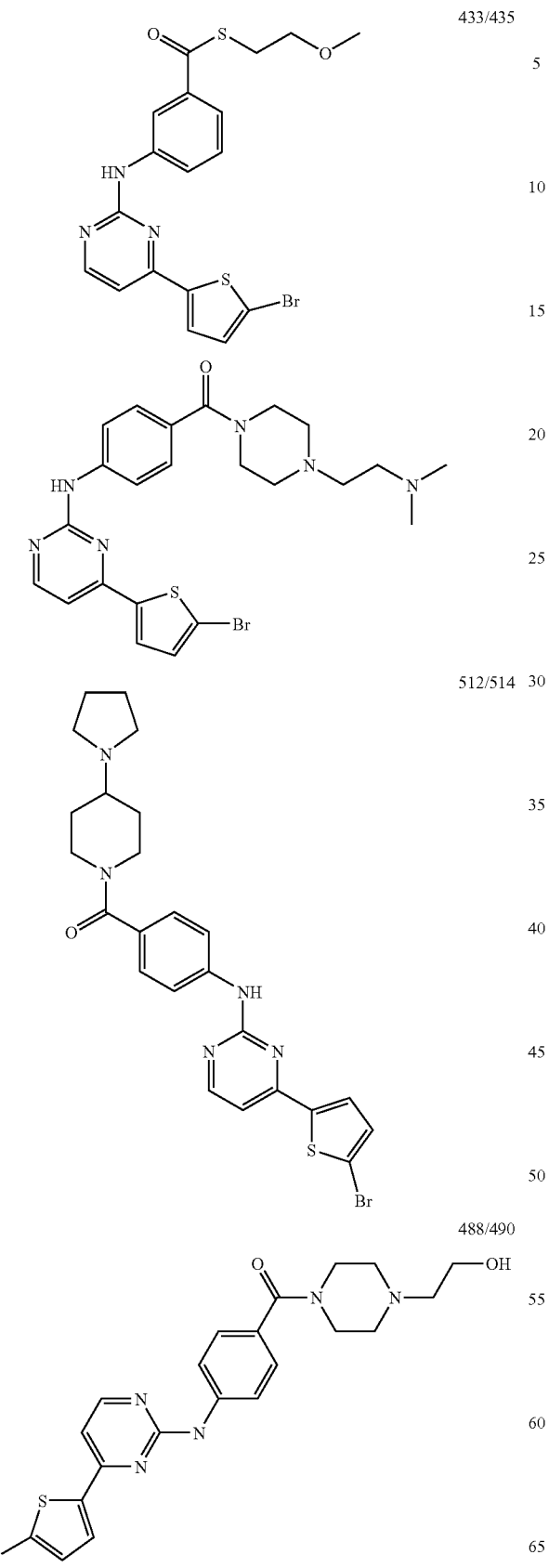
433/435
512/514
488/490
-continued
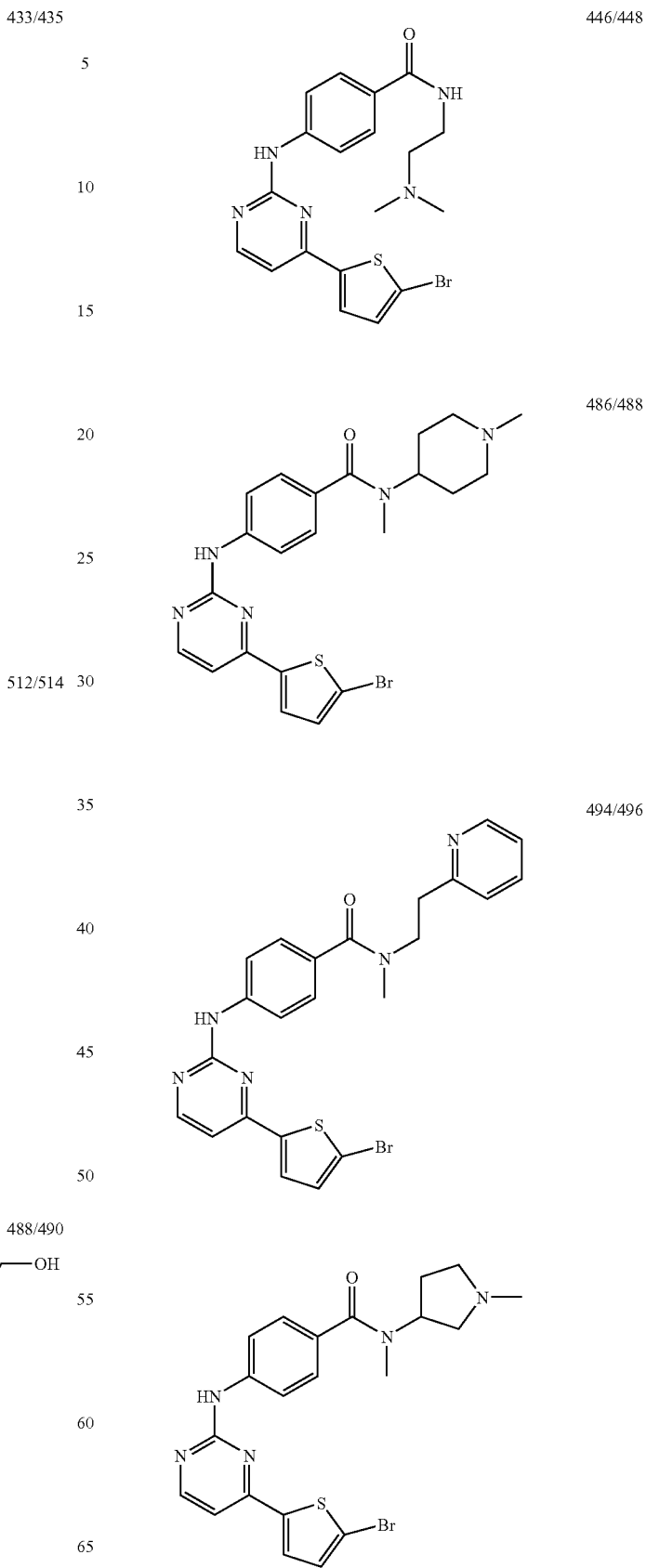
446/448
486/488
494/496

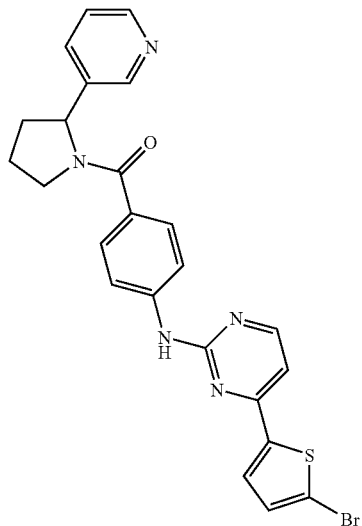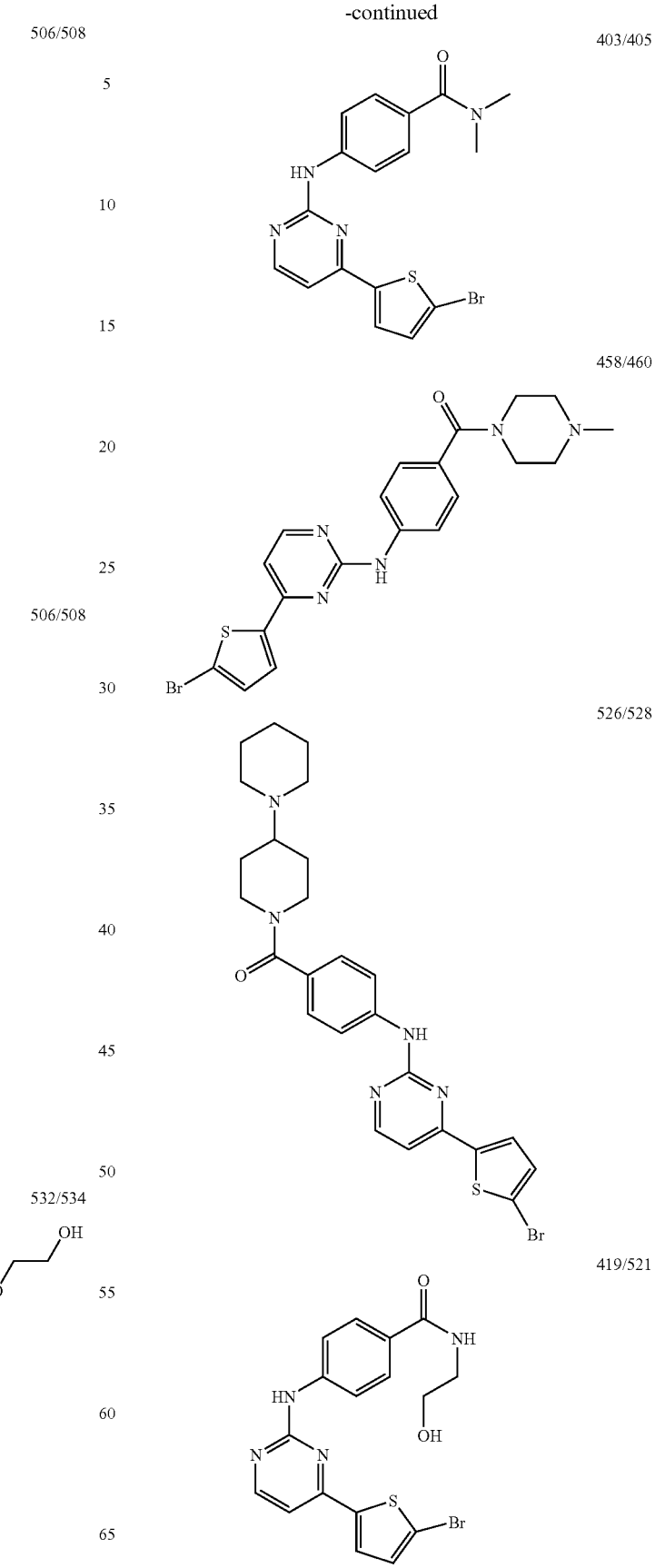

251
-continued
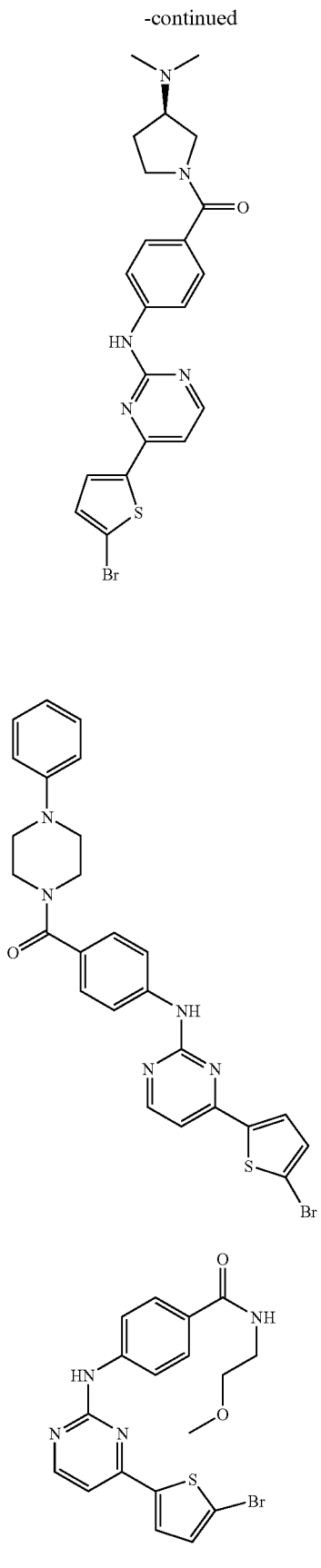
252
-continued
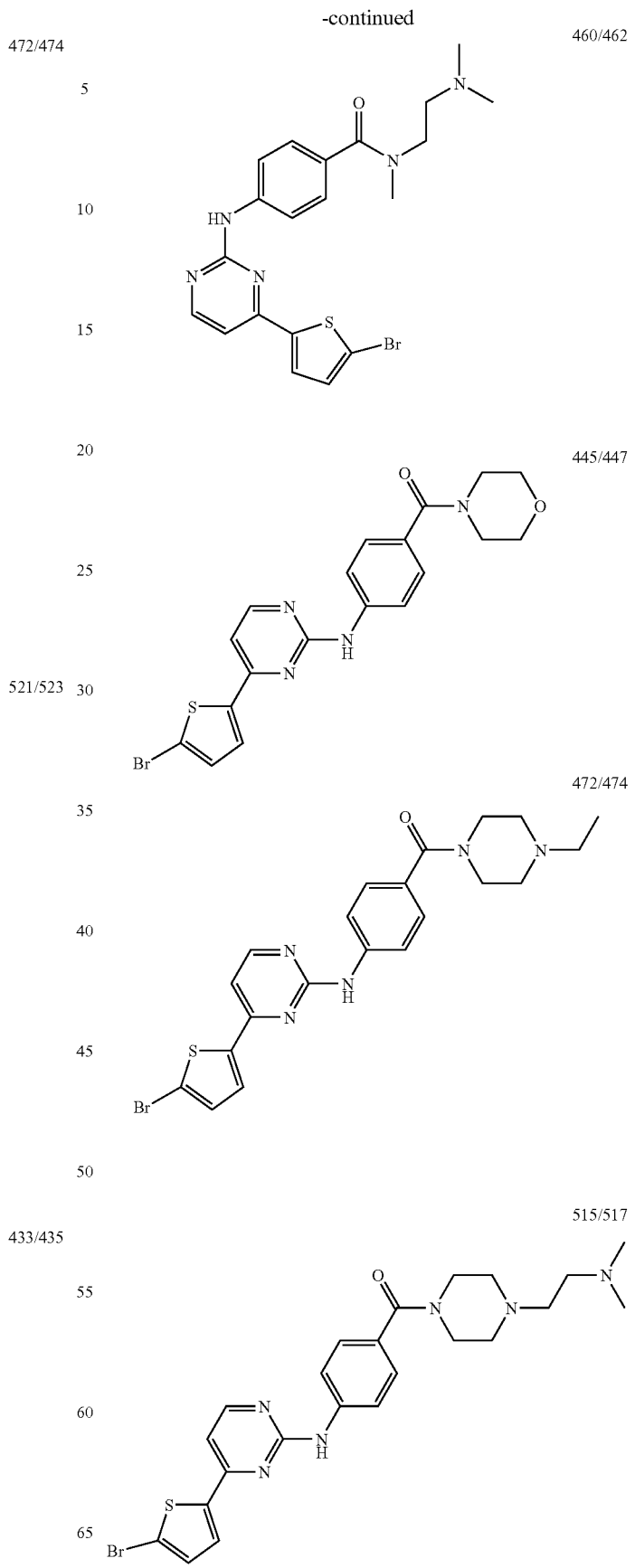

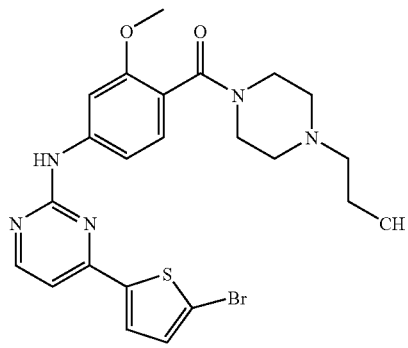
518/520
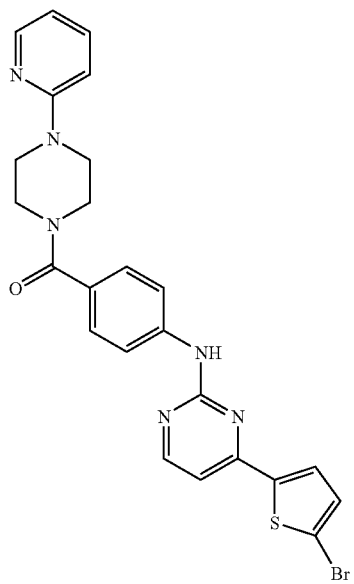
521/523
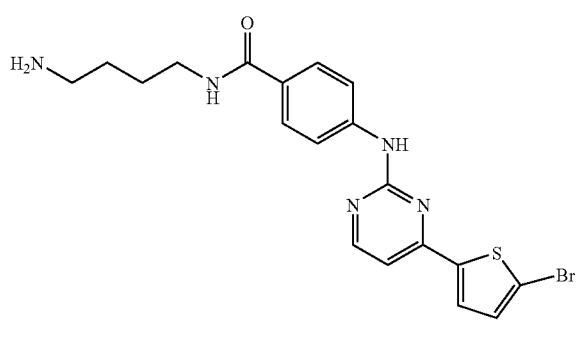
518/520
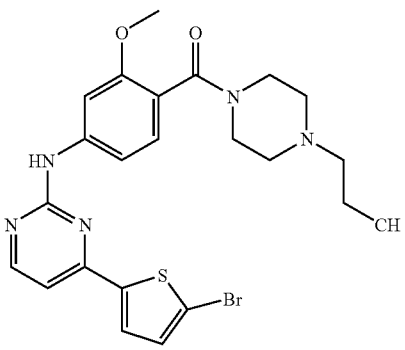
518/520
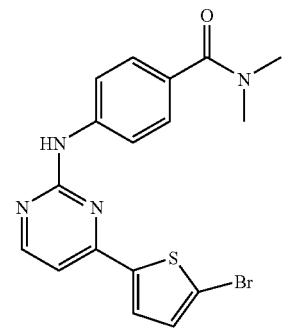
403/405
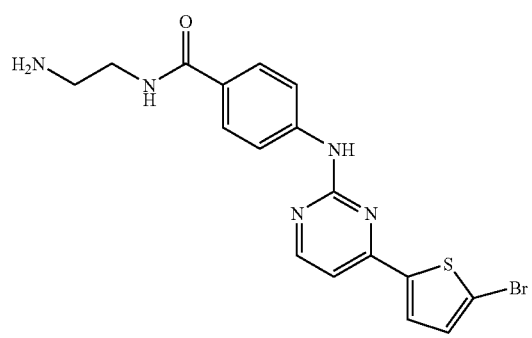
446/448
418/420
460/462

255
-continued
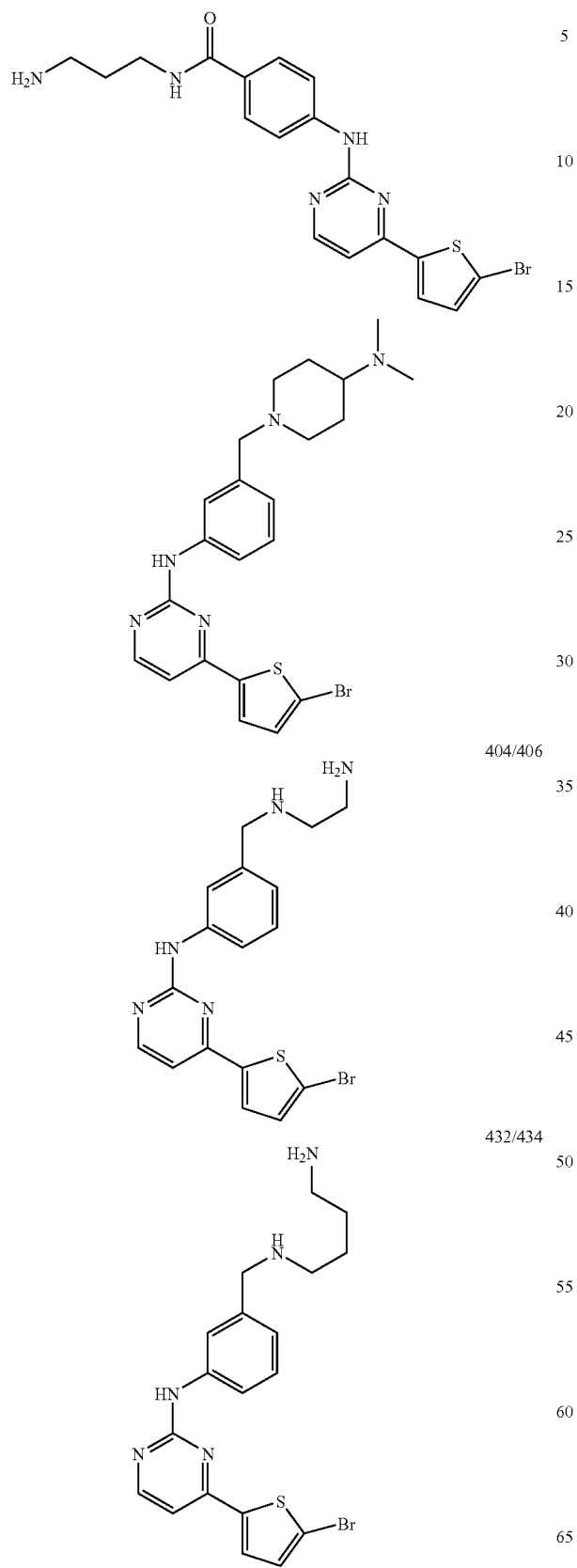
432/434
404/406
432/434
256
-continued
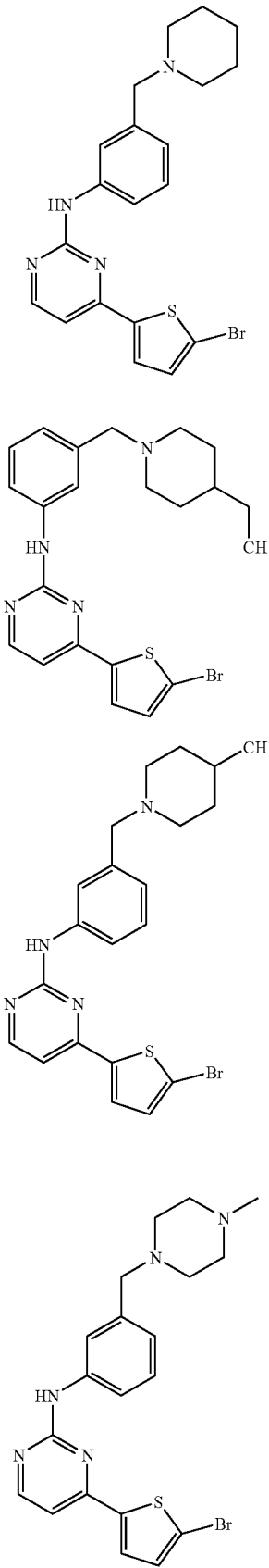
429/431
459/461
445/447
444/446

257
-continued
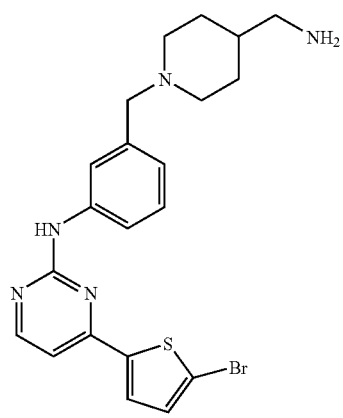
458/460
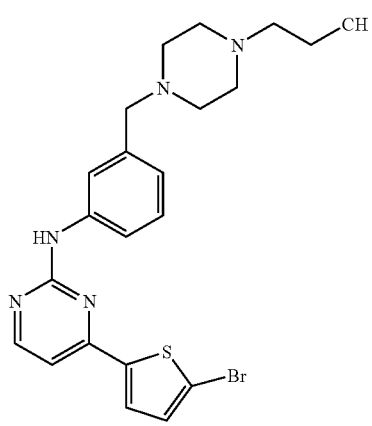
474/476
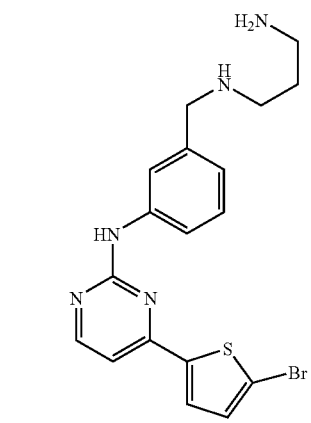
418/420
258
-continued
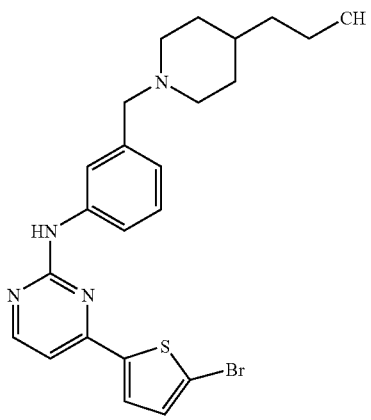
473/475

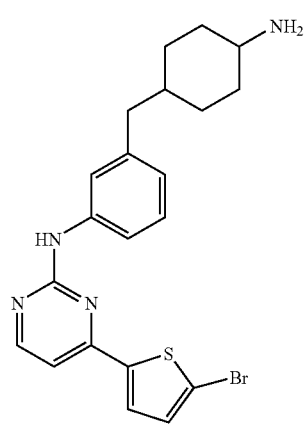
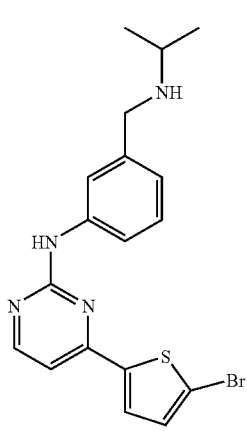
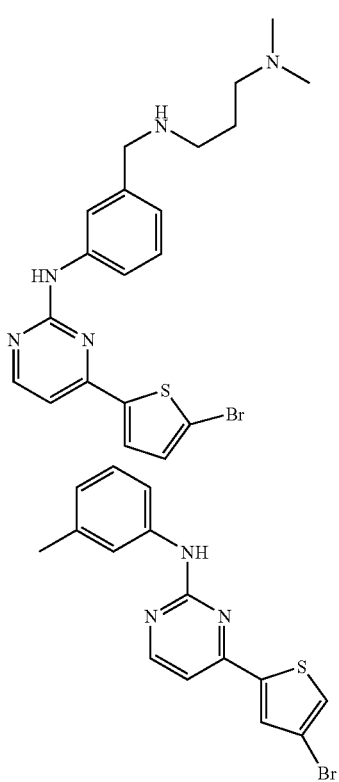
2. A pharmaceutical composition comprising a pharmaceutically acceptable excipient and a compound of claim 1.
3. A method for treating breast cancer or rheumatoid arthritis in a subject in need of such treatment comprising administering to the subject a therapeutically effective amount of a compound of claim 1.
* * * * *

UNITED STATES PATENT AND TRADEMARK OFFICE
CERTIFICATE OF CORRECTION

PATENT NO.        : 7,803,806 B2                                          Page 1 of 2
APPLICATION NO.   : 11/556033
DATED             : September 28, 2010
INVENTOR(S)       : William D. Arnold et al.

It is certified that error appears in the above-identified patent and that said Letters Patent is hereby corrected as shown below:

In the issued patent, please note the following corrections:

In Column 243, line 5, delete "          " and insert --          --.

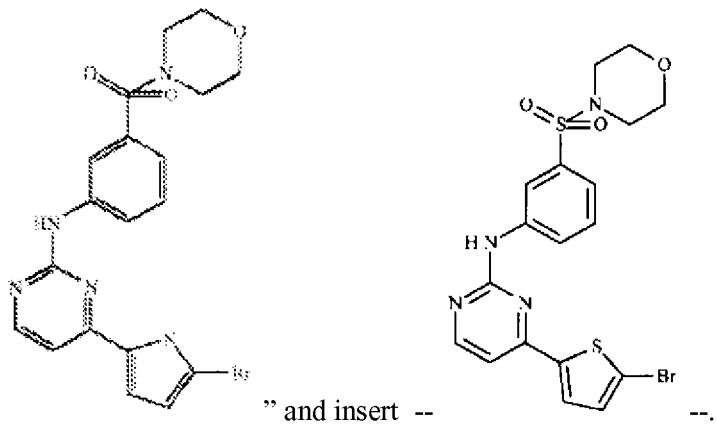

In Column 243, line 40, delete "          " and

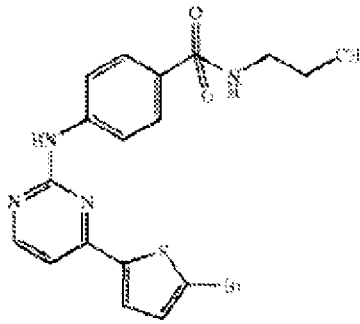

Signed and Sealed this
Fifteenth Day of November, 2011

David J. Kappos
*Director of the United States Patent and Trademark Office*

CERTIFICATE OF CORRECTION (continued)
U.S. Pat. No. 7,803,806 B2 insert -- 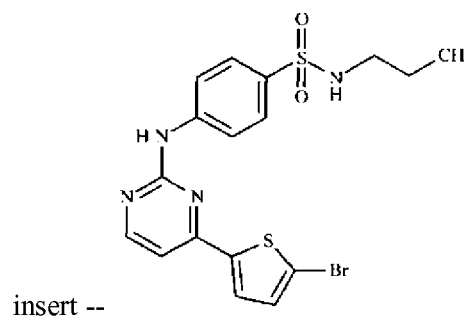 --.

In Column 243, line 55, delete " 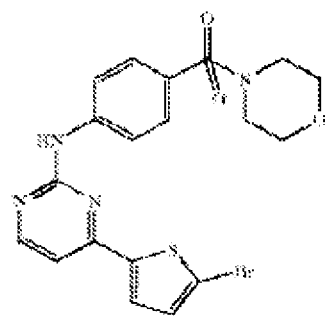 " and insert

-- 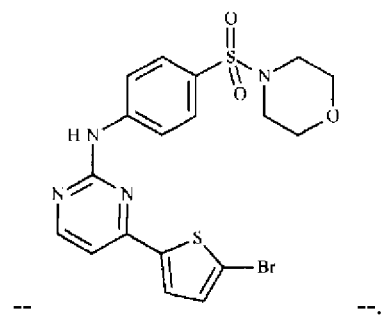 --.